US012696885B2

(12) United States Patent (10) Patent No.: US 12,696,885 B2
Lee et al. (45) Date of Patent: Aug. 4, 2026

(54) CELLS, VERTEBRATES, POPULATIONS AND METHODS

(71) Applicant: Kymab Limited, Cambridge (GB)

(72) Inventors: E-Chiang Lee, Cambridge (GB); Wei Wang, Cambridge (GB); John Kenneth Blackwood, Cambridge (GB); Roberto Magliozzi, Cambridge (GB); Andrew Wood, Cambridge (GB)

(73) Assignee: Kymab Limited, Cambridge (GB)

( * ) Notice: Subject to any disclaimer, the term of this patent is extended or adjusted under 35 U.S.C. 154(b) by 619 days.

(21) Appl. No.: 16/721,326

(22) Filed: Dec. 19, 2019

(65) Prior Publication Data

US 2020/0214274 A1 Jul. 9, 2020

Related U.S. Application Data

(63) Continuation-in-part of application No. PCT/EP2018/068309, filed on Jul. 5, 2018.

(30) Foreign Application Priority Data

Jul. 7, 2017 (GB) ..................................... 1710984

(51) Int. Cl.
*A01K 67/0278* (2024.01)
*A01K 67/0276* (2024.01)
*C07K 16/18* (2006.01)

(52) U.S. Cl.
CPC ...... *A01K 67/0278* (2013.01); *A01K 67/0276* (2013.01); *C07K 16/18* (2013.01); *A01K 2217/072* (2013.01); *A01K 2217/075* (2013.01); *A01K 2217/15* (2013.01); *A01K 2227/105* (2013.01); *A01K 2267/01* (2013.01); *C07K 2317/14* (2013.01); *C07K 2317/21* (2013.01); *C07K 2317/24* (2013.01); *C07K 2317/31* (2013.01); *C07K 2317/515* (2013.01); *C07K 2317/55* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,720,449 A | 1/1988 | Borror et al. | |
| 5,169,939 A | 12/1992 | Gefter et al. | |
| 5,545,806 A | 8/1996 | Lonberg et al. | |
| 5,545,807 A | 8/1996 | Surani et al. | |
| 5,565,321 A | 10/1996 | Spriggs et al. | |
| 5,633,425 A | 5/1997 | Lonberg et al. | |
| 5,770,429 A | 6/1998 | Lonberg et al. | |
| 5,789,215 A | 8/1998 | Berns et al. | |
| 5,807,715 A | 9/1998 | Morrison et al. | |
| 5,939,598 A | 8/1999 | Kucherlapati et al. | |
| 5,948,600 A | 9/1999 | Roschger et al. | |
| 6,114,598 A | 9/2000 | Kucherlapati et al. | |
| 6,130,364 A | 10/2000 | Jakobovits et al. | |
| 6,162,963 A | 12/2000 | Kucherlapati et al. | |
| 6,255,458 B1 | 7/2001 | Lonberg et al. | |
| 6,319,906 B1 | 11/2001 | Bennett et al. | |
| 6,395,487 B1 | 5/2002 | Bradley et al. | |
| 6,461,818 B1 | 10/2002 | Bradley et al. | |
| 6,596,541 B2 | 7/2003 | Murphy et al. | |
| 6,657,103 B1 | 12/2003 | Kucherlapati et al. | |
| 6,673,986 B1 | 1/2004 | Kucherlapati et al. | |
| 6,713,610 B1 | 3/2004 | Kucherlapati et al. | |
| 6,833,268 B1 | 12/2004 | Green et al. | |
| 6,914,128 B1 | 7/2005 | Salfeld et al. | |
| 6,992,235 B2 | 1/2006 | Bode et al. | |
| 6,998,514 B2 | 2/2006 | Bruggemann | |
| 7,105,348 B2 | 9/2006 | Murphy et al. | |
| 7,119,248 B1 | 10/2006 | Rajewsky et al. | |
| 7,205,140 B2 | 4/2007 | Gottschalk et al. | |
| 7,205,148 B2 | 4/2007 | Economides et al. | |
| 7,262,028 B2 * | 8/2007 | Van Berkel ............. A61P 43/00 435/7.1 |
| 7,294,754 B2 | 11/2007 | Poueymirou et al. | |
| 7,435,871 B2 | 10/2008 | Green et al. | |
| 7,501,552 B2 | 3/2009 | Lonberg et al. | |
| 7,605,237 B2 | 10/2009 | Stevens et al. | |
| 7,605,238 B2 | 10/2009 | Korman et al. | |
| 7,910,798 B2 | 3/2011 | Tanamachi et al. | |
| 7,932,431 B2 | 4/2011 | Bruggemann | |
| 8,158,419 B2 | 4/2012 | Lonberg et al. | |
| 8,502,018 B2 | 8/2013 | Murphy et al. | |
| 8,592,644 B2 | 11/2013 | Harriman et al. | |
| 8,642,835 B2 | 2/2014 | MacDonald et al. | |

(Continued)

FOREIGN PATENT DOCUMENTS

| | | |
|---|---|---|
| CA | 2307503 A1 | 11/2001 |
| CA | 2747534 A1 | 6/2010 |

(Continued)

OTHER PUBLICATIONS

Odegard et al Nature Reviews Immunology, 6(8): 573-583 (Year: 2006).*
Winter et al Molecular Immunology, 34(5), 359-366 (Year: 1997).*
Betz et al Cell, vol. 77, 239-249 (Year: 1994).*
Chinese Patent Office, Search Report (English Translation), Chinese Patent Application No. 201180039668.1, dated Jan. 3, 2014, 2 pages.
Chinese Patent Office, Search Report, Chinese Patent Application No. 201180039668.1, dated Jan. 3, 2014, 1 page.
Cho C., "Testicular and Epididymal ADAMs: Expression and Function During Fertilization," Nature Reviews Urology, 2012, vol. 9 (10), pp. 550-560.

(Continued)

*Primary Examiner* — Anoop K Singh
(74) *Attorney, Agent, or Firm* — Nutter McClennen & Fish LLP

(57) ABSTRACT

The invention relates to cells and non-human vertebrates for producing antibody chains (eg, truly common L or H chains), in particular for use in producing multi-specific antibodies useful for therapy or diagnosis.

19 Claims, 11 Drawing Sheets

Specification includes a Sequence Listing.

(56) References Cited

U.S. PATENT DOCUMENTS

| | | | |
|---|---|---|---|
| 8,697,940 B2 | 4/2014 | Macdonald et al. | |
| 8,754,287 B2 | 6/2014 | MacDonald et al. | |
| 8,771,988 B2 | 7/2014 | Goepfert et al. | |
| 8,791,323 B2 | 7/2014 | Murphy et al. | |
| 8,877,901 B2 | 11/2014 | Govindan | |
| 8,962,913 B2 | 2/2015 | Murphy | |
| 9,253,965 B2 * | 2/2016 | Bradley | C12N 15/8509 |
| 9,434,782 B2 | 9/2016 | Bradley et al. | |
| 9,445,581 B2 | 9/2016 | Bradley et al. | |
| 9,447,177 B2 | 9/2016 | Bradley et al. | |
| 9,504,236 B2 | 11/2016 | Bradley et al. | |
| 9,505,827 B2 | 11/2016 | Bradley et al. | |
| 9,783,593 B2 | 10/2017 | Bradley et al. | |
| 9,783,618 B2 | 10/2017 | Friedrich et al. | |
| 9,788,534 B2 | 10/2017 | Bradley et al. | |
| 9,844,212 B2 | 12/2017 | Macdonald et al. | |
| 9,896,516 B2 | 2/2018 | Bradley et al. | |
| 9,924,705 B2 | 3/2018 | Liang et al. | |
| 9,938,357 B2 | 4/2018 | Bradley et al. | |
| 9,938,358 B2 | 4/2018 | Bradley et al. | |
| 9,963,716 B2 | 5/2018 | Bradley et al. | |
| 10,064,398 B2 | 9/2018 | Bradley et al. | |
| 10,149,462 B2 | 12/2018 | Lee et al. | |
| 10,165,763 B2 | 1/2019 | Bradley et al. | |
| 10,226,033 B2 | 3/2019 | Bradley et al. | |
| 10,251,377 B2 | 4/2019 | Clube | |
| 10,605,808 B2 * | 3/2020 | Logtenberg | C07K 16/248 |
| 10,667,501 B2 | 6/2020 | Germaschewski et al. | |
| 10,730,930 B2 | 8/2020 | Bradley et al. | |
| 10,774,155 B2 | 9/2020 | Bradley et al. | |
| 10,966,412 B2 | 4/2021 | Lee et al. | |
| 11,051,497 B2 | 7/2021 | Friedrich et al. | |
| 11,297,810 B2 | 4/2022 | Bradley et al. | |
| 11,297,811 B2 | 4/2022 | Clube | |
| 11,399,522 B2 | 8/2022 | Lee et al. | |
| 11,564,380 B2 | 1/2023 | Bradley et al. | |
| 11,606,941 B2 | 3/2023 | Bradley et al. | |
| 11,707,056 B2 | 7/2023 | Bradley et al. | |
| 11,820,810 B2 | 11/2023 | Bradley et al. | |
| 2002/0088016 A1 | 7/2002 | Bruggemann | |
| 2002/0183275 A1 | 12/2002 | Murphy et al. | |
| 2003/0070185 A1 | 4/2003 | Jakobovits et al. | |
| 2003/0108925 A1 | 6/2003 | Dix et al. | |
| 2003/0167489 A1 | 9/2003 | Rajewsky et al. | |
| 2003/0217373 A1 | 11/2003 | Green et al. | |
| 2004/0077089 A1 | 4/2004 | Xin et al. | |
| 2004/0128703 A1 | 7/2004 | Shizuya | |
| 2004/0209268 A1 | 10/2004 | Azuma | |
| 2004/0231012 A1 | 11/2004 | Bruggemann | |
| 2005/0048621 A1 | 3/2005 | Grasso et al. | |
| 2005/0260679 A1 | 11/2005 | Kellerman et al. | |
| 2006/0008892 A1 | 1/2006 | Yacoby-Zeevi | |
| 2006/0015949 A1 | 1/2006 | Lonberg et al. | |
| 2006/0015957 A1 | 1/2006 | Lonberg et al. | |
| 2006/0021074 A1 | 1/2006 | Kellermann et al. | |
| 2006/0199204 A1 | 9/2006 | Dix et al. | |
| 2007/0280945 A1 | 12/2007 | Stevens et al. | |
| 2008/0098490 A1 | 4/2008 | Jakobovits et al. | |
| 2009/0083870 A1 | 3/2009 | Horn et al. | |
| 2009/0083879 A1 | 3/2009 | Dhugga | |
| 2009/0093059 A1 | 4/2009 | Baszczynski et al. | |
| 2009/0098134 A1 | 4/2009 | Buelow | |
| 2009/0209036 A1 | 8/2009 | Reynaud et al. | |
| 2009/0307787 A1 | 12/2009 | Grosveld et al. | |
| 2010/0011450 A1 | 1/2010 | Garcia et al. | |
| 2010/0069614 A1 | 3/2010 | Houtzager et al. | |
| 2010/0146647 A1 | 6/2010 | Logtenberg et al. | |
| 2010/0196367 A1 | 8/2010 | Day | |
| 2010/0330676 A1 | 12/2010 | Horowitz et al. | |
| 2011/0119779 A1 | 5/2011 | Shizuya et al. | |
| 2011/0138489 A1 | 6/2011 | Tanamachi et al. | |
| 2011/0145937 A1 | 6/2011 | MacDonald et al. | |
| 2011/0195454 A1 | 8/2011 | McWhirter | |
| 2011/0236378 A1 | 9/2011 | Green et al. | |
| 2011/0283376 A1 | 11/2011 | Murphy et al. | |
| 2012/0021409 A1 * | 1/2012 | McWhirter | C12N 15/8509 435/6.1 |
| 2012/0070861 A1 | 3/2012 | Macdonald et al. | |
| 2012/0073004 A1 | 3/2012 | MacDonald et al. | |
| 2012/0096572 A1 | 4/2012 | Macdonald et al. | |
| 2012/0195910 A1 | 8/2012 | Wu et al. | |
| 2012/0204278 A1 | 8/2012 | Bradley et al. | |
| 2012/0233715 A1 | 9/2012 | Kuroiwa et al. | |
| 2012/0322108 A1 | 12/2012 | Macdonald et al. | |
| 2013/0039850 A1 | 2/2013 | Lonberg et al. | |
| 2013/0096287 A1 | 4/2013 | Macdonald et al. | |
| 2013/0102031 A1 | 4/2013 | King et al. | |
| 2013/0160153 A1 | 6/2013 | Macdonald et al. | |
| 2013/0198879 A1 | 8/2013 | McWhirter et al. | |
| 2013/0212719 A1 | 8/2013 | Macdonald et al. | |
| 2013/0243759 A1 | 9/2013 | Friedrich et al. | |
| 2013/0247235 A1 | 9/2013 | McWhirter et al. | |
| 2013/0254911 A1 | 9/2013 | Macdonald et al. | |
| 2013/0263292 A1 | 10/2013 | Liang et al. | |
| 2013/0263293 A1 | 10/2013 | Bradley et al. | |
| 2013/0323790 A1 | 12/2013 | Macdonald et al. | |
| 2013/0323791 A1 | 12/2013 | Macdonald et al. | |
| 2013/0326647 A1 | 12/2013 | Macdonald et al. | |
| 2013/0333057 A1 | 12/2013 | Macdonald et al. | |
| 2014/0017228 A1 | 1/2014 | Macdonald et al. | |
| 2014/0017782 A1 | 1/2014 | Murphy et al. | |
| 2014/0041067 A1 | 2/2014 | Bradley et al. | |
| 2014/0120582 A1 | 5/2014 | Bradley et al. | |
| 2014/0130193 A1 | 5/2014 | Macdonald et al. | |
| 2014/0130194 A1 | 5/2014 | Macdonald et al. | |
| 2014/0137275 A1 | 5/2014 | Macdonald et al. | |
| 2014/0150125 A1 | 5/2014 | Bradley et al. | |
| 2014/0150126 A1 | 5/2014 | Bradley et al. | |
| 2014/0182003 A1 | 6/2014 | Bradley et al. | |
| 2014/0201854 A1 | 7/2014 | Bradley et al. | |
| 2014/0201856 A1 | 7/2014 | Bradley et al. | |
| 2014/0212416 A1 | 7/2014 | Friedrich et al. | |
| 2014/0213773 A1 | 7/2014 | Macdonald et al. | |
| 2014/0323327 A1 | 10/2014 | Bradley et al. | |
| 2014/0325690 A1 | 10/2014 | Bradley et al. | |
| 2014/0331339 A1 | 11/2014 | Bradley et al. | |
| 2014/0331344 A1 | 11/2014 | Friedrich et al. | |
| 2014/0356908 A1 | 12/2014 | Grosveld et al. | |
| 2014/0359797 A1 | 12/2014 | Bradley et al. | |
| 2015/0033369 A1 | 1/2015 | Bradley et al. | |
| 2015/0033372 A1 | 1/2015 | Bradley et al. | |
| 2015/0040250 A1 | 2/2015 | Bradley et al. | |
| 2015/0082466 A1 | 3/2015 | Clube | |
| 2015/0113669 A1 | 4/2015 | Bradley et al. | |
| 2015/0133641 A1 | 5/2015 | Germaschewski et al. | |
| 2015/0196015 A1 | 7/2015 | Macdonald et al. | |
| 2015/0334998 A1 | 11/2015 | Bradley et al. | |
| 2016/0044900 A1 | 2/2016 | Bradley et al. | |
| 2016/0150768 A1 | 6/2016 | Bradley et al. | |
| 2016/0219846 A1 | 8/2016 | Liang et al. | |
| 2016/0345551 A1 | 12/2016 | Bradley et al. | |
| 2016/0345552 A1 | 12/2016 | Bradley et al. | |
| 2016/0353719 A1 | 12/2016 | Friedrich et al. | |
| 2017/0051045 A1 | 2/2017 | Bradley et al. | |
| 2017/0071174 A1 | 3/2017 | Bradley et al. | |
| 2017/0081423 A1 | 3/2017 | Bradley et al. | |
| 2017/0094956 A1 | 4/2017 | Bradley et al. | |
| 2017/0096498 A1 | 4/2017 | Bradley et al. | |
| 2017/0099815 A1 | 4/2017 | Bradley et al. | |
| 2017/0099816 A1 | 4/2017 | Bradley et al. | |
| 2017/0099817 A1 | 4/2017 | Bradley et al. | |
| 2017/0101482 A1 | 4/2017 | Bradley et al. | |
| 2017/0101483 A1 | 4/2017 | Bradley et al. | |
| 2017/0105396 A1 | 4/2017 | Bradley et al. | |
| 2017/0135327 A1 | 5/2017 | Lee et al. | |
| 2017/0320936 A1 | 11/2017 | Bradley et al. | |
| 2017/0354131 A1 | 12/2017 | Bradley et al. | |
| 2018/0030121 A1 | 2/2018 | Bradley et al. | |
| 2018/0142006 A1 | 5/2018 | Logtenberg et al. | |
| 2018/0282761 A1 | 10/2018 | Bradley et al. | |
| 2018/0295821 A1 | 10/2018 | Friedrich et al. | |
| 2018/0298112 A1 | 10/2018 | Bradley | |
| 2019/0174729 A1 | 6/2019 | Lee et al. | |
| 2019/0208753 A1 | 7/2019 | Clube | |

(56) References Cited

U.S. PATENT DOCUMENTS

| | | | |
|---|---|---|---|
| 2019/0327946 A1 | 10/2019 | Bradley et al. |
| 2020/0205384 A1 | 7/2020 | Friedrich et al. |
| 2020/0214274 A1 | 7/2020 | Lee et al. |
| 2020/0267952 A1 | 8/2020 | Germaschewski et al. |
| 2020/0317751 A1 | 10/2020 | Bradley et al. |
| 2020/0317752 A1 | 10/2020 | Bradley et al. |
| 2020/0337280 A1 | 10/2020 | Bradley et al. |
| 2020/0352144 A1 | 11/2020 | Bradley et al. |
| 2020/0352145 A1 | 11/2020 | Bradley et al. |
| 2020/0375158 A1 | 12/2020 | Bradley et al. |
| 2021/0079118 A1 | 3/2021 | Bradley et al. |
| 2021/0204530 A1 | 7/2021 | Lee et al. |
| 2022/0000085 A1 | 1/2022 | Friedrich et al. |
| 2022/0287283 A1 | 9/2022 | Bradley et al. |
| 2022/0295765 A1 | 9/2022 | Clube |
| 2023/0157264 A1 | 5/2023 | Lee et al. |
| 2023/0159660 A1 | 5/2023 | Bradley et al. |
| 2023/0225302 A1 | 7/2023 | Bradley et al. |
| 2023/0263143 A1 | 8/2023 | Bradley et al. |
| 2023/0270088 A1 | 8/2023 | Bradley et al. |
| 2024/0057572 A1 | 2/2024 | Bradley et al. |

FOREIGN PATENT DOCUMENTS

| | | | | |
|---|---|---|---|---|
| CA | 2820824 A1 | 10/2012 | | |
| CN | 102123582 A | 7/2011 | | |
| CN | 104334732 A | 2/2015 | | |
| DE | 10251918 A1 | 5/2004 | | |
| EP | 1780272 A1 | 5/2007 | | |
| EP | 0937140 B1 | 9/2007 | | |
| EP | 2147594 A1 * | 1/2010 | ........ A01K 67/0275 |
| EP | 2517556 B1 | 10/2012 | | |
| EP | 2517557 A2 | 10/2012 | | |
| EP | 2147594 B1 | 11/2013 | | |
| EP | 2480676 B1 | 4/2016 | | |
| GB | 2398784 A | 9/2004 | | |
| GB | 2403475 A | 1/2005 | | |
| JP | 2004524841 A | 8/2004 | | |
| JP | 2005510253 A | 4/2005 | | |
| JP | 2008507257 A | 3/2008 | | |
| JP | 2010512749 A | 4/2010 | | |
| JP | 2011525808 A | 9/2011 | | |
| JP | 2012521211 A | 9/2012 | | |
| JP | 2015-512634 A | 4/2015 | | |
| KR | 20050042792 A | 5/2005 | | |
| WO | 9004036 A1 | 4/1990 | | |
| WO | 9100906 A1 | 1/1991 | | |
| WO | 9110741 A1 | 7/1991 | | |
| WO | 9203918 A1 | 3/1992 | | |
| WO | 9312227 A1 | 6/1993 | | |
| WO | 9402602 A1 | 2/1994 | | |
| WO | 9404667 A1 | 3/1994 | | |
| WO | 9425585 A1 | 11/1994 | | |
| WO | 9630498 A1 | 10/1996 | | |
| WO | 9824884 A1 | 6/1998 | | |
| WO | 9824893 A2 | 6/1998 | | |
| WO | 9850431 A2 | 11/1998 | | |
| WO | 1998050431 A2 | 11/1998 | | |
| WO | 9945962 A1 | 9/1999 | | |
| WO | 0026373 A1 | 5/2000 | | |
| WO | 0071585 A1 | 11/2000 | | |
| WO | 0208409 A2 | 1/2002 | | |
| WO | 0236789 A2 | 5/2002 | | |
| WO | 0243478 A2 | 6/2002 | | |
| WO | 02053596 A2 | 7/2002 | | |
| WO | 02059263 A2 | 8/2002 | | |
| WO | 02066630 A1 | 8/2002 | | |
| WO | 02070648 A2 | 9/2002 | | |
| WO | 03006639 A1 | 1/2003 | | |
| WO | 03047336 A2 | 6/2003 | | |
| WO | 03061363 A2 | 7/2003 | | |
| WO | 2004009618 A2 | 1/2004 | | |
| WO | 2004044150 A2 | 5/2004 | | |
| WO | 2004050838 A2 | 6/2004 | | |
| WO | 2005003364 A2 | 1/2005 | | |
| WO | 2005004592 A2 | 1/2005 | | |
| WO | 2005019463 A1 | 3/2005 | | |
| WO | 2005058815 A2 | 6/2005 | | |
| WO | 2005092926 A2 | 10/2005 | | |
| WO | 2006008548 A2 | 1/2006 | | |
| WO | 2006029459 A1 | 3/2006 | | |
| WO | 2006044492 A2 | 4/2006 | | |
| WO | 2006055704 A2 | 5/2006 | | |
| WO | 2006068953 A2 | 6/2006 | | |
| WO | 2006117699 A2 | 11/2006 | | |
| WO | 2006122442 A1 | 11/2006 | | |
| WO | 2007085837 A1 | 8/2007 | | |
| WO | 2007096779 A2 | 8/2007 | | |
| WO | 2007117410 A2 | 10/2007 | | |
| WO | 2007143168 A2 | 12/2007 | | |
| WO | 2008022391 A1 | 2/2008 | | |
| WO | 2008054606 A2 | 5/2008 | | |
| WO | 2008070367 A2 | 6/2008 | | |
| WO | 2008076379 A2 | 6/2008 | | |
| WO | 2008081197 A1 | 7/2008 | | |
| WO | 2008094178 A2 | 8/2008 | | |
| WO | 2008103474 A1 | 8/2008 | | |
| WO | 2008108918 A1 | 9/2008 | | |
| WO | 2008118970 A2 | 10/2008 | | |
| WO | 2008122886 A2 | 10/2008 | | |
| WO | 2008151081 A1 | 12/2008 | | |
| WO | 2009013620 A2 | 1/2009 | | |
| WO | 2009018411 A1 | 2/2009 | | |
| WO | 2009023540 A1 | 2/2009 | | |
| WO | 2009076464 A2 | 6/2009 | | |
| WO | 2009080254 A1 | 7/2009 | | |
| WO | 2009097006 A2 | 8/2009 | | |
| WO | 2009118524 A2 | 10/2009 | | |
| WO | 2009129247 A2 | 10/2009 | | |
| WO | 2009143472 A2 | 11/2009 | | |
| WO | WO-2009157771 A2 * | 12/2009 | ........ A01K 67/0275 |
| WO | 2010039900 A2 | 4/2010 | | |
| WO | 2010070263 A1 | 6/2010 | | |
| WO | 2010077854 A1 | 7/2010 | | |
| WO | 2010097385 A1 | 9/2010 | | |
| WO | 2010109165 A2 | 9/2010 | | |
| WO | 2010113039 A1 | 10/2010 | | |
| WO | 2011004192 A1 | 1/2011 | | |
| WO | 2011008093 A1 | 1/2011 | | |
| WO | 2011014469 A1 | 2/2011 | | |
| WO | 2011056864 A1 | 5/2011 | | |
| WO | 2011062206 A1 | 5/2011 | | |
| WO | 2011062207 A1 | 5/2011 | | |
| WO | 2011071957 A1 | 6/2011 | | |
| WO | 2011072204 A1 | 6/2011 | | |
| WO | 2011097603 A1 | 8/2011 | | |
| WO | 2011146121 A1 | 11/2011 | | |
| WO | 2011158009 A1 | 12/2011 | | |
| WO | 2011163311 A1 | 12/2011 | | |
| WO | 2011163314 A1 | 12/2011 | | |
| WO | 2012/007167 A1 | 1/2012 | | |
| WO | 2012018764 A1 | 2/2012 | | |
| WO | 2012023053 A2 | 2/2012 | | |
| WO | 2012064682 A1 | 5/2012 | | |
| WO | 2012/088313 A1 | 6/2012 | | |
| WO | 2012141798 A1 | 10/2012 | | |
| WO | 2012148873 A2 | 11/2012 | | |
| WO | 2013022782 A1 | 2/2013 | | |
| WO | 2013041844 A2 | 3/2013 | | |
| WO | 2013041845 A2 | 3/2013 | | |
| WO | 2013041846 A2 | 3/2013 | | |
| WO | 2013045916 A1 | 4/2013 | | |
| WO | 2013059230 A1 | 4/2013 | | |
| WO | 2013061078 A1 | 5/2013 | | |
| WO | 2013061098 A2 | 5/2013 | | |
| WO | 2013079953 A1 | 6/2013 | | |
| WO | 2013096142 A1 | 6/2013 | | |
| WO | 2013116609 A1 | 8/2013 | | |
| WO | 2013130981 A1 | 9/2013 | | |
| WO | 2013134263 A1 | 9/2013 | | |
| WO | 2013/144566 A2 | 10/2013 | | |
| WO | 2013144567 A1 | 10/2013 | | |
| WO | 2013166236 A1 | 11/2013 | | |
| WO | 2013171505 A2 | 11/2013 | | |

(56) References Cited

FOREIGN PATENT DOCUMENTS

| WO | 2013176772 A1 | 11/2013 |
| WO | 2014093622 A2 | 6/2014 |
| WO | 2014130690 A1 | 8/2014 |
| WO | 2015049517 A2 | 4/2015 |
| WO | 2019008123 A2 | 1/2019 |

OTHER PUBLICATIONS

Choi I., et al., "Characterization and Comparative Genomic Analysis of Intronless Adams with Testicular Gene Expression," Genomics, 2004, vol. 83 (4), pp. 636-646.
Clark J ., et al., "A Future for Transgenic Livestock," Nature Reviews Genetics, 2003, vol. 4 (10), pp. 825-833.
Clark L.A., et al., "Trends in Antibody Sequence Changes During the Somatic Hypermutation Process," The Journal of Immunology, 2006, vol. 177 (1), pp. 333-340.
Clark M.R., "IgG Effector Mechanisms," Chemical Immunology, 1997, vol. 65, pp. 88-110.
Colbère-Garapin F., et al., "A New Dominant Hybrid Selective Marker for Higher Eukaryotic Cells," Journal of Molecular Biology, 1981, vol. 150 (1), pp. 1-14.
Collins A.M., et al., "The reported germline repertoire of human immunoglobulin kappa chain genes is relatively complete and accurate," Immunogenetics, 2008, vol. 60, pp. 669-676.
Collins F.S., et al., "A Mouse for All Reasons," Cell, 2007, vol. 128 (1), pp. 9-13.
Collis A.V.J., et al., "Analysis of the Antigen Combining Site: Correlations Between Length and Sequence Composition of the Hypervariable Loops and the Nature of the Antigen," Journal of Molecular Biology, 2003, vol. 325, pp. 337-354.
Combriato G., et al., "Regulation of Human Ig? Light Chain Gene Expression by NF-KB1," The Journal of Immunology, 2002, vol. 168 (3), pp. 1259-1266.
Conrath K.E., et al., "Camel Single-domain Antibodies as Modular Building Units in Bispecific and Bivalent Antibody Constructs," The Journal of Biological Chemistry, 2001, vol. 276 (10), pp. 7346-7350.
Copeland N.G., et al., "Recombineering: A Powerful New Tool for Mouse Functional Genomics," Nature Reviews Genetics, Oct. 2001, vol. 2 (10), pp. 769-779.
Corbett S.J., et al., "Sequence of the Human Immunoglobulin Diversity (D) Segment Locus: A Systematic Analysis Provides No Evidence for the Use of DIR Segments, Inverted D Segments, "Minor" D Segments or D-D Recombination," Journal of Molecular Biology, 1997, vol. 270 (4), pp. 587-597.
Corti D., et al., "A Neutralizing Antibody Selected from Plasma Cells that Binds to Group 1 and Group 2 Influenza A Hemagglutinins," Science, 2011, vol. 333 (6044), pp. 850-856.
Crouch E.E., et al., "Regulation of AID expression in the Immune Response," Journal of Experimental Medicine, May 2007, vol. 204 (5), pp. 1145-1156.
Cuesta A.M., et al., "Multivalent Antibodies: When Design Surpasses Evolution," Trends in Biotechnology, 2010, vol. 28 (7), pp. 355-362.
D'Eustachio P., et al., "Mouse Chromosome 12," Mammalian Genome, 1998, vol. 8, pp. S241-257.
Dafhnis-Calas F., et al., "Iterative in vivo assembly of large and complex transgenes by combining the activities of ?C31 integrase and Cre recombinase," Nucleic Acids Research, Dec. 2005, vol. 33(22), pp. e189-1-e189-14.
Daukss, Dana M., Third-Party Pre-Issuance Submission Under 37 CFR 1.290 in U.S. Appl. No. 16/725,707, dated Dec. 28, 2020, 46 pages.
Daukss, Dana M., Third-Party Pre-Issuance Submission Under 37 CFR 1.290 in U.S. Appl. No. 16/870,365, dated Mar. 15, 2021, 36 pages.
Daukss, Dana M., Third-Party Pre-Issuance Submission Under 37 CFR 1.290 in U.S. Appl. No. 16/870,365, dated Mar. 15, 2021, 45 pages (Second Submission).
Daukss, Dana M., Third-Party Pre-Issuance Submission Under 37 CFR 1.290 in U.S. Appl. No. 16/905,557, dated Mar. 9, 2021, 63 pages (Second Submission).
Daukss, Dana M., Third-Party Pre-Issuance Submission Under 37 CFR 1.290 in U.S. Appl. No. 16/905,557, dated Mar. 9, 2021, 67 pages.
Davies N.P., et al., "Creation of Mice Expressing Human Antibody Light Chains by Introduction of a Yeast Artificial Chromosome Containing the Core Region of the Human Immunoglobulin k Locus," Nature Biotechnology, Aug. 1993, vol. 11 (8), pp. 911-914.
Davis C.G., et al., "Production of Human Antibodies from Transgenic Mice," Antibody Engineering, Methods and Protocols, Methods in Mol. Biol., Chapter 10, 2004, pp. 191-200.
De Bono B., et al., "VH Gene Segments in the Mouse and Human Genomes," Journal of Molecular Biology, 2004, vol. 342 (1), pp. 131-143.
De Kruif J., et al., "Human Immunoglobulin Repertoires Against Tetanus Toxoid Contain a Large and Diverse Fraction of High-Affinity Promiscuous VH Genes," Journal of Molecular Biology, 2009, vol. 387 (3), pp. 548-558.
De Saint Vincent B.R., et al., "Homologous Recombination in Mammalian Cells Mediates Formation of a Functional Gene from Two Overlapping Gene Fragments," Proceedings of the National Academy of Sciences of the U.S.A, 1983, vol. 80 (7), pp. 2002-2006.
De Wildt R.M.T., et al., "Analysis of Heavy and Light Chain Pairings Indicates that Receptor Editing Shapes the Human Antibody Repertoire," Journal of Molecular Biology, 1999, vol. 285, pp. 895-901.
Dechiara T.M., et al., "Producing Fully ES Cell-Derived Mice from Eight-Cell Stage Embryo Injections," Methods in Enzymology, Chapter 16, 2010, vol. 476, pp. 285-294.
Dechiara T.M., et al., "VelociMouse: Fully ES Cell-Derived FO-Generation Mice Obtained from the Injection of ES Cells into Eight-Cell-Stage Embryos," Methods in Molecular Biology, Chapter 16, 2009, vol. 530, pp. 311-324.
Declerck P.J., et al., "Generation of Monoclonal Antibodies against autologous Proteins in Gene-inactivated Mice," The Journal of Biological Chemistry, Apr. 1995, vol. 270 (15), pp. 8397-8400.
Decloux, A.M., Attorney for Applicant, Amendment and Response After Final Rejection—U.S. Appl. No. 13/846,672, filed May 10, 2016, 16 pages.
Defranco, Anthony L., Ph.D., Declaration, Interparties Review AIA No. IPR2019-01577 U.S. Pat. No. 9,434,782), dated Sep. 9, 2019, 113 pages.
Defranco, Anthony L., Ph.D., Declaration, Interparties Review AIA No. IPR2019-01578 U.S. Pat. No. 9,505,827), dated Sep. 9, 2019, 121 pages.
Defranco, Anthony L., Ph.D., Declaration, Interparties Review AIA No. IPR2019-01579 (U.S. Pat. No. 9,447,177), dated Sep. 20, 2019, 103 pages.
Deftos M., et al., "Defining the Genetic Origins of Three Rheumatoid Synovium-derived IgG Rheumatoid Factors," Journal of Clinical Investigations, Jun. 1994, vol. 93, pp. 2545-2553.
Delves P.J., et al., "Antibodies," Chapter 3, Roitt's Essential Immunology, Eleventh edition, 2006, pp. 37-60.
Deng C., et al., "Reexamination of Gene Targeting Frequency as a Function of the Extent of Homology Between the Targeting Vector and the Target Locus," Molecular and Cellular Biology, Aug. 1992, vol. 12 (8), pp. 3365-3371.
Denome R.M., et al., "Patterns of Polyadenylation Site Selection in Gene Constructs Containing Multiple Polyadenylation Signals," Molecular and Cellular Biology, 1988, vol. 8 (11), pp. 4829-4839.
Deonarain R., et al., "Impaired Antiviral Response and Alpha/Beta Interferon Induction in Mice Lacking Beta Interferon," Journal of Virology, Apr. 2000, vol. 74(4), pp. 3404-3409.
Dewitt W.S., et al., "A Public Database of Memory and Naïve B-Cell Receptor Sequences," Plos One, Aug. 2016, 18 pages.
Di Noia J.M., et al., "Molecular Mechanisms of Antibody Somatic Hypermutation," Annual Review of Biochemistry, Jun. 2007, vol. 76(1), pp. 1-22.
Diez-Roux G., et al., "A High-Resolution Anatomical Atlas of the Transcriptome in the Mouse Embryo," PLoS Biology, 2011, vol. 9 (1), pp. 1-13.

(56)                    References Cited

OTHER PUBLICATIONS

Ding L., et al., "Generation of High-Affinity Fully Human Anti-Interleukin-8 Antibodies from its cDNA by Two-Hybrid Screening and Affinity Maturation in Yeast," Protein Science, 2010, vol. 19 (10), pp. 1957-1966.

Doetschman T., et al., "Establishment of Hamster Blastocyst-Derived Embryonic Stem (ES) Cells," Developmental Biology, 1988, vol. 127 (1), pp. 224-227.

Doetschman T., et al., "Targeted Mutation of the Hprt Gene in Mouse Embryonic Stem Cells," Proceedings of the National Academy of Sciences of the U.S.A, 1988, vol. 85 (22), pp. 8583-8587.

Donohoe M.E., et al., "Transgenic Human ?5 Rescues the Murine ?5 Nullizygous Phenotype," Journal of Immunology, 2000, vol. 164, pp. 5269-5276.

Examination Report issued on Feb. 26, 2021 in European Patent Application No. 18743421.2.

Winter et al., Insertion of 2 kb of bacteriophage DNA between an immunoglobulin promoter and leader exon stops somatic hypermutation in a k transgene, Molecular immunology, 1997, 34.5: 359-366.

Written Opinion issued on Jan. 15, 2019 in International Patent Application No. PCT/EP2018/068309.

Odegard, Valerie H. and Schatz, David G., Targeting of somatic hypermutation, Nature Reviews 4 Immunology, 2006, 6.8: 573-583.

1st International MUGEN Conference on Animal Models for Human Immunological Disease, Sep. 10-13, 2006—Athens Greece (Abstracts 1-52), 52 pages.

1st International MUGEN Conference on Animal Models for Human Immunological Disease, Sep. 10-13, 2006—Athens Greece (Scientific Programme & Presentations), 4 pages.

[No Author Listed] Imgt Repertoire (IG and TR), Gene table: human (*Homo sapiens*) IGHD, created Apr. 18, 1997, last updated Jan. 17, 2020, 3 pages. [retrieved from the internet under: http://www.imgt.org/IMGTrepertoire/].

Adams D.J., et al., "A Genome-Wide, End-Sequenced 129Sv BAC Library Resource for Targeting Vector Construction," Genomics, 2005, vol. 86 (6), pp. 753-758.

Adams D.J., et al., "Contemporary approaches for modifying the mouse genome," Physiological Genomics, vol. 34, Jun. 2008, pp. 225-238.

Adams D.J., et al., "Mutagenic Insertion and Chromosome Engineering Resource (MICER)," Nature Genetics, vol. 36 (8), Aug. 2004, pp. 867-871.

Adekar S.P., et al., "A Natural Human IgM Antibody that Neutralizes Botulinum Neurotoxin in vivo," Hybridoma, 2008, vol. 27 (2), pp. 65-69.

Affidavits Evidencing Murphy Slides as Printed Publication, dated Jun. 20, 2016, 84 pages.

Aguilera R.J., et al., "Characterization of immunoglobulin enhancer deletions in murine plasmacytomas," The EMBO Journal, 1985, vol. 4 (13B), pp. 3689-3693.

Ahmed T., "Sanofi-aventis and Regeneron Extend Therapeutic Antibody Agreement," PharmaDeals Review, Nov. 2009, vol. 11, p. 115.

Aizenshtein E., et al., "Immunological complex for enhancement of innate immune response in passive vaccination," Vaccine, Jan. 2013, vol. 31 (4), pp. 626-631 [abstract only—1 page].

An Z., "Therapeutic Monoclonal Antibodies from Bench to Clinic", 2009, 4 pages.

Anderson P.S. et al., "Extensive restrictions in the VH sequence usage of the human antibody response against the Rhesus D Antigen," Molecular Immunology, Jan. 2007, vol. 44, pp. 412-422.

Arnaout R., et al., "High-Resolution Description of Antibody Heavy-Chain Repertoires in Humans," PLoS One, Aug. 2011, vol. 6 (8), pp. e22365-1-e22365-8.

Arthur J.S.C., et al., "Gene-Targeting Vectors," Transgenesis Techniques, Principles and Protocols, Third edition, Chapter 9, 2009 (24 pages, including cover sheet, copyright and preface pages and table of contents), pp. 127-144.

Asenbauer H., et al., "The immunoglobulin lambda light chain enhancer consists of three modules which synergize in activation of transcription," European Journal of Immunology, 1999, vol. 29, pp. 713-724.

Askew G.R., et al., "Site-Directed Point Mutations in Embryonic Stem Cells: A Gene-Targeting Tag-and-Exchange Strategy," Molecular and Cellular Biology, Jul. 1993, vol. 13 (7), pp. 4115-4124.

Atlas of Genetics and Cytogenetics in Oncology and Haematology, VPREB1 (pre-B lymphocyte 1), 5 pages. [Retrieved online at http://atlasgeneticsoncolgy.org/Genes/GC_VPREB1.html on May 25, 2015].

Auerbach W., et al., "Establishment and Chimera Analysis of 129/SvEv- and C57BL/6-Derived Mouse Embryonic Stem Cell Lines," BioTechniques, 2000, vol. 29 (5), pp. 1024-1032.

Australian IP Office, Catriona Bruce, Examiner, Examination Report No. 1 for Standard Patent Application for Application No. 2016244295, dated Aug. 18, 2017, 4 pages.

Australian IP Office, Notification of material filed by a third-party for Application No. 2012311288 in the name of Kymab Ltd., Applicant, dated Nov. 20, 2017, 14 pages.

Avery S., Attorney for Applicant, Third-Party Pre-Issuance Submission Under 37 CFR Section 1.290 in U.S. Appl. No. 14/517,755, dated Jun. 26, 2015, 16 pages.

Baer A., et al., "Coping with kinetic and thermodynamic barriers: RMCE, an efficient strategy for the targeted integration of transgenes," Current Opinions in Biotechnology, Oct. 2001, vol. 12 (5), pp. 473-480.

Baker A.M., et al., "Adaptation of TCR Expression Vectors for the Construction of Mouse-Human Chimeric MBP-Specific TCR Transgenes," Journal of Neuroscience Research, 1996, vol. 45 (4), pp. 487-491.

Baker M.D., et al., "Homologous Recombination Between Transferred and Chromosomal Immunoglobulin Kappa Genes," Molecular and Cellular Biology, Oct. 1988, vol. 8 (10), pp. 4041-4047.

Balbás P., et al., "Chromosomal Editing in *Escherichia coli*. Vectors for DNA Integration and Excision," Molecular Biotechnology, Sep. 2001, vol. 19(1), pp. 1-12.

Barreto V.M., et al., "AID from bony fish catalyzes class switch recombination," Journal of Experimental Medicine, 2005, vol. 202 (6), pp. 733-738.

Bates J.G., et al., "Chromosomal Position of A VH Gene Segment Determines its Activation and Inactivation as a Substrate for V(D)J Recombination," Journal of Experimental Medicine, Dec. 2007, vol. 204 (13), pp. 3247-3256.

Baxendale H.E., et al., "Natural human antibodies to pneumococcus have distinctive molecular characteristics and protect against pneumococcal disease," Clinical and Experimental Immunology, 2007, vol. 151, pp. 51-60.

Beard C., et al., "Efficient Method to Generate Single-Copy Transgenic Mice by Site-Specific Integration in Embryonic Stem Cells," Genesis, 2006, vol. 44 (1), pp. 23-28.

Beck E., et al., "Nucleotide Sequence and Exact Localization of the Neomycin Phosphotransferase Gene From Transposon Tn5," Genesis, 1982, vol. 19 (3), pp. 327-336.

Beck J.A., et al., "Genealogies of mouse inbred strains," Nature Genetics, 2000, vol. 24, pp. 23-25 (with supporting table and chart).

Beerli R.R., et al., "Mining Human Antibody Repertoires," mAbs, Jul./Aug. 2010, vol. 2 (4), pp. 365-378.

Bentham A., J.A. Kemp, European Patent Attorney, Final Written Submissions for Application No. 12171793.8, dated May 17, 2018, 20 pages.

Bentham A., J.A. Kemp, European Patent Attorney, Statement of Fact and Arguments in Support of Opposition against EP2517557 in the name of Kymab Limited pertaining to Application No. 12171793.8, dated Jan. 11, 2017, 39 pages.

Bentham, A., Attorneys for Regeneron Pharmaceuticals, Inc., Opposition against EP2421357B1 in the name of Kymab Ltd. pertaining to Application No. 10734546.4, dated Jan. 9, 2017, 13 pages.

Berg D.E., et al., "Inverted Repeats of Tn5 are Transposable Elements," Proceedings of the National Academy of Sciences U.S.A, 1982, vol. 79 (8), pp. 2632-2635.

Bethke B., et al., "Segmental Genomic Replacement by Cre-Mediated Recombination: Genotoxic Stress Activation of the p53

(56)          References Cited

OTHER PUBLICATIONS

Promoter in Single-Copy Transformants," Nucleic Acids Research, 1997, vol. 25 (14), pp. 2828-2834.

Betz A.G., et al., "Elements Regulating Somatic Hypermutation of an Immunoglobulin ? Gene: Critical Role for the Intron Enhancer/Matrix Attachment Region," Cell, Apr. 1994, vol. 77, pp. 239-248.

Bhattacharya P., et al., "Switch Region Identity Plays an Important Role in Ig Class Switch Recombination," Journal of Immunology, 2010, vol. 184 (11), pp. 6242-6248.

Billiard F., et al., "Ongoing Dll4-Notch Signaling is Required for T-Cell Homeostasis in the Adult Thymus," European Journal of Immunology, 2011, vol. 41 (8), pp. 2207-2216.

Birling M.C., et al., "Site-Specific Recombinases for Manipulation of the Mouse Genome," Transgenesis Techniques, Principles and Protocols, Third edition, Chapter 16, 2009 (25 pages, including cover sheet, copyright and preface pages and table of contents), pp. 245-263.

Blankenstein T., et al., "Immunoglobulin VH Region Genes of the Mouse are Organized in Overlapping Clusters," European Journal of Immunology, 1987, vol. 17 (9), pp. 1351-1357.

Board of Appeal of the European Patent Office, Datasheet for the Decision of Nov. 9, 2015 for Application No. 02709544.7, Case T 2220/14-3.3.08, 83 pages.

Bode J., et al., "The Transgeneticist's Toolbox: Novel Methods for The Targeted Modification of Eukaryotic Genomes," Biological Chemistry, Sep./Oct. 2000, vol. 381 (9-10), pp. 801-813.

Bogen B., et al., "A Rearranged ?2 Light Gene Chain Retards but does not Exclude x and ?1 Expression," European Journal of Immunology, 1991, vol. 21 (10), pp. 2391-2395.

Bolland D.J., et al., "Antisense Intergenic Transcription Precedes Igh D-To-J Recombination and is Controlled by the Intronic Enhancer Eμ," Molecular and Cellular Biology, 2007, vol. 27 (15), pp. 5523-5533.

Bonin A., et al., "Isolation, Microinjection, and Transfer of Mouse Blastocysts," Methods in Molecular Biology, Chapter 9, 2001, vol. 158, pp. 121-134.

Bornstein G.G. et al., "Development of a new fully human anti-CD20 monoclonal antibody for the treatment of B-cell malignancies", Investigational New Drugs, 2010, vol. 28, pp. 561-574.

Bostrom, J. et al., "Variants of the Antibody Herceptin That Interact with HER2 and VEGF at the Antigen Binding Site," Science, Mar. 2009, vol. 323, pp. 1610-1614.

Bottaro A., et al., "Deletion of the IgH Intronic Enhancer and Associated Matrix-Attachment Regions Decreases, but does not Abolish, Class Switching at the μ Locus," International Immunology, 1998, vol. 10 (6), pp. 799-806.

Boyd S.D., et al., "Individual Variation in the Germline Ig Gene Repertoire Inferred from Variable Region Gene Rearrangements," The Journal of Immunology, Jun. 2010, vol. 184 (12), pp. 6986-6992.

Bradley A., Declaration of Allan Bradley (commercial success), with exhibits, as submitted in U.S. Appl. No. 13/416,684, dated Feb. 12, 2015, 15 pages.

Bradley A., Declaration of Allan Bradley (mouse strain), with exhibits, as submitted in U.S. Appl. No. 13/416,684, dated Feb. 12, 2015, 68 pages.

Bradley A., Declarations of Allan Bradley (Tanamachi/Grosveld), as submitted in U.S. Appl. No. 13/416,684, 5 pages.

Bradley A., et al., "Formation of Germ-Line Chimaeras from Embryo-Derived Teratocarcinoma Cell Lines," Nature, 1984, vol. 309 (5965), pp. 255-256.

Bradley A., et al., "Modifying the Mouse: Design and Desire," Biotechnology, May 1992, vol. 10(5), pp. 534-539.

Bradshaw, et al., "Handbook of Cell Signalling," 2010, Chapter 5, p. 33 (excerpt).

Bransteitter R., et al., "Activation-Induced Cytidine Deaminase Deaminates Deoxycytidine on Single-Stranded DNA but Requires the Action of RNase," Proceedings of the National Academy of Sciences of the U.S.A., Apr. 2003, vol. 100 (7), pp. 4102-4107.

Brault V., et al., "Modeling Chromosomes in Mouse to Explore the Function of Genes, Genomic Disorders, and Chromosonal Organization," PLoS Genetics, Jul. 2006, vol. 2 (7), pp. e86-1-e86-9.

Brazilian Patent Office, Lucia Aparecida Mendonca, Preliminary Office Action (English translation) for Application No. BR112012000536-7, dated Jul. 7, 2010, 1 page.

Brazilian Patent Office, Lucia Aparecida Mendonca, Preliminary Office Action for Application No. BR112012000536-7, dated Jul. 7, 2010, 12 pages.

Breden F., et al., "Comparison of Antibody Repertoires Produced by HIV-1 Infection, Other Chronic and Acute Infections, and Systemic Autoimmune Disease," PLoS One, 2011, vol. 6 (3), pp. e16857-1-e16857-11.

Brezinschek H.P., et al., "Analysis of the Human VH Gene Repertoire," Journal of Clinical Investigation, 1997, vol. 99 (10), pp. 2488-2501.

Briney B.S., et al., "Human Peripheral Blood Antibodies with Long HCDR3s are Established Primarily at Original Recombination using a Limited Subset of Germline Genes," PLoS One, 2012, vol. 7 (5), pp. e36750-1-e36750-13.

Brocker C.N., et al., "Evolutionary Divergence and Functions of the ADAM and ADAMTS Gene Families," Human Genomics, 2009, vol. 4 (1), pp. 43-55.

Brüggemann M., "Human Antibody Expression in Transgenic Mice," Archivum Immunologiae et Therapia Experimentalis, 2001, vol. 49 (3), pp. 203-208.

Brüggemann M., "Human Monoclonal Antibodies from Translocus Mice," Molecular Biology of B Cells, Chapter 34, 2003, pp. 547-561.

Brüggemann M., "The Preparation of Human Antibodies from Mice Harbouring Human Immunoglobulin Loci," Transgenic Animals. Generation and Use, 1997, Chapter 58, Part IV, Section A, pp. 397-402 (including cover and copyright pages).

Brüggemann M., et al., "A Repertoire of Monoclonal Antibodies with Human Heavy Chains from Transgenic Mice," Proceedings of the National Academy of Sciences U.S.A, 1989, vol. 86 (17), pp. 6709-6713.

Brüggemann M., et al., "Human Antibody Production in Transgenic Mice: Expression from 100 Kb of the Human IgH Locus," European Journal of Immunology, May 1991, vol. 21 (5), pp. 1323-1326.

Brüggemann M., et al., "Immunoglobulin Heavy Chain Locus of the Rat: Striking Homology to Mouse Antibody Genes," Proceedings of the National Academy of Sciences U.S.A, 1986, vol. 83 (16), pp. 6075-6079.

Brüggemann M., et al., "Selection Strategies III: Transgenic Mice," in Handbook of Therapeutic Antibodies—Technologies, Emerging Developments and Approved Therapeutics, 2010, Chapter 4, pp. 69-91.

Brüggemann M., et al., "Strategies for Expressing Human Antibody Repertoires in Transgenic Mice," Immunology Today, Aug. 1996, vol. 17 (8), pp. 391-397.

Brüggemann M., et al., "The Immunogenicity of Chimeric Antibodies," The Journal of Experimental Medicine, Dec. 1989, vol. 170 (6), pp. 2153-2157.

Buehr M., et al., "Capture of Authentic Embryonic Stem Cells from Rat Blastocysts," Cell, 2008, vol. 135 (7), pp. 1287-1298.

Burton D.R., et al., "Antibody vs. HIV in a clash of evolutionary titans," Proceedings of the National Academy of Sciences of the U.S.A, Oct. 2005, vol. 102 (42), pp. 14943-14948.

Butler J.E., "Immunoglobulin Diversity, B-Cell and Antibody Repertoire Development in Large Farm Animals," Revue scientifique et technique (International Office of Epizootics), 1998, vol. 17 (7), pp. 43-70.

Cadiñanos J., et al., "Generation of an Inducible and Optimized PiggyBac Transposon System," Nucleic Acids Research, 2007, vol. 35 (12), pp. e87.

Calame K., et al., "Regulation of immunoglobulin gene transcription," Immunoglobulin Genes, 2nd edition, Chapter 18, 1995, pp. 397-422.

Call L.M., et al., "A Cre-lox recombination system for the targeted integration of circular yeast artificial chromosomes into embryonic stem cells," Human Molecular Genetics, 2000, vol. 9 (12), pp. 1745-1751.

(56) References Cited

OTHER PUBLICATIONS

Camboni M., et al., "Active and passive immunization strategies based on the SDPM1 peptide demonstrate pre-clinical efficacy in the APPswePSEN1dE9 mouse model for Alzheimer's disease," Neurobiology of Disease, Feb. 2014, vol. 52, pp. 31-43 [abstract only—2 pages].

Canadian IP Office, Examiner A. Abdallah, Office Action for Application No. 2,857,569, dated Jan. 14, 2019, 6 pages.

Canadian IP Office, Protest and Submission of Prior Art, Application No. 2,802,591, dated Nov. 13, 2019, 18 pages.

Carpenter A.J., et al., "Construction, Characterization, and Complementation of a Conditional-Lethal DNA Topoisomerase IIalpha Mutant Human Cell Line," Molecular Biology of the Cell, Dec. 2004, vol. 15(12), pp. 5700-5711.

Carstea A.C., et al., "Germline Competence of Mouse ES and iPS Cell Lines: Chimera Technologies and Genetic Background," World Journal of Stem Cells, 2009, vol. 1 (1), pp. 22-29.

Carter T.C., et al., "Standardized Nomenclature for Inbred Strains of Mice," Cancer Research, 1952, vol. 12 (8), pp. 602-613.

Casrouge A., et al., "Size Estimate of the aBTCR Repertoire of Naive Mouse Splenocytes," The Journal of Immunology, 2000, vol. 164 (11), pp. 5782-5787.

Chan A.C., et al., "Therapeutic Antibodies for Autoimmunity and Inflammation," Nature Reviews Immunology, 2010, vol. 10 (5), pp. 301-316.

Chapal, N. et al., "Thyroid Peroxidase Autoantibodies Obtained from Random Single Chain Fv Libraries Contain the Same Heavy/Light Chain Combinations as Occur in Vivo," Endocrinology, 2001, vol. 142(11), pp. 4710-4750.

Chen C., et al., "Immunoglobulin Heavy Chain Gene Replacement: A Mechanism of Receptor Editing," Immunity, 1995, vol. 3 (6), pp. 747-755.

Chen J., et al., "B Cell Development in Mice that Lack One or Both Immunoglobulin K Light Chain Genes," The EMBO Journal, 1993, vol. 12 (3), pp. 821-830.

Chen Y., "PiggyBac Transposon-Mediated, Reversible Gene Transfer in Human Embryonic Stem Cells," Stem Cells and Development, Nov. 2010, vol. 19 (6), 9 pages.

Chia R., et al., "The origins and uses of mouse outbred stocks," Nature Genetics, 2005, vol. 37 (11), pp. 1181-1186.

Chinese Patent Office, First Office Action (English translation) for Application No. 201610821299.6, dated Jun. 23, 2020, 19 pages.

Chinese Patent Office, First Office Action (English Translation) for Chinese Application No. 201180039668.1, dated Jan. 3, 2014, 6 pages.

Chinese Patent Office, First Office Action for Application No. 201610821299.6, dated Jun. 23, 2020, 15 pages.

Chinese Patent Office, First Office Action for Chinese Patent Application No. 201180039668.1, dated Jan. 3, 2014, 6 pages.

Chinese Patent Office, Office Action (English Translation) for Chinese Patent Application No. 201380029744.1, dated Nov. 10, 2016, 2 pages.

Chinese Patent Office, Office Action for Chinese Patent Application No. 201380027944.1, dated Nov. 10, 2016, 5 pages.

Oancea A.E., et al., "Expression of the (recombinant) Endogenous Immunoglobulin Heavy-Chain Locus Requires the Intronic Matrix Attachment Regions," Molecular and Cellular Biology, 1997, vol. 17 (5), pp. 2658-2668.

Oberdoerffer P., et al., "Unidirectional Cre-Mediated Genetic Inversion in Mice using the Mutant loxP Pair lox66/lox71," Nucleic Acids Research, 2003, vol. 31 (22), pp. e140-1-e140-7.

Ogle, Ph.D., J.M., European Patent Attorney of Hoffman Eitle, Opposition to EP 2792236 (Application No. 14176740.0) dated Feb. 28, 2020, 56 pages.

Ogle, Ph.D., J.M., European Patent Attorney of Hoffman Eitle, Reply to Patentee's Response of Nov. 16, 2018 In Re Opposition against EP 3028564 (European Appln. No. 16151214.0), dated Feb. 12, 2019, 28 pages.

Ogle, Ph.D., J.M., European Patent Attorney of Hoffman Eitle, Reply to Statement of Grounds of Appeal (Corrected version) In re Opposition against EP2758535 dated Feb. 26, 2020, 83 pages.

Ogle, Ph.D., J.M., European Patent Attorney of Hoffman Eitle, Reply to Statement of Grounds of Appeal In re Opposition against EP2758535 dated Feb. 26, 2020, 80 pages.

Ogle, Ph.D., J.M., European Patent Attorney of Hoffman Eitle, Subsequent Written Submission in Response to Patentee's Written Submissions of Jan. 10, 2020 and Jan. 27, 2020 In Re Opposition against EP 3028564 (European Appln. No. 16151214.0), dated Feb. 11, 2020, 10 pages.

Ogle, Ph.D., J.M., European Patent Attorney of Hoffman Eitle, Written Submission in preparation to/during oral proceedings In re Opposition against EP2792236 dated Apr. 17, 2020, 14 pages.

Ohlin M., et al., "The Human Antibody Repertoire to Infectious Agents: Implications for Disease Pathogenesis," Molecular Immunology, 2003, vol. 40 (1), pp. 1-11.

Ohm-Laursen L., et al., "Identification of Two New Alleles, IGHV3-23*04 and IGHJ6*04, and the Complete Sequence of the IGHV3-h Pseudogene in the Human Immunoglobulin Locus and their Prevalences in Danish Caucasians," Immunogenetics, 2005, vol. 57 (9), pp. 621-627.

Okada A., et al., "The variable region gene assembly mechanism," Immunoglobulin Genes, 2nd edition, Chapter 10, 1995, pp. 205-234.

Osborn M.J., et al., "High-Affinity IgG Antibodies Develop Naturally in Ig-Knockout Rats Carrying Germline Human IgH/IgV/IgV Loci Bearing the Rat CH Region," Journal of Immunology, 2013, vol. 190 (4), pp. 1481-1490.

Osoegawa K., et al., "Bacterial Artificial Chromosome Libraries for Mouse Sequencing and Functional Analysis," Genome Research, 2000, vol. 10 (1), pp. 116-128.

Osterroth, F., et al., "Rapid expression cloning of human immunoglobulin Fab fragments for the analysis of antigen specificity of B cell lymphomas and anti-idiotype lymphoma vaccination," Journal of Immunological Methods 1999, vol. 229, pp. 141-153.

Oumard A., et al., "Recommended method for chromosome exploitation: RMCE-based cassette-exchange systems in animal cell biotechnology," Cytotechnology, 2006, vol. 50, pp. 93-108.

Ozawa T., et al., "Amplification and analysis of cDNA generated from a single cell by 5'-RACE: application to isolation of antibody heavy and light chain variable gene sequences from single B cells,," BioTechniques—Short Technical Reports, 2006, vol. 40, Issue No. 4, pp. 469-478.

Parng C.L., et al., "Gene Conversion Contributes to Ig Light Chain Diversity in Cattle," Journal of Immunology, 1996, vol. 157 (12), pp. 5478-5486.

Patil V.M., et al., "Transgenic animals and drug development: A review," Indian Journal of Public Health Research & Development, Jun. 2011, vol. 2, Issue No. 1, pp. 106-109.

Pavlicek A., et al., "Ancient Transposable Elements, Processed Pseudogenes, and Endogenous Retroviruses," Genomic Disorders, Chapter 4, 2006, pp. 57-72.

Pear W.S., et al., "Localization of the Rat Immunoglobulin Heavy Chain Locus to Chromosome 6," Immunogenetics, 1986, vol. 23 (6), pp. 393-395.

Pelham H., et al., "Expression of a Drosophila Heat Shock Protein in Mammalian Cells: Transient Association with Nucleoli After Heat Shock," Philosophical Transactions of the Royal Society B: Biological Sciences, 1984, vol. 307 (1132), pp. 301-307.

Pera M.F., et al., "Human embryonic stem cells," Journal of Cell Science, 2000, vol. 113, pp. 5-10.

Perera, W.S., et al., "Comparison between hybridoma and Fab/phage anti-RhD: Their V gene usage and pairings," Disease Markers, 2000, vol. 16, pp. 15-19.

Perlot T., et al., "Antisense Transcripts from Immunoglobulin Heavy-Chain Locus V(D)J and Switch Regions," Proceedings of the National Academy of Sciences of the U.S.A., 2008, vol. 105 (10), pp. 3843-3848.

Perlot T., et al., "Cis-Regulatory Elements and Epigenetic Changes control genomic rearrangements of the IgH locus," Advances in Immunology, Chapter 1, 2008, vol. 99, pp. 1-32.

(56) References Cited

OTHER PUBLICATIONS

Persic, L., et al., "An integrated vector system for the eukaryotic expression of antibodies or their fragments after selection from phage display libraries," Gene 1997, vol. 187, pp. 9-18.
Pettersson S., et al., "A second B cell-specific enhancer 3' of the immunoglobulin heavy-chain locus," Nature, Mar. 1990, vol. 344, pp. 165-168.
Pettitt S.J., et al., "Agouti C57BL/6N Embryonic Stem Cells for Mmouse Genetic Resources," Nature Methods, 2009, vol. 6 (7), pp. 493-495.
Pinaud E., et al., "The IgH Locus 3' Regulatory Region: Pulling the Strings from Behind," Advances in Immunology, Chapter 2, 2011, vol. 11, pp. 27-70.
Plasterk R.H., et al., "Resident Aliens: the Tc1/Mariner Superfamily of Transposable Elements," Trends Genetics, 1999, vol. 15(8), pp. 326-332.
Ploegh, Hidde Dr., Declaration, submittted in U.S. Appl. No. 14/046,291 (now U.S. Pat. No. 10,526,630) dated Jul. 12, 2018, 123 pages.
Pobursky K., Third-Party Pre-Issuance Submission Under 37 CFR 1.290 in U.S. Appl. No. 13/433,084, dated Apr. 1, 2014, 15 pages.
Pobursky K., Third-Party Pre-Issuance Submission Under 37 CFR 1.290 in U.S. Appl. No. 13/434,361, dated Apr. 1, 2014, 15 pages.
Pobursky K., Third-Party Pre-Issuance Submission Under 37 CFR 1.290 in U.S. Appl. No. 13/740,727, dated May 27, 2014, 25 pages.
Pobursky K., Third-Party Pre-Issuance Submission Under 37 CFR 1.290 in U.S. Appl. No. 13/843,528, dated Mar. 18, 2014, 14 pages.
Ponsel D., et al., "High Affinity, Developability and Functional Size: the Holy Grail of Combinatorial Antibody by Library Generation," Molecules, 2011, vol. 16 (5), pp. 3675-3700.
Popov A.V., et al., "A Human Immunoglobulin ? Locus is Similarly Well Expressed in Mice and Humans," The Journal of Experimental Medicine, 1999, vol. 189 (10), pp. 1611-1620.
Porter A., Resume Imperial College London, retrieved from the Internet under https://www.imperial.ac.uk/people/andy porter on May 21, 2020, 2 pages.
Porter A.C., et al., "Role of the B Subunit of the *Escherichia coli* Proton-Translocating ATPase. A Mutagenic Analysis," Journal of Biological Chemistry, Jul. 1985, vol. 260(13), pp. 8182-8187.
Porter, Andrew, Declaration (Evidence in Support of Opposition thereto by Regeneron Pharmaceuticals, Inc. for EP Patent No. 2517556B1), dated Oct. 11, 2018, 31 pages.
Porter, Andrew, Declaration for Kymab, Ltd. relating to Patent No. EP 2,792,236 B1, dated Aug. 10, 2018, 24 pages.
Porter, Andrew, Second Declaration (Evidence in Support of Opposition thereto by Regeneron Pharmaceuticals, Inc. for EP Patent No. 2792236B1), dated Apr. 14, 2020, 8 pages.
Porteus M., "Using Homologous Recombination to Manipulate the Genome of Human Somatic Cells," Biotechnology and Genetic Engineering Reviews, 2007, vol. 24, pp. 195-212.
Potter K.N., et al., "Features of the overexpressed V1-69 genes in the unmutated subset of chronic lymphocytic leukemia are distinct from those in the healthy elderly repertoire," Blood, Apr. 2003, vol. 101 (8), pp. 3082-3084.
Prak E.T.L, et al., "B cell receptor editing in tolerance and autoimmunity," Annals of the New York Academy of Sciences, Jan. 2011, vol. 1217, pp. 96-121.
Pramanik S., et al., "Segmental Duplication as One of the Driving Forces Underlying the Diversity of the Human Immunoglobulin Heavy Chain Variable Gene Region," BMC Genomics, Jan. 2011, vol. 12 (78), 12 pages.
Presta L., "Molecular engineering and design of therapeutic antibodies," Current Opinion in Immunology, 2008, vol. 20, pp. 460-470.
Primakoff P., et al., "Penetration, Adhesion, and Fusion in Mammalian Sperm-Egg Interaction," Science, 2002, vol. 296 (5576), pp. 2183-2185.
Primakoff P., et al., "The ADAM Gene Family: Surface Proteins with Adhesion and Protease Activity," Trends Genetics, 2000, vol. 16 (2), pp. 83-87.

Printout of PDF file available from the University of California website presented in support of European opposition in the name of Kymab Ltd. pertaining to Application No. EP12171793.8 as filed on Jan. 19, 2017, 4 pages. [http://www.research.uci.edu/facilities-services/tmf/presentations/Mouse_ES_CellLine].
HGNC (Hugo Gene Nomenclature Committee), "Gene Family: Immunoglobulin Heavy Locus at 14q32.33 (IGH)," 4 pages. [retrieved on Jul. 31, 2017 at http://www.genenames.org/cgi-bin/genefamilies/set/349].
Hjelm B., et al., "Generation of monospecific antibodies based on affinity capture of polyclonal antibodies," Protein Science, 2011, vol. 20, pp. 1824-1835.
Hohn B., et al., "Elimination of selection markers from transgenic plants," Current Opinion in Biotechnology, Plant biotechnology, 2001, vol. 12, pp. 139-143.
Hong J., et al., "Derivation and Characterization of Embryonic Stem Cells Lines Derived from Transgenic Fischer 344 and Dark Agouti Rats," Stem Cells and Development, 2012, vol. 21 (6), pp. 1571-1586.
Houdebine L.M., "The Methods to Generate Transgenic Animals and to Control Transgene Expression," Journal of Biotechnology, 2002, vol. 98 (2-3), pp. 145-160.
Houdebine L.M., "Transgenic Animal Models in Biomedical Research," Methods in Molecular Biology, Chapter 10, 2007, vol. 360, pp. 163-202.
Houldsworth J., et al., "Comparative Genomic Hybridization: An Overview," The American Journal of Pathology, Dec. 1994, vol. 145 (6), pp. 1253-1260.
Hisu E., et al., "The plasticity of immunoglobulin gene systems in evolution," Immunology Reviews, vol. 210, Apr. 2006, pp. 8-26.
Huang C., et al., "Structural Basis of Tyrosine Sulfation and VH-Gene Usage in Antibodies that Recognize the HIV Type 1 Coreceptor-Binding Site on gp120," Proceedings of the National Academy of Sciences of the U.S.A., 2004, vol. 101 (9), pp. 2706-2711.
Huang D., et al., "Sequence Analyses of Three Immunoglobulin G Anti-virus Antibodies Reveal Their Utilization of Autoantibody-related Immunoglobulin Vh Genes, but Not Vλ Genes," Journal of Clinical Investigations, Dec. 1992, vol. 90, pp. 2197-2208.
Huber V.C., et al., "Distinct Contributions of Vaccine-Induced Immunoglobulin G1 (IgG1) and IgG2a Antibodies to Protective Immunity Against Influenza," Clinical and Vaccine Immunology, 2006, vol. 13 (9), pp. 981-990.
Hudziak R.M., et al., "Establishment of Mammalian Cell Lines Containing Multiple Nonsense Mutations and Functional Suppressor tRNA Genes," Cell, 1982, vol. 31 (1), pp. 137-146.
Huovila A.J., et al., "Shedding Light on ADAM Metalloproteinases," Trends in Biochemical Sciences, 2005, vol. 30 (7), pp. 413-422.
Hülseweh B., et al., "Human-like antibodies neutralizing Western equine encephalitis virus," mAbs, May/Jun. 2014, vol. 6 (3), pp. 718-727.
Ichihara Y., et al., "Organization of Human Immunoglobulin Heavy Chain Diversity Gene Loci," The EMBO Journal, 1988, vol. 7, No. 13, pp. 4141-4150.
Iglesias-Ussel M.D., et al., "Forced Expression of AID Facilitates the Isolation of Class Switch Variants from Hybridoma Cells," Journal of Immunological Methods, 2006, vol. 316 (1-2), pp. 59-66.
Ignatovich O. et al., "The creation of diversity in the human immunoglobulin V(lambda) repertoire," Journal of Molecular Biology, Apr. 1997, vol. 268, pp. 69-77.
Ignatovich O., et al., "Dominance of intrinsic genetic factors in shaping the human immunoglobulin V? repertoire", Journal of Molecular Biology, Nov. 1999, vol. 294, pp. 457-465.
Imbimbo B.P., et al., "Solanezumab for the treatment of mild-to-moderate Alzheimer's disease," Expert Review of Clinical Immunology, Feb. 2012, vol. 8 (2), pp. 135-149 [abstract only—1 page].
IMGT, the International ImMunoGeneTics Information system database, "Alignment of alleles: Human IGHJ6," dated Jun. 29, 2011, 1 page.
IMGT, the International ImMunoGeneTics Information system database, IMGT/GENE-DB entry for *Homo sapiens* IGHD3-9, 2007, 2 pages.

(56)     References Cited

OTHER PUBLICATIONS

IMGT, the International ImMunoGeneTics Information system database, IMGT/GENE-DB entry for *Homo sapiens* IGHJ6, dated Jul. 26, 2017, version 3.1.17, 4 pages.
IMGT, the International ImMunoGeneTics Information system database, "IMGT/GENE-DB reference sequences," Amino acid sequences of the four human IGHJ6 alleles, dated Jul. 26, 2017, version 3.1.17, 7 pages.
IMGT, the International ImMunoGeneTics Information system database, "IMGT/GENE-DB reference sequences," Nucleotide sequences of the four human IGHJ6 alleles, dated Jul. 26, 2017, version 3.1.17, 1 page.
International Bureau of WIPO, Third-Party Observations regarding Application No. PCT/EP2018/068309, dated Aug. 14, 2019, 6 pages.
Itzhaki J.E., et al., "Construction by Gene Targeting in Human Cells of a Conditional CDC2 Mutant That Rereplicates Its DNA,", Nature Genetics, Mar. 1997, vol. 15(3), pp. 258-265.
Itzhaki J.E., et al., "Targeted Breakage of a Human Chromosome Mediated by Cloned Human Telomeric DNA," Nature Genetics, Dec. 1992, vol. 2(4), pp. 283-287.
Ivanov I.I., et al., "Development of the Expressed Ig CDR-H3 Repertoire Is Marked by Focusing of Constraints in Length, Amino Acid Use, and Charge That Are First Established in Early B Cell Progenitors," The Journal of Immunology, Jun. 2005, vol. 174, pp. 7773-7780.
Ivcs Z., et al., "The Expanding Universe of Transposon Technologies for Gene and Cell Engineering," Mobile DNA, 2010, vol. 1 (1), 15 pages.
Ivcs Z., et al., "The Sleeping Beauty Transposable Element: Evolution, Regulation and Genetic Applications," Current Issues in Molecular Biology, 2004, vol. 6 (1), pp. 43-55.
Ivcs Z., et al., "Transposon-mediated genome manipulation in vertebrates," Nature Methods, Jun. 2009, vol. 6, Issue No. 6, pp. 415-422 (including Errata sheet).
Izsvák Z., et al., "Sleeping Beauty Transposition: Biology and Applications for Molecular Therapy," Molecular Therapy, 2004, vol. 9 (2), pp. 147-156.
Jackson S.M., et al., "Human B Cell Subsets," Advances in Immunology, Chapter 5, 2008, vol. 98, pp. 151-224.
Jacob H.J., et al., "Gene Targeting in the Rat: Advances and Opportunities," Trends in Genetics, 2010, vol. 26 (12), pp. 510-518.
Jakobovits A., "Production of Fully Human Antibodies by Transgenic Mice," Current Opinion in Biotechnology, 1995, vol. 6 (5), pp. 561-566.
Jakobovits A., "The Long-Awaited Magic Bullets: Therapeutic Human Monoclonal Antibodies from Transgenic Mice," Expert Opinion Investigational Drugs, 1998, vol. 7 (4), pp. 607-614.
Jakobovits A., et al., "From XenoMouse Technology to Panitumumab, the First Fully Human Antibody Product from Transgenic Mice," Nature Biotechnology, 2007, vol. 25 (10), pp. 1134-1143.
Janeway C.A. et al., "Structure of the Antibody Molecule and the Immunoglobulin Genes," excerpts from Immunobiology: The Immune System in Health and Disease, 4th Edition, 1999, 4 pages.
Janeway C.A. et al., "The rearrangement of antigen-receptor gene segments controls lymphocyte development," Immunobiology: The Immune System in Health and Disease, 5th Edition, 2001, 13 pages. [Retrieved from the Internet: http://www.ncbi.nlm.nih.gov/books/NBK27113/].
Janeway, et al., "Structural variation in Immunoglobulin Constant Regions," Immunobiology: The Immune System in Health and Disease, 5th Edition, 2001, 5 pages.
Janssens R., et al., "Generation of Heavy-Chain-only Antibodies in Mice," Proceedings of the National Academy of Sciences of the U.S.A., 2006, vol. 103 (41), pp. 15130-15135.
Japanese Patent Office, Decision of Rejection—Application No. 2017-021028, mailed Sep. 9, 2019, together with English translation, 9 pages.
Japanese Patent Office, Pre-Appeal Report—Application No. 2017-021028—Appeal No. 2020-000300, mailed Mar. 17, 2020, together with English translation, 13 pages.
Japanese Patent Office, Notice of Reasons for Rejection—Application No. 2016-548441, mailed Aug. 5, 2019, together with English translation, 12 pages.
Japanese Patent Office, Notice of Reasons for Rejection—Application No. 2018-088749, mailed May 27, 2019, together with English translation, 11 pages.
Japanese Patent Office, Notice of Reasons for Rejection—Application No. 2021-026065, mailed Mar. 22, 2022, together with English translation, 16 pages.
Japanese Patent Office, Notice of Reasons for Rejection—Application No. 2017-021028, mailed Dec. 21, 2018, together with English translation, 11 pages.
Japanese Patent Office, Notice of Reasons for Rejection—Application No. 2020-500127, mailed May 30, 2022, together with English translation, 13 pages.
Japanese Patent Office, Notice of Reasons for Rejection—Application No. 2017-017360, mailed Mar. 19, 2018, together with English translation, 7 pages.
Jasper, P.J., et al., "B lymphocyte deficiency in IgH-transgenic rabbits," European Journal of Immunology, 2007, vol. 37, pp. 2290-2299.
[No Author Listed] Exemplary allele distribution for IgHV3-72 (3 pages) [retrieved from the internet Apr. 29, 2021: http://www.imgt.org/IMGTrepertoire/Proteins/taballeles/human/IGH/IGHV/Hu_IGHVall.html].
[No Author Listed] Exemplary allele distribution for IgHV3-73 (3 pages) [retrieved from the internet Apr. 29, 2021: http://www.imgt.org/IMGTrepertoire/Proteins/taballeles/human/IGH/IGHV/Hu_IGHVall.html].
[No Author Listed] IMGT Repertoire (IG and TR), Gene table: human (*Homo sapiens*) IGHJ4, created Oct. 17, 1997, last updated Mar. 30, 2021, 606 pages. [retrieved from the internet under: http://www.imgt.org/IMGTrepertoire/Proteins/alleles/index.php?species=Homo%20sapiens&group=IGHJ&gene=IGHJ4].
[No Author Listed] Imgt Repertoire (IG and TR), Locus representation: Human (*Homo sapiens*) IGK, dated Nov. 26, 2021, 3 pages [retrieved from the internet under: http://www.imgt.org/IMGrepertoire/index.php?section=LocusGenes&repertoire=locus&species=human&group=IGK/].
[No Author Listed] IMGT Repertoire, Gene table: Protein display: Human IGH C-Regions, last updated Jun. 9, 2021, 1 page [retrieved from the internet under: http://www.imgt.org/IMGTrepertoire/Proteins/protein/human/IGH/IGHC/Hu_IGHCallgenes.html].
Almagro J.C., et al., "Therapeutic Monoclonal Antibodies from Bench to Clinic, " Part IV—Antibody Engineering, Chapter 13: Antibody Engineering: Humanization, Affinity Maturation, and Selection Techniques, 2009, pp. 311-334, including cover and copyright pages, Edited by Zhiqiang An, John Wiley & Sons, Inc., ISBN 978-0-470-11791-0 [retrieved online: https://doi.org/10.1002/9780470485408.ch13].
Bergmann-Leitner, E., et al., "Evaluation of immunoglobulin purification methods and their impact on quality and yield of antigen-specific antibodies," Malaria Journal, 2008, vol. 7 (129), 10 pages.
Brevini T.A.L., et al., "Embryonic Stem Cells in Domestic Animals, No shortcuts to pig embryonic stem cells," ScienceDirect/Theriogenology, vol. 74, 2010, pp. 544-550.
Brezinschek H.P., et al., "Analysis of the Heavy Chain Repertoire of Human Peripheral B Cells Using Single-Cell Polymerase Chain Reaction," The Journal of Immunology, vol. 155, 1995, pp. 190-202.
Bychowski M.E., Third-Party Pre-Issuance Submission Under 37 CFR 1.290 in U.S. Appl. No. 17/020,997, dated Sep. 10, 2021, 66 pages.
Canadian IP Office, Protest and Submission of Prior Art, Application No. 2,767,436, dated Oct. 11, 2022, 13 pages.
Casadevall A., et al., "Serum Therapy Revisited: Animal Models of Infection and Development of Passive Antibody Therapy," Antimicrobial Agents and Chemotherapy, Aug. 1994, vol. 38, Issue No. 8, pp. 1695-1702.

(56) References Cited

OTHER PUBLICATIONS

Casadevall A., et al., "The convalescent sera option for containing COVID-19," The Journal of Clinical Investigation, 2020, vol. 130, Issue No. 4, pp. 1545-1548.

Chen J., et al., "RAG-2-deficient blastocyst complementation: An assay of gene function in lymphocyte development," Proceedings of the National Academy of Sciences of the U.S.A., Immunology, May 1993, vol. 90, pp. 4528-4532.

Ciudad, C., et al., "Deletion of Analysis of the Chinese Hamster Dihydrofolate Reductase Gene Promoter," The Journal of Biological Chemistry, 1988, vol. 263, No. 31, pp. 16274-16282.

Clark K.J., et al., "Pigs taking wing with transposons and recombinases," Genome Biology, 2007, vol. 8, Suppl. I, Article S13, 16 pages.

Collins, A., et al., "Immunoglobulin Light Chain Gene Rearrangements, Receptor Editing and the Development of a Self-Tolerant Antibody Repertoire," Frontiers in Immunology, 2018, vol. 9, pp. 1-12.

Daukss, Dana M., Third-Party Pre-Issuance Submission Under 37 CFR 1.290 in U.S. Appl. No. 16/721,326, dated Mar. 25, 2021, 30 pages (Second Submission).

Daukss, Dana M., Third-Party Pre-Issuance Submission Under 37 CFR 1.290 in U.S. Appl. No. 16/721,326, dated Mar. 25, 2021, 36 pages.

Daukss, Dana M., Third-Party Pre-Issuance Submission Under 37 CFR 1.290 in U.S. Appl. No. 16/869,416, dated Apr. 6, 2021, 28 pages.

Daukss, Dana M., Third-Party Pre-Issuance Submission Under 37 CFR 1.290 in U.S. Appl. No. 16/870,413, dated Jun. 1, 2021, 34 pages.

Daukss, Dana M., Third-Party Pre-Issuance Submission Under 37 CFR 1.290 in U.S. Appl. No. 16/870,413, dated Jun. 1, 2021, 40 pages (Second Submission).

Daukss, Dana M., Third-Party Pre-Issuance Submission Under 37 CFR 1.290 in U.S. Appl. No. 16/886,057, dated Apr. 1, 2021, 31 pages.

Daukss, Dana M., Third-Party Pre-Issuance Submission Under 37 CFR 1.290 in U.S. Appl. No. 16/886,394, dated Apr. 1, 2021, 33 pages.

Daukss, Dana M., Third-Party Pre-Issuance Submission Under 37 CFR 1.290 in U.S. Appl. No. 16/905,537, dated Apr. 23, 2021, 47 pages.

Daukss, Dana M., Third-Party Pre-Issuance Submission Under 37 CFR 1.290 in U.S. Appl. No. 17/180,258, dated Oct. 13, 2021, 52 pages.

Dictionary.com, Definition of "population" 2021, 8 pages [retrieved online: https://www.dictionary.com/browse/ population].

Dogan, I., et al., "Multiple layers of B cell memory with different effector functions" Nature Immunology 2009, vol. 10, No. 12, pp. 1292-1299.

Doyle A., et al., "The Construction of Transgenic and Gene Knockout/ Knockin Mouse Models of Human Disease," Transgenic Research, 2012, vol. 21 (2), pp. 327-349.

Durbin R., "A Map of Human Genome Variation from Population-Scale Sequencing," Nature, 1000 Genomes Project Consortium, 2010, vol. 467 (7319), pp. 1061-1073.

Durdik J., et al., "Isotype Switching by a Microinjected u Immunoglobulin Heavy Chain Gene in Transgenic Mice," Proceedings of the National Academy of Sciences of the U.S.A, 1989, vol. 86 (7), pp. 2346-2350.

Dörner T., et al., "Analysis of the targeting of the hypermutational machinery and the impact of subsequent selection on the distribution of nucleotide changes in human VHDJH rearrangements," Immunologic Reviews, Apr. 1998, vol. 162 (1), pp. 161-171.

Dörner T., et al., "Delineation of Selective Influences Shaping the Mutated Expressed Human Ig Heavy Chain Repertoire," The Journal of Immunology, Mar. 1998, vol. 160 (6), pp. 2831-2841.

Dörner T., et al., "Somatic hypermutation of human immunoglobulin heavy chain genes: targeting of RGYW motifs on both DNA strands," European Journal of Immunology, 1998, vol. 28, pp. 3384-3396.

Dübel S., "Therapeutic Antibodies—From Past to Future," in Handbook of Therapeutic Antibodies—Technologies, Emerging Developments and Approved Therapeutics, 2010, Chapter 1 (excerpt: pp. 3-5).

Ebersbach H., et al., "Antigen Presentation for the Generation of Binding Molecules," Methods of Molecular Biology, 2012, Chaper 1: Antigen Presentation for the Generation of Binding Molecules, 19 pages.

Ebert A., et al., "The Distal VH Gene Cluster of the Igh Locus Contains Distinct Regulatory Elements with Pax5 Transcription Factor-Dependent Activity in Pro-B Cells," Immunity, Feb. 2011, vol. 34 (2), pp. 175-187.

Edwards D.R., et al., "The ADAM Metalloproteinases," Molecular Aspects of Medicine, 2008, vol. 29 (5), pp. 258-289.

Eisen H.N., et al., "Variations in Affinities of Antibodies during the Immune Response," Biochemistry, Feb. 1964, vol. 3, Issue No. 7, pp. 996-1008.

Eisener-Dorman A.F., et al., "Cautionary Insights on Knockout Mouse Studies: The Gene or not the Gene?," Brain, Behavior, and Immunity, 2009, vol. 23 (3), pp. 318-324.

Ejima D., "Effective elution of antibodies by arginine and arginine derivatives in affinity column chromatography," Analytical Biochemistry, 2005, vol. 345, pp. 250-257.

Ekiert D.C., et al., "A Highly Conserved Neutralizing Epitope on Group 2 Influenza A Viruses," Science, 2011, vol. 333 (6044), pp. 843-850.

Engel H., et al., "Expression level of a transgenic ?2 chain results in isotype exclusion and commitment to B1 cells," European Journal of Immunology, 1998, vol. 28, pp. 2289-2299.

England, Nicholas Dr., 37 C.F.R. Rule 1.132 Declaration, dated Dec. 21, 2016, 6 pages.

European Patent Office, Alessandro Brero, Authorized officer, International Search Report for Application No. PCT/GB2012/052296, mailed on May 17, 2013, 30 pages, together with the Written Opinion of the International Searching Authority.

European Patent Office, Alessandro Brero, Authorized officer, International Search Report for Application No. PCT/GB2012/052297, mailed on Jun. 19, 2013, 24 pages, together with the Written Opinion of the International Searching Authority.

European Patent Office, Alessandro Brero, Authorized Officer, International Search Report for Application No. PCT/GB2012/052298, mailed on Jun. 13, 2013, 21 pages, together with the Written Opinion of the International Searching Authority.

European Patent Office, Examination Report for Application No. 12762378.3, dated Jun. 8, 2016, 5 pages.

European Patent Office, Extended European Search Report for Application No. 16189625.3, dated Nov. 23, 2016, 8 pages.

European Patent Office, Extended European Search Report for Application No. 20188009.3, dated May 3, 2021, 17 pages.

Jefferis R., et al., "Human immunoglobulin allotypes," mAbs, Jul./Aug. 2009, vol. 1, Issue No. 4, pp. 1-7.

Jendreyko N., et al., "Intradiabodies, Bispecific, Tetravalent Antibodies for the Simultaneous Functional Knockout of Two Cell Surface Receptors," The Journal of Biological Chemistry, 2003, vol. 278 (48), pp. 47812-47819.

Jessen K.A., et al., "Molecular Analysis of Metastasis in a Polyomavirus Middle T Mouse Model: the Role of Osteopontin," Breast Cancer Research, 2004, vol. 6 (3), pp. R157-R169.

Johnston C.M., et al., "Complete Sequence Assembly and Characterization of the C57BL/6 Mouse Ig Heavy Chain V Region," The Journal of Immunology, 2006, vol. 176 (7), pp. 4221-4234.

Jones B.T., Attorney for Applicant, Third-Party Pre-Issuance Submission Under 37 CFR Sec. 1.290 in U.S. Appl. No. 15/016,211, filed Oct. 4, 2016, 59 pages.

Jones B.T., Attorney for Applicant, Third-Party Pre-Issuance Submission Under 37 CFR Sec. 1.290 in U.S. Appl. No. 15/018,670, filed Aug. 12, 2016, 26 pages.

Jones B.T., Attorney for Applicant, Third-Party Pre-Issuance Submission Under 37 CFR Sec. 1.290 in U.S. Appl. No. 15/095,315, filed Sep. 16, 2016, 26 pages.

Jones B.T., Attorney for Applicant, Third-Party Pre-Issuance Submission Under 37 CFR Sec. 1.290 in U.S. Appl. No. 15/214,963, filed Mar. 2, 2017, 42 pages.

(56) References Cited

OTHER PUBLICATIONS

Jones B.T., Attorney for Applicant, Third-Party Pre-Issuance Submission Under 37 CFR Sec. 1.290 in U.S. Appl. No. 15/232,122, filed Mar. 13, 2017, 32 pages.

Jones B.T., Attorney for Applicant, Third-Party Pre-Issuance Submission Under 37 CFR Sec. 1.290 in U.S. Appl. No. 15/251,969, filed May 4, 2017, 22 pages.

Jones B.T., Attorney for Applicant, Third-Party Pre-Issuance Submission Under 37 CFR Sec. 1.290 in U.S. Appl. No. 15/360,502, filed May 8, 2017, 40 pages.

Jones B.T., Attorney for Applicant, Third-Party Pre-Issuance Submission Under 37 CFR Sec. 1.290 in U.S. Appl. No. 15/383,101, filed May 30, 2017, 32 pages.

Jones B.T., Attorney for Applicant, Third-Party Pre-Issuance Submission Under 37 CFR Sec. 1.290 in U.S. Appl. No. 15/383,188, filed May 30, 2017, 33 pages.

Jones B.T., Attorney for Applicant, Third-Party Pre-Issuance Submission Under 37 CFR Sec. 1.290 in U.S. Appl. No. 15/383,196, filed May 8, 2017, 25 pages.

Jones B.T., Attorney for Applicant, Third-Party Pre-Issuance Submission Under 37 CFR Sec. 1.290 in U.S. Appl. No. 15/383,202, filed May 3, 2017, 23 pages.

Jung D., et al., "Mechanism and Control of V(D)J Recombination at the Immunoglobulin Heavy Chain Locus," Annual Review of Immunology, 2006, vol. 24, pp. 541-570.

Kaji K., et al., "Virus-free induction of pluripotency and subsequent excision of reprogramming factors," Nature, Apr. 2009, vol. 458, pp. 771-776.

Kaminski D.A., et al., "Antibody Class Switching differs among SJL, C57BL/6 and 129 Mice," International Immunology, 2007, vol. 19 (4), pp. 545-556.

Karu A.E., et al., "Recombinant Antibody Technology," ILAR Journal / National Research Council, Institute of Laboratory Animal Resources, 1995, vol. 37 (3), pp. 132-141.

Kaushik A., et al., "Novel Insight into Antibody Diversification from Cattle," Veterinary Immunology and Immunopathology, 2002, vol. 87 (3-4), pp. 347-350.

Kawasaki K., et al., "One-Megabase Sequence Analysis of the Human Immunoglobulin A Gene Locus," Genome Research, 1997, vol. 7, pp. 250-261.

Kellermann S., et al., "Developing the XENOMOUSE® Technology for Evaluating Immunogenicity," AntibOZ 2: An International Forum to Predict the Next Wave of Protein-based Therapies and Immuno Diagnostics, 2004, AntibOZ 2 Conference, Australia, 1 page (abstract only).

Kelley S.K., et al., "Preclinical Pharmacokinetics, Pharmacodynamics, and Activity of a Humanized Anti-CD40 Antibody (SGN-40) in Rodents and Non-Human Primates, " British Journal of Pharmacology, 2006, vol. 148, pp. 1116-1123.

Kenter A.L., et al., "Three-Dimensional Architecture of the IgH Locus Facilitates Class Switch Recombination," Annals of the New York Academy of Sciences, 2012, vol. 1267, pp. 86-94.

Kettleborough, C.A., et al., "Isolation of tumor cell-specific single-chain Fv from immunized mice using phage-antibody libraries and the re-construction of whole antibodies from these antibody fragments," Eur. J. Immunol. 1994, vol. 24, pp. 952-958.

Khodarovich Y.M., et al., "Expression of Eukaryotic Recombinant Proteins and Deriving Them from the Milk of Transgenic Animals," Applied Biochemistry and Microbiology, Problems and Aspects, 2013, vol. 49, Issue No. 9, pp. 711-722.

Kilpatrick K.E., et al., "Rapid Development of Affinity Matured Monoclonal Antibodies Using RIMMS," Hybridoma, 1997, vol. 16, Issue No. 4, pp. 381-389.

Kim J.Y., et al., "CHO Cells in Biotechnology for Production of Recombinant Proteins: Current State and Further Potential," Applied Microbiology Biotechnology, 2012, vol. 93 (3), pp. 917-930.

Kim S.J., et al., "Antibody Engineering for the Development of Therapeutic Antibodies," Mol. Cells, 2005, vol. 20 (1), pp. 17-29.

Kim T., et al., "Expression and Relationship of Male Reproductive ADAMs in Mouse," Biology of Reproduction, 2006, vol. 74 (4), pp. 744-750.

Kindt T.J. et al., "Organization and Expression of Immunoglobulin Genes," Immunology, Sixth edition, Chapter 5, 2007 (36 pages, including cover sheet and copyright page), pp. 111-144.

Kingzette M., et al., "Trans-Chromosomal Recombination within the Ig Heavy Chain Switch Region in B Lymphocytes, " Proceedings of the National Academy of Sciences of the U.S.A., 1998, vol. 95 (20), pp. 11840-11845.

Kitamura D., et al., "A B Cell-Deficient Mouse by Targeted Disruption of the Membrane Exon of the Immunoglobulin u Chain Gene, " Nature, 1991, vol. 350 (6317), pp. 423-426.

Kokubu C. et al., "A transposon-based chromosomal engineering method to survey a large cis-regulatory landscape in mice," Nature Genetics, Aug. 2009, vol. 41, Issue No. 8, pp. 946-954.

Koller B.H., et al. "Altering Genes in Animals by Gene Targeting," Annu. Rev. Immunol., 1992, vol. 10, pp. 705-730.

Kondo S., et al., "Highly improved Gene Targeting by Germline-Specific Cas9 Expression in *Drosophila*," Genetics, vol. 195, Nov. 2013, pp. 715-721 (Abstract).

Kondo S., et al., "Highly improved Gene Targeting by Germline-Specific Cas9 Expression in *Drosophila*," Genetics, vol. 195, Nov. 2013, pp. 715-721.

Kostenuik P.J., et al., "Denosumab, a Fully Human Monoclonal Antibody to RANKL, Inhibits Bone Resorption and Increases BMD in Knock-in Mice that Express Chimeric (Murine/Human) RANKL," Journal of Bone and Mineral Research, 2009, vol. 24 (2), pp. 182-195.

Kotzamanis G., et al., "Construction of human artificial chromosome vectors by recombineering," Gene, 2005, vol. 351, pp. 29-38.

Kotzamanis G., et al., "Recombining Overlapping BACs into a Single Larger BAC," BMC Biotechnology, 2004, vol. 4 (1), 10 pages.

Kouskoff V., et al., "Cassette Vectors Directing Expression of T Cell Receptor Genes in Transgenic Mice," Journal of Immunological Methods, 1995, vol. 180 (2), pp. 273-280.

Krause J.C., et al., "Epitope-Specific Human Influenza Antibody Repertoires Diversify by B Cell Intraclonal Sequence Divergence and Interclonal Convergence," Journal of Immunology, 2011, vol. 187 (7), pp. 3704-3711.

Kriangkum J., et al., "Molecular Characterization of Waldenstrom's Macroglobulinemia Reveals Frequent Occurrence of Two B-Cell Clones Having Distinct IgH VDJ Sequences," Clinical Cancer Research, Apr. 2007, vol. 13 (7), pp. 2005-2013.

Krutskikh A., et al., "Epididymal Protein Rnase10 is Required for Post-Testicular Sperm Maturation and Male Fertility," The FASEB Journal, 2012, vol. 26 (10), pp. 4198-4209.

Kucherlapati R.S., et al., "Homologous Recombination Between Plasmids in Mammalian Cells can be Enhanced by Treatment of Input DNA," Proceedings of the National Academy of Sciences of the U.S.A., 1984, vol. 81 (10), pp. 3153-3157.

Kumar R., et al., "A Novel Strategy for Efficient Production of Anti-V3 Human scFvs Against HIV-1 clade C," BMC Biotechnology, Nov. 2012, vol. 12 (87), 15 pages.

Kuraoka M., et al., "AID Expression During B-Cell Development: Searching for Answers," Immunologic Research, 2011, vol. 49 (1-3), pp. 3-13.

Kuroiwa Y., et al., "Sequential Targeting of the Genes Encoding Immunoglobulin-μ and Prion Protein in Cattle," Nature Genetics, 2004, vol. 36 (7), pp. 775-780.

Kuzin I.I., et al, "Requirement for enhancer specificity in immunoglobulin heavy chain locus regulation," Journal of Immunology, Jun. 2008, vol. 180 (11), pp. 7443-7450.

Kuzminov A., "DNA Replication Meets Genetic Exchange: Chromosomal Damage and Its Repair by Homologous Recombination," Proc. Natl. Acad. Sci. USA, Jul. 2001, vol. 98(15), pp. 8461-8468.

Shore D.E., Attorney for Applicant, Third-Party Pre-Issuance Submission Under 37 CFR Sec. 1.290 in U.S. Appl. No. 16/353,870, filed Dec. 20, 2019, 104 pages.

Shore, D.E., Attorney for Applicant, Third-Party Pre-Issuance Submission Under 37 CFR Sec. 1.290 in U.S. Appl. No. 14/543,359, filed Mar. 3, 2017, 16 pages.

(56)         References Cited

OTHER PUBLICATIONS

Shore, D.E., Attorney for Applicant, Third-Party Pre-Issuance Submission Under 37 CFR Sec. 1.290 in U.S. Appl. No. 16/296,033, filed Jul. 14, 2020, 75 pages.

Shore, D.E., Attorney for Applicant, Third-Party Pre-Issuance Submission Under 37 CFR Sec. 1.290 in U.S. Appl. No. 16/296,033, filed Jul. 14, 2020, 78 pages (Second Submission).

Shultz L.D., et al., "Humanized Mice in Translational Biomedical Research," Nature Reviews / Immunology, 2007, vol. 7 (2), pp. 118-130.

Siegel, D.L. et al., "Section 5: Structural/genetic analysis of mAbs to blood group antigens. Coordinator's Report," Transfus. Clin. Biol., 2002, vol. 9, pp. 83-97.

Sigmund C.D., "Viewpoint: Are Studies in Genetically Altered Mice Out of Control?," Arteriosclerosis, Thrombosis, and Vascular Biology, Jun. 2000, vol. 20 (6), pp. 1425-1429.

Siman-Tov D.D., et al., "Differentiation of a passive vaccine and the humoral immune response toward infection: Analysis of phage displayed peptides," Vaccine, Jan. 2006, vol. 24, pp. 607-612.

Simpson E.M., et al., "Genetic Variation Among 129 Substrains and its Importance for Targeted Mutagenesis in Mice," Nature Genetics, 1997, vol. 16 (1), pp. 19-27.

Sinzelle L., et al., "Transposition of a reconstructed Harbinger element in human cells and functional homology with two transposon-derived cellular genes," Proceedings of the National Academy of Sciences of the U.S.A., Mar. 2008, vol. 105, Issue No. 12, pp. 4715-4720.

Sirac C., et al., "Role of the Monoclonal κ Chain V Domain and Reversibility of Renal Damage in a Transgenic Model of Acquired Fanconi Syndrome," Blood, 2006, vol. 108 (2), pp. 536-543.

Skarnes W.C., et al., "A Conditional Knockout Resource for the Genome-Wide Study of Mouse Gene Function," Nature, 2011, vol. 474 (7351), pp. 337-342.

Skoultchi A.I., et al., "Expression of Genes Inserted at the Human β-Globin Locus by Homologous Recombination," Progress in Clinical and Biological Research, 1987, vol. 251, pp. 581-594.

Sleeman, Mark W., Declaration (Evidence in Support of Opposition thereto by Regeneron Pharmaceuticals, Inc. for Application No. 2011266843), dated Jan. 29, 2016, 24 pages.

Sleeman, Mark W., Second Declaration (Evidence in Support of Opposition thereto by Regeneron Pharmaceuticals, Inc.) for Application No. 2011266843, dated Jul. 4, 2016, 7 pages.

Sleeman, Mark W., Third Declaration (Evidence in Support of Opposition thereto by Regeneron Pharmaceuticals, Inc. for Application No. 2011266843), dated Jan. 25, 2018, 9 pages.

Smith K.R., "Gene Transfer in Higher Animals: Theoretical Considerations and Key Concepts," Journal of Biotechnology, 2002, vol. 99 (1), pp. 1-22.

Smith, K., et al., "Rapid generation of fully human monoclonal antibodies specific to a vaccinating antigen," Nature Protocols, 2009, vol. 4 (3), pp. 372-384.

Smithies O., "Direct Alteration of a Gene in the Human Genome," Journal of Inherited Metabolic Disease, 1986, vol. 9 (Suppl. 1), pp. 92-97.

Smithies O., et al., "Insertion of DNA Sequences into the Human Chromosomal β-Globin Locus by Homologous Recombination," Nature, 1985, vol. 317 (6034), pp. 230-234.

Sohn J., et al., "Somatic Hypermutation of an Immunoglobulin μ Heavy Chain Transgene," The Journal of Experimental Medicine, 1993, vol. 177 (2), pp. 493-504.

Song K., et al., "Accurate Modification of a Chromosomal Plasmid by Homologous Recombination in Human Cells," Proceedings of the National Academy of Sciences of the U.S.A., 1987, vol. 84 (19), pp. 6820-6824.

Sonoda E., et al., "B Cell Development Under the Condition of Allelic Inclusion," Immunity, 1997, vol. 6 (3), pp. 225-233.

Sopher B., et al., "Efficient recombination-based methods for bacterial artificial chromosome fusion and mutagenesis," Gene, 2006, vol. 371, pp. 136-143.

Sorrell D.A., et al., "Targeted modification of mammalian genomes," Biotechnology Advances, vol. 23, 2005, pp. 431-469.

Sosio M., et al., "Assembly of large genomic segments in artificial chromosomes by homologous recombination in Escherichia coli," Nucleic Acids Research, 2001, vol. 29(7), pp. e37-1-e37-8.

Soukharev S., et al., "Segmental Genomic Replacement in Embryonic Stem Cells by Double Lox Targeting," Nucleic Acids Research, 1999, vol. 27 (18), pp. e21.

Spanopoulou E., et al., "Functional Immunoglobulin Transgenes Guide Ordered B-Cell Differentiation in Rag-1-Deficient Mice," Genes & Development, 1994, vol. 8 (9), pp. 1030-1042.

Stacey A., et al., "Use of Double-Replacement Gene Targeting To Replace the Murine ?-Lactalbumin Gene with Its Human Counterpart in Embryonic Stem Cells and Mice," Molecular and Cellular Biology, Feb. 1994, vol. 14(2), pp. 1009-1016.

Stavnezer J., et al., "Mechanism and Regulation of Class Switch Recombination," Annual Review of Immunology, 2008, vol. 26, pp. 261-292.

Stein R., et al., "Characterization of a humanized IgG4 anti-HLA-DR monoclonal antibody that lacks effector cell functions but retains direct antilymphoma activity and increases the potency of rituximab," Blood, Oct. 2006, vol. 108 (8), pp. 2736-2744.

Stephen R., Olswang LLP, Kymab Limited Statement of Facts and Evidence in opposition to EP2550363, dated Sep. 10, 2015, 22 pages.

Stephen R., Olswang LLP, Response to Appeal filed by Regeneron Pharmaceuticals, Inc. for Application No. 14170196.1, as filed with the European Patent Office dated Mar. 12, 2020, 23 pages.

Stephen R., Olswang LLP, Response to Examination Report dated Jun. 6, 2016 for Application No. 14176740.0, as filed with the European Patent Office on Oct. 10, 2016, 4 pages.

Stephen R., Olswang LLP, Response to Examination Report dated Jun. 6, 2016 to the European Patent Office with corresponding claims for Application No. 14176740.0, dated Oct. 10, 2016, 11 pages.

Stephen R., Olswang LLP, Response to Examination Report dated Nov. 10, 2016 to the European Patent Office with corresponding claims for Application No. 14176740.0 on Mar. 17, 2017, 13 pages.

Stephen R., Olswang LLP, Response to Grounds of Appeal dated Dec. 14, 2018 for Application No. 12171793.8 (Patent No. EP2517557), as filed with the European Patent Office on Apr. 29, 2019, 17 pages.

Stephen R., Olswang LLP, Response to Opposition (as filed by Regeneron Pharmaceuticals, Inc. on Jan. 11, 2017) for Application No. 12171793.8, as filed with the European Patent Office on Jun. 23, 2017, 8 pages.

Stephen R., Olswang LLP, Response to Opposition in the name of Kymab Limited filed against EP2758535B1, dated Mar. 22, 2018, 26 pages.

Stephen R., Olswang LLP, Response to Search Report dated Oct. 15, 2014 for Application No. 14176740.0, as filed with the European Patent Office on May 12, 2015, 4 pages.

Stephen R., Olswang LLP, Response to Search Report dated Oct. 15, 2014 to the European Patent Office with corresponding claims for Application No. 14176740.0, dated May 12, 2015, 10 pages.

Stephen R., Olswang LLP, Response to Summons and Preliminary Opinion pertaining to Patent No. EP 2517557 for Application No. 12171793.8, as filed with the European Patent Office on May 17, 2018, 4 pages.

Stephen R., Olswang LLP, Response to Third-Party Observations dated Aug. 10, 2015 and Examination Report dated Oct. 23, 2015 for Application No. 14176740.0, as filed with the European Patent Office on Apr. 23, 2016, 6 pages.

Stephen R., Olswang LLP, Response to Third-Party Observations dated Aug. 10, 2015 and Examination Report dated Oct. 23, 2015 to the European Patent Office with corresponding claims for Application No. 14176740.0, dated Apr. 23, 2016, 13 pages.

Stephen R., Olswang LLP, Response to Third-Party Observations for Application No. 12171793.8, as filed with the European Patent Office on Apr. 17, 2015, 3 pages.

Stephen, R., Cameron McKenna Nabarro Olswang LLP, Response to Opposition to EP 3028564 (Application No. 16151214.0) with supporting documents, dated Nov. 16, 2018, 164 pages.

(56) References Cited

OTHER PUBLICATIONS

Stephen, R., Cameron McKenna Nabarro Olswang LLP, Response to Opposition to EP 3241435 (Application No. 17174426.1) with supporting documents, dated Jul. 20, 2022, 21 pages.

Stevens S. et al., "VelocImmuneTM: Humanization of immuno-globulin loci using VelociGene® technology," (Abstract 4) Presented at 1st International MUGEN Conference on Animal Models for Human Immunological Disease, Athens, Greece, Sep. 10-13, 2006, 1 page.

Stevens S., "Human Antibody Discovery, VelocImmune—A Novel Platform," Pharma Focus Asia, 2008, vol. 8, pp. 72-74.

Stevens S., et al., Expanded Poster: "VelocImmuneTM: Humanization of immunoglobulin loci using VelociGene® technology," Sep. 2006, 6 pages.

Yancopoulos G.D., et al., "Preferential Utilization of the Most JH-Proximal VH Gene Segments in Pre-B-Cell Lines," Nature, Oct. 1984, vol. 311 (5988), pp. 727-733.

Yang C., et al., "Mutant PFN1 causes ALS phenotypes and progressive motor neuron degeneration in mice by a gain of toxicity," Proceedings of the National Academy of Sciences of the U.S.A., Sep. 2016, vol. 113, Issue No. 41, pp. E6209-E6218.

Yang X.W., et al., "Homologous Recombination Based Modification in *Escherichia coli* and Germline Transmission in Transgenic Mice of a Bacterial Artificial Chromosome," Nature Biotechnology, Sep. 1997, vol. 15 (9), pp. 859-865.

Yu C.C.K., et al., "Differential Usage of VH Gene Segments is Mediated by cis Elements," Journal of Immunology, 1998, vol. 161 (7), pp. 3444-3454.

Yu Y., et al., "Engineering Chromosomal Rearrangements in Mice," Nature Reviews Genetics, 2001, vol. 2 (10), pp. 780-790.

Yusa K., et al., "Generation of transgene-free induced pluripotent mouse stem cells by the piggyBac transposon," Nature Methods, May 2009, vol. 6, Issue No. 5, pp. 363-371.

Yusa K., et al., "Targeted gene correction of ?1-antitrypsin deficiency in induced pluripotent stem cells," Nature, Oct. 2011, vol. 478, Issue No. 7369, pp. 391-394.

Zemlin M., et al., "Expressed Murine and Human CDR-H3 Intervals of Equal Length Exhibit Distinct Repertoires that Differ in their Amino Acid Composition and Predicted Range of Structures," Journal of Molecular Biology, 2003, vol. 334 (4), pp. 733-749.

Zhang X., et al., "Combination of overlapping bacterial artificial chromosones by a two-step recombinogenic engineering method," Nucleic Acids Research, 2003, vol. 31 (15), pp. e81-1-e81-6.

Zhang Y., et al., "A New Logic for DNA Engineering Using Recombination in *Escherichia coli*," Nature Genetics, 1998, vol. 20 (2), pp. 123-128.

Zhao S., "A Comprehensive BAC Resource," Nucleic Acids Research, 2001, vol. 29 (1), pp. 141-143.

Zhao Y., et al., "Physical Mapping of the Bovine Immunoglobulin Heavy Chain Constant Region Gene Locus," Journal of Biological Chemistry, Sep. 2003, vol. 278 (37), pp. 35024-35032.

Zheng B., et al., "Engineering Mouse Chromosomes with Cre-loxP: Range, Efficiency, and Somatic Applications," Molecular and Cellular Biology, Jan. 2000, vol. 20 (2), pp. 648-655.

Zheng J., et al., "Immunoglobulin Gene Transcripts Have distinctive VHDJH Recombination Characteristics in Human Epithelial Cancer Cells", Journal of Biological Chemistry, Mar. 2009, vol. 284 (20), pp. 13610-13619.

Zhu Z., et al., "Cross-Reactive HIV-1-Neutralizing Human Monoclonal Antibodies Identified from a Patient with 2F5-Like Antibodies," Journal of Virology, Nov. 2011, vol. 85 (21), pp. 11401-11408.

Zimmerman, A., et al., "Immunoglobulin light chain (IgL) genes in zebrafish: Genomic configurations and inversional rearrangements between (VL-JL-CL) gene clusters," Developmental and comparative immunology, 2008, vol. 32(4), pp. 421-434.

Zou X., et al., "Removal of the BiP-Retention Domain in Cμ Permits Surface Deposition and Developmental Progression Without L-Chain," Molecular Immunology, 2008, vol. 45 (13), pp. 3573-3579.

Zou X., et al., "Subtle differences in antibody responses and hypermutation of lambda chains in mice with a disrupted x contant region," European Journal of Immunology, 1995, vol. 25, pp. 2154-2162.

Zou Y., et al., "Cre-loxP-Mediated Gene Replacement: a Mouse Strain Producing Humanized Antibodies," Current Biology, 1994, vol. 4 (12), pp. 1099-1103.

Zwick M.B., et al., "The Long Third Complementarity-Determining Region of the Heavy Chain Is Important in the Activity of the Broadly Neutralizing Anti-Human Immunodeficiency Virus Type 1 Antibody 2F5," Journal of Virology, Mar. 2004, vol. 78 (6), pp. 3155-3161.

European Patent Office, Extended European Search Report for Application No. 22168117.4, dated Oct. 24, 2022, 15 pages.

European Patent Office, Communication pursuant to Rule 114(2) EPC regarding 14772198.9, dated Mar. 30, 2016, 16 pages.

European Patent Office, Decision of the Opposition Division revoking EP2758535, dated Jun. 3, 2019, 17 bages.

European Patent Office, Decision rejecting the opposition (Art. 101(2) EPC) for Application No. 10 010 741.6, dated Apr. 25, 2018, 44 pages.

European Patent Office, Decision of Technical Board of Appeal 3.3.04, relating to Application No. EP11705964.2 (Patent No. EP2582230), dated Apr. 26, 2019 (including Datasheet and Notice of Decision to Refuse), 10 pages.

European Patent Office, Summons to Attend Oral Proceedings pursuant to Rule 115(1) EPC, relating to Application No. EP11705964.2 (Patent No. EP2582230), dated Jul. 4, 2017, 10 pages.

European Patent Office, F. Chambonnet, Authorized officer, International Search Report for Application No. PCT/GB2012/052380, mailed on Jan. 3, 2013, 17 pages, together with the Written Opinion of the International Searching Authority.

European Patent Office, Gaby Brouns, Authorized officer, International Search Report for Application No. PCT/GB2012/052956, mailed on Mar. 1, 2013, 14 pages, together with the Written Opinion of the International Searching Authority.

European Patent Office, Gaby Brouns, Authorized officer, International Search Report for Application No. PCT/GB2012/052960, mailed on Apr. 29, 2013, 19 pages, together with the Written Opinion of the International Searching Authority.

European Patent Office, Gaby Brouns, Authorized officer, International Search Report for Application No. PCT/GB2013/050682, mailed on Sep. 25, 2013, 16 pages, together with the Written Opinion of the International Searching Authority.

European Patent Office, Gaby Brouns, Authorized officer, International Search Report for Application No. PCT/GB2013/050683, mailed on Jul. 9, 2013, 11 pages, together with the Written Opinion of the International Searching Authority.

European Patent Office, Gaby Brouns, Authorized officer, International Search Report for Application No. PCT/ GB2013/051280, mailed on Nov. 15, 2013, 19 pages, together with the Written Opinion of the International Searching Authority.

European Patent Office, Examination Report for Application No. 13723933.1, dated Feb. 21, 2019, 7 pages.

European Patent Office, Examination Report for Application No. 13723933.1, dated Jan. 17, 2018, 6 pages.

European Patent Office, Examination Report for Application No. 13723933.1, dated Mar. 18, 2020, 7 pages.

European Patent Office, Extended European Search Report for Application No. 15188522.5 dated Feb. 2, 2016, 15 pages.

European Patent Office, Extended European Search Report for Application No. 17196214.5, dated Jan. 2, 2018, 13 pages.

European Patent Office, Extended European Search Report for Application No. 18153171.6, dated Jun. 28, 2018, 15 pages.

European Patent Office, Extended European Search Report for Application No. 22173215.9, dated Dec. 9, 2022, 12 pages.

European Patent Office, Examination Report for Application No. 12795841.1, dated Feb. 12, 2016, 5 pages.

European Patent Office, Examination Report for Application No. 13711119.1, dated Dec. 17, 2015, 6 pages.

European Patent Office, Examination Report for Application No. 13711119.1, dated Jul. 13, 2016, 6 pages.

(56) References Cited

OTHER PUBLICATIONS

European Patent Office, Examination Report for Application No. 15188522.5, dated Aug. 11, 2017, 6 pages.
European Patent Office, International Searching Authority, Examiners Report on Allowable Claims for Application No. PCT/GB2010/051122, Jan. 2004, 1 page.
European Patent Office, Irmgard Scheffzyk, Authorized officer, International Search Report for Application No. PCT/EP2018/068309, mailed on Jan. 15, 2019, 14 pages, together with the Written Opinion of the International Searching Authority.
European Patent Office, Examination Report for Application No. 18743421.2, dated Feb. 26, 2021, 3 pages.
European Patent Office, Extended European Search Report for Application No. 14196645.7, mailed on Jun. 26, 2015, 12 pages.
European Patent Office, Examination Report for Application No. 12778780.2, dated Oct. 14, 2016, 3 pages.
European Patent Office, Julien Landre, Authorized officer, International Search Report for Application No. PCT/GB2012/052670, mailed on Feb. 14, 2013, 12 pages, together with the Written Opinion of the International Searching Authority.
European Patent Office, Laurent Deleu, Authorized Officer, International Preliminary Report on Patentability Chapter II for Application No. PCT/GB2010/051122, date of completion Nov. 2, 2011, 33 pages.
European Patent Office, Laurent Deleu, Authorized officer, International Search Report for Application No. PCT/GB2010/051122, mailed on Sep. 29, 2010, 9 pages, together with the Written Opinion of the International Searching Authority.
European Patent Office, Laurent Deleu, Authorized officer, International Search Report for Application No. PCT/GB2011/050019, mailed on May 16, 2011, 12 pages, together with the Written Opinion of the International Searching Authority.
European Patent Office, European Search Report for Application No. 12194977.0, mailed on Jul. 5, 2013, 4 pages.
European Patent Office, Examination Report for Application No. 12194970.5, dated Sep. 23, 2013, 6 pages.
European Patent Office, Examination Report for Application No. 14176740.0, dated Jun. 6, 2016, 5 pages.
European Patent Office, Examination Report for Application No. 14176740.0, dated Oct. 23, 2015, 5 pages.
European Patent Office, Examination Report for Application No. 16151215.7, dated Jan. 23, 2017, 5 pages.
European Patent Office, Examination Report for Application No. 17174426.1, dated Feb. 5, 2020 (with Annex), 11 pages.
European Patent Office, Extended European Search Report for Application No. 12171791.2, mailed on Jun. 18, 2013, 5 pages.
European Patent Office, Extended European Search Report for Application No. 12171793.8 dated Jun. 21, 2013, 8 pages.
European Patent Office, Extended European Search Report for Application No. 12194970.5, dated Jan. 23, 2013, 9 pages.
European Patent Office, Extended European Search Report for Application No. 12194977.0, dated Jul. 17, 2013, 8 pages.
European Patent Office, Extended European Search Report for Application No. 12195041.4, dated Nov. 18, 2013, 8 pages.
European Patent Office, Extended European Search Report for Application No. 14176740.0, mailed on Oct. 15, 2014, 7 pages.
European Patent Office, Extended European Search Report for Application No. 16151215.7, dated Mar. 16, 2016, 11 pages.
European Patent Office, Extended European Search Report for Application No. 17174426.1, dated Sep. 14, 2017, 10 pages.
European Patent Office, Minutes of the oral proceedings before the Opposition Division, relating to Application No. EP12716101.6 (Patent No. EP2550363), with supporting documents, dated May 26, 2017, 62 pages.
European Patent Office, Notice of Opposition to a European Patent EP2758534 in the name of Kymab Limited pertaining to Application No. 12762377.5, dated May 4, 2020, 6 pages.
European Patent Office, Notice of Opposition to European Patent EP3241435 in the name of Kymab Limited pertaining to Application No. 17174426.1, dated Mar. 3, 2022, 44 pages.

European Patent Office, Notice of Opposition, together with Statement of Fact and Arguments in Support of Opposition related to European Patent EP2989894 in the name of Kymab Limited pertaining to Application No. 15188522.5, dated May 17, 2021, 34 pages.
Grund M., European Patent Attorney, Grund Intellectual Property Group, Third-Party Observations according to Article 115 EPC regarding 12772122.3, dated May 17, 2016, 7 pages.
Grund M., European Patent Attorney, Grund Intellectual Property Group, Third-Party Observations according to Article 115 EPC regarding 12795606.8, dated Aug. 22, 2014, 8 pages.
Grund M., European Patent Attorney, Grund Intellectual Property Group, Third-Party Observations according to Article 115 EPC regarding 12795606.8, dated Feb. 26, 2014, 6 pages.
Grund M., European Patent Attorney, Grund Intellectual Property Group, Third-Party Observations according to Article 115 EPC regarding 12795606.8, dated Mar. 26, 2015, 4 pages.
Grund M., European Patent Attorney, Grund Intellectual Property Group, Third-Party Observations according to Article 115 EPC regarding 13711119.1, dated Dec. 9, 2015, 7 pages.
Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Grund M., European Patent Attorney, Grund Intellectual Property Group, Third-Party Observations according to Article 115 EPC regarding 13723933.1, dated Sep. 20, 2021, 5 pages.
Grund M., European Patent Attorney, Grund Intellectual Property Group, Third-Party Observations according to Article 115 EPC regarding 14176740.0, dated Aug. 10, 2015, 13 pages.
Grund M., European Patent Attorney, Grund Intellectual Property Group, Third-Party Observations according to Article 115 EPC regarding 14176740.0, dated Nov. 2, 2016, 4 pages.
Grund M., European Patent Attorney, Grund Intellectual Property Group, Third-Party Observations according to Article 115 EPC regarding 14781635.9, dated May 18, 2018, 4 pages.
Grund M., European Patent Attorney, Grund Intellectual Property Group, Third-Party Observations according to Article 115 EPC regarding 15188522.5, dated Mar. 13, 2019, 3 pages.
Grund M., European Patent Attorney, Grund Intellectual Property Group, Third-Party Observations according to Article 115 EPC regarding 16151215.7, dated Mar. 1, 2017, 4 pages.
Grund M., European Patent Attorney, Grund Intellectual Property Group, Third-Party Observations according to Article 115 EPC regarding 16189625.3, dated Mar. 23, 2017, 5 pages.
Grund M., European Patent Attorney, Grund Intellectual Property Group, Third-Party Observations according to Article 115 EPC regarding 17174426.1, dated Feb. 11, 2019, 5 pages.
Grund M., European Patent Attorney, Grund Intellectual Property Group, Third-Party Observations according to Article 115 EPC regarding 17174426.1, dated Jun. 27, 2018, 7 pages.
Grund M., European Patent Attorney, Grund Intellectual Property Group, Third-Party Observations According to Article 115 EPC regarding 17196235.0, dated Nov. 27, 2018, 22 pages.
Grund M., European Patent Attorney, Grund Intellectual Property Group, Third-Party Observations according to Article 115 EPC regarding 18153171.6, dated Feb. 2, 2022, 6 pages.
Grund M., European Patent Attorney, Grund Intellectual Property Group, Third-Party Observations according to Article 115 EPC regarding 19207052.2, dated Aug. 19, 2020, 4 pages.
Grund M., European Patent Attorney, Grund Intellectual Property Group, Third-Party Observations according to Article 115 EPC regarding 19207052.2, dated Oct. 28, 2021, 5 pages.
Grund M., European Patent Attorney, Grund Intellectual Property Group, Third-Party Observations according to Article 115 EPC regarding 20171931.7, dated Dec. 13, 2021, 5 pages.
Grund M., European Patent Attorney, Grund Intellectual Property Group, Third-Party Observations according to Article 115 EPC regarding 20191651.7, dated Nov. 24, 2021, 7 pages.

(56) References Cited

OTHER PUBLICATIONS

Grund M., European Patent Attorney, Grund Intellectual Property Group, Third-Party Observations regarding Application No. PCT/GB2012/052297, dated Jan. 17, 2014, 3 pages.

Grund M., European Patent Attorney, Grund Intellectual Property Group, Third-Party Observations regarding Application No. PCT/GB2012/052298, dated Jan. 17, 2014, 4 pages.

Grund M., European Patent Attorney, Grund Intellectual Property Group, Third-Party Observations regarding Application No. PCT/GB2012/052380, dated Jan. 24, 2014, 4 pages.

Grund M., European Patent Attorney, Grund Intellectual Property Group, Third-Party Observations regarding Application No. PCT/GB2012/052956, dated Mar. 26, 2014, 2 pages.

Grund M., European Patent Attorney, Grund Intellectual Property Group, Third-Party Observations regarding Application No. PCT/GB2012/052960, dated Apr. 2, 2014, 3 pages.

Grund M., European Patent Attorney, Grund Intellectual Property Group, Third-Party Observations regarding Application No. PCT/GB2013/050682, dated Jul. 28, 2014, 3 pages.

Grund M., European Patent Attorney, Grund Intellectual Property Group, Third-Party Observations regarding Application No. PCT/GB2013/050683, dated Jul. 28, 2014, 2 pages.

Grund M., European Patent Attorney, Grund Intellectual Property Group, Third-Party Observations regarding Application No. PCT/US2012/026416, dated Jun. 6, 2013, 2 pages.

Grund, M., European Patent Attorney, Grund Intellectual Property Group, Third-Party Observations regarding Application No. EP 20188009.3, dated Jun. 8, 2022, 4 pages.

Gu H., et al., "Independent Control of Immunoglobulin Switch Recombination at Individual Switch Regions Evidenced Through Cre-loxP-Mediated Gene Targeting," Cell, 1993, vol. 73 (6), pp. 1155-1164.

Guan C., et al., "A Review of Current Large-Scale Mouse Knockout Efforts," Genesis, vol. 48, 2010, pp. 73-85.

Guerrero C., et al., "The Bleomycin Resistance Gene of Transposon Tn5 is an Excellent Marker for Transformation of Corynebacteria," Applied Microbiology and Biotechnology, 1992, vol. 36 (6), pp. 759-762.

Guirouilh-Barbat J., et al., "Is homologous recombination really an error-free process?", Frontiers in Genetics, Jun. 2014, vol. 5 (175), 15 pages.

Guntaka R.V., "Transcription Termination and Polyadenylation in Retroviruses," Microbiological Reviews, 1993, vol. 67 (3), pp. 511-521.

Guo Y., et al., "A Preliminary Analysis of the Immunoglobulin Genes in the African Elephant (*Loxodonta africana*)," PLoS One, Feb. 2011, vol. 6 (2), pp. e16889-1-e16889-14.

Gutterson N.I., et al., "Replacement and Amplification of Bacterial Genes With Sequences Altered in Vitro," Proc. Natl. Acad. Sci. USA, Aug. 1983, vol. 80(16), pp. 4894-4898.

Hagiwara S., "Transgenic Expression of VpreB-3 Under the Control of the Immunoglobulin Heavy Chain Enhancer and SV40 Promoter," Kobe Journal of Medical Sciences, 1996, vol. 42 (1), pp. 43-59 (abstract only).

Hamers-Caterman C., et al., "Naturally occurring antibodies devoid of light chains," Nature, Jun. 1993, vol. 363, pp. 446-448.

Han C., et al., "Comprehensive Analysis of Reproductive ADAMs: Relationship of ADAM4 and ADAM6 with an ADAM Complex Required for Fertilization in Mice," Biology of Reproduction, 2009, vol. 80 (5), pp. 1001-1008.

Harding F.A., et al., "Class Switching in Human Immunoglobulin Transgenic Mice," Annals of the New York Academy of Sciences, 1995, vol. 764, pp. 536-546.

Hasty P., et al., "Gene targeting, principles, and practice in mammalian cells," Gene Targeting, A Practical Approach, 2nd Edition, Oxford, 2000, pp. 1-175, including cover pages (XP055500641).

Hasty P., et al., "Introduction of a Subtle Mutation Into the Hox-2.6 Locus in Embryonic Stem Cells," Nature, Mar. 1991, vol. 350(6315), pp. 243-246.

Hasty P., et al., "Target Frequency and Integration Pattern for Insertion and Replacement Vectors in Embryonic Stem Cells," Molecular and Cellular Biology, 1991, vol. 11 (9), pp. 4509-4517.

Hayes Emily A.L., Mewburn Ellis LLP, Supplemental Response on behalf of Regeneron Pharmaceuticals, Inc. regarding Opposition filed Sep. 16, 2021 relating to European Patent No. 3,128,009 (European Appln. No. 16189625.3), dated Dec. 7, 2021, 17 pages.

He Y., et al., "Efficient Isolation of Novel Human Monoclonal Antibodies with Neutralizing Activity Against HIV-1 from Transgenic Mice Expressing Human Ig Loci," The Journal of Immunology, 2002, vol. 169, pp. 595-605.

Hendricks J., et al., "Organization of the Variable Region of the Immunoglobulin Heavy-Chain Gene Locus of the Rat," Immunogenetics, 2010, vol. 62 (7), pp. 479-486.

Herschbach Jarrell B., Third-Party Pre-Issuance Submission Under 37 CFR Section 1.290 in U.S. Appl. No. 14/052,259, dated Aug. 6, 2014, 7 pages.

Hewitt S.L., et al., "Association between the Igk and Igh immunoglobulin loci mediated by the 3' Igk enhancer Induces 'decontraction' of the Igh locus in pre-B cells," Nature Immunology, Apr. 2008, vol. 9 (4), pp. 396-404.

Prosser H.M., et al., "A Resource of Vectors and ES Cells for Targeted Deletion of MicroRNAs in Mice," Nature Biotechnology, 2011, vol. 29 (9), pp. 840-845.

Prosser H.M., et al., "Mosaic Complementation Demonstrates a Regulatory Role for Myosin Vlla in Actin Dynamics of Stereocilia," Molecular and Cellular Biology, 2008, vol. 28 (5), pp. 1702-1712.

Pruzina S., et al., "Human Monoclonal Antibodies to HIV-1 gp140 from Mice Bearing YAC-Based Human Immunoglobulin Transloci," Protein Engineering, Design & Selection, 2011, vol. 24 (10), pp. 791-799.

Puente X.S., et al., "Comparative Genomic Analysis of Human and Chimpanzee Proteases," Genomics, 2005, vol. 36 (6), pp. 638-647.

Pérez-Luz S., et al., "Factor Vlll mRNA expression from a BAC carrying the intact locus made by homologous recombination," Genomics, 2007, vol. 90, pp. 610-619.

Qi N.R., et al., "A New Transgenic Rat Model of Hepatic Steatosis and the Metabolic Syndrome," Hypertension, 2005, vol. 45 (5), pp. 1004-1011.

Qu S., et al., "Gene Targeting of ErbB3 Using a Cre-Mediated Unidirectional DNA Inversion Strategy," Genesis, 2006, vol. 44 (10), pp. 477-486.

Raaphorst F.M., et al., "Human Ig heavy chain CDR3 regions in adult bone marrow pre-B cells display an adult phenotype of diversity: evidence for structural selection of DH amino acid sequences," International Immunology, Oct. 1997, vol. 9 (10), pp. 1503-1515.

Ramsden D.A., et al., "Conservation of Sequence in Recombination Signal Sequence Spacers," Nucleic Acids Research, 1994, vol. 22 (10), pp. 1785-1796.

Ramírez-Solis R., et al., "Chromosome Engineering in Mice," Nature, Dec. 1995, vol. 378 (6558), pp. 720-724.

Ravetch, J.V., et al., "Structure of the human immunoglobulin μ locus: Characterization of embryonic and rearranged U and D genes," Cell, Dec. 1981, vol. 27, Issue No. 3, Part 2, pp. 583-591.

Ray P., et al., "Ectopic Expression of a c-kitW42 Minigene in Transgenic Mice: Recapitulation of W Phenotypes and Evidence for c-kit Function in Melanoblast Progenitors, " Genes & Development, 1991, vol. 5 (12A), pp. 2265-2273.

Raynard S.J., et al., "Cis-Acting Regulatory Sequences Promote High-Frequency Gene Conversion between Repeated Sequences in Mammalian Ccells," Nucleic Acids Research, 2004, vol. 32 (19), pp. 5916-5927.

Reddy S.T., et al., "Monoclonal Antibiotics Isolated without Screening by Analysing the Variable-Gene Repertoire of Plasma Cells," Nature Biotechnology, 2010, vol. 28 (9), pp. 965-971.

Regeneron Pharmaceuticals, Inc., et al., "Big Pharma Vies for Mice," Nature Biotechnology, 2007, vol. 25 (6), pp. 613.

Regeneron Pharmaceuticals, Inc., Press Release—"Astellas Licenses Regeneron's Velocimmune® Technology for Discovering Human Monoclonal Antibodies," dated Mar. 30, 2007, 2 pages.

Regeneron Pharmaceuticals, Inc., Press Release—"AstraZeneca Licenses Regeneron's VelocImmune® Technology for Discovering

US 12,696,885 B2

Page 16

(56) References Cited

OTHER PUBLICATIONS

Human Monoclonal Antibodies—AstraZeneca Is First Licensee of Novel VelocImmune Technology License Fees Total up to $120 Million Over Six Years," dated Feb. 5, 2007, 2 pages.
Regeneron Pharmaceuticals, Inc., Press Release—"Regeneron Initiates Major Global Collaboration with Sanofi-aventis of Develop and Commercialize Fully-Human Therapeutic Antibodies," dated Nov. 29, 2007, 2 pages.
Ren L., et al., "Silencing of the immunoglobulin heavy chain locus by removal of all eight constant-region genes in a 200-kb region," Genomics, Aug. 2004, vol. 84, pp. 686-695.
Ren S.Y., et al., "Targeted Insertion Results in a Rhombomere 2-Specific Hoxa2 Knockdown and Ectopic Activation of Hoxa1 Expression," Developmental Dynamics, 2002, vol. 225 (3), pp. 305-315.
Renaut L., et al., "Affinity Maturation of Antibodies: Optimized Methods to Generate High-Quality ScFv Libraries and Isolate IgG Candidates by High-Throughput Screening," Antibody Engineering: Methods and Protocols, Second Edition, Chapter 26, 2012, vol. 907, pp. 451-461.
Retter I., et al., "Sequence and Characterization of the Ig Heavy Chain Constant and Partial Variable Region of the Mouse Strain 129S1," The Journal of Immunology, 2007, vol. 179 (4), pp. 2419-2427.
Richardson, C. et al., "Molecular Basis of 9G4 B cell Autoreactivity in Human Systemic Lupus Erythematosus," The Journal of Immunology, Nov. 2013, vol. 191(10), pp. 4926-4939.
Ricker M., European Patent Attorney, Opposition against EP2421357B1 in the name of Kymab Limited Statement of Facts and Arguments pertaining to Application No. 10734546.4, dated Oct. 23, 2013, 29 pages.
Ricker M., European Patent Attorney, Opposition against EP2758535 in the name of Kymab Limited Statement of Facts and Arguments pertaining to Application No. 12772122.3, dated Aug. 9, 2017, 42 pages.
Ristevski S., "Making Better Transgenic Models: Conditional, Temporal, and Spatial Approaches," Molecular Biotechnology, 2005, vol. 29 (2), pp. 153-163.
Rivera J., et al., "Genetic Background and the Dilemma of Translating Mouse Studies to Humans," Immunity, 2008, vol. 28 (1), pp. 1-4.
Rock E.P., et al., "CDR3 Length in Antigen-specific Immune Receptors", Journal of Experimental Medicine, Jan. 1994, vol. 179, pp. 323-328.
Rodríguez C.I., et al., "High-Efficiency Deleter Mice Show that FLPe is an Alternative to Cre-loxP," Nature Genetics, 2000, vol. 25 (2), pp. 139-140.
Rogozin I.B., et al., "Cutting edge: DGYW/WRCH is a Better Predictor of Mmutability at G:C bases in Lg Hypermutation than the Widely Accepted RGYW/WRCY Motif and Probably Reflects a Two-Step Activation-Induced Cytidine Deaminase-Triggered Process," The Journal of Immunology, 2004, vol. 172 (6), pp. 3382-3384.
Rojas G., et al., "Efficient Construction of a Highly Useful Phage-Displayed Human Antibody Repertoire", Biochemical and Biophysical Research Communications, Nov. 2005, vol. 336(4), pp. 1207-1213.
Romo-Gonzalez, "Novel substitution polymorphisms of human immunoglobulin VH genes in Mexicans," Human Immunology, 2005, vol. 66, pp. 732-740.
Ronai D., et al., "Variegated Expression of the Endogenous Immunoglobulin Heavy-Chain Gene in the Absence of the Intronic Locus Control Region," Molecular and Cellular Biology, Oct. 1999, vol. 19, Issue No. 10, pp. 7031-7040.
Roskos L.K., et al., "Measuring Immunity," Chapter 13—Human Antiglobulin Responses, Editor(s): Michael T. Lotze, Angus W. Thomson, Academic Press, London, United Kingdom, 2005, pp. 172-186, ISBN 9780124559004 [retrieved online: https://doi.org/10.1016/B978-012455900-4/50275-0].

Rosner K., et al., "Third Complementarity-Determining Region of Mutated VH Immunoglobulin Genes Contains Shorter V, D, J, P, and N Components than Non-Mutated Genes," Immunology, 2001, vol. 103 (2), pp. 179-187.
Rothstein R., "Targeting, Disruption, Replacement, and Allele Rescue: Integrative DNA Transformation in Yeast," Methods in Enzymology, 1991, vol. 194, pp. 281-301.
Rourke J., Declaration of Jeffrey Rourke, Registered Patent Attorney for Regeneron Pharmaceuticals, Inc.—In the matter of Patent Acceptance 2011266843 in the Name of Kymab Limited and In the Matter of Opposition thereto by Regeneron Pharmaceuticals, Inc., dated Jan. 29, 2016, 5 pages.
Rubinstein M., et al., "Introduction of a Point Mutation Into the Mouse Genome by Homologous Recombination in Embryonic Stem Cells Using a Replacement Type Vector With a Selectable Marker," Nucleic Acids Research, Jun. 1993, vol. 21(11), pp. 2613-2617.
Rudolf M.P., et al., "Molecular basis for nonanaphylactogenicity of a monoclonal anti-IgE antibody," Journal of Immunology, Jul. 2010, vol. 165 (2), pp. 813-819.
Ruiz M., et al., "The Human Immunoglobulin Heavy Diversity (IGHD) and Joining (IGHJ) Segments," Experimental and Clinical Immunogenetics, 1999, vol. 16, pp. 173-184.
Rusk N., "Making Mice at High Speed," Nature Methods, Mar. 2007, vol. 4 (3), pp. 196-197.
Russell N.D., et al., "Production of Protective Human Antipneumococcal Antibodies by Transgenic Mice with Human Immunoglobulin Loci," Infection and Immunity, Apr. 2000, vol. 68 (4), pp. 1820-1826.
Sabbattini P., et al., "Analysis of Mice with Single and Multiple Copies of Transgenes Reveals a Novel Arrangement for the λ5-VpreB1 Locus Control Region," Molecular and Cellular Biology, Jan. 1999, vol. 19 (1), pp. 671-679.
Sabouri, Z., et al., "Redemption of autoantibodies on anergic B cells by variable-region glycosylation and mutation away from self-reactivity," Proceedings of the National Academy of Sciences of the United States of America, Early Edition, May 2014, pp. E2567-E2575.
Sakai E., et al., "Recombination and Transcription of the Endogenous Ig Heavy Chain Locus is Effected by the Ig Heavy Chain Intronic Enhancer Core Region in the Absence of the Matrix Attachment Regions," Proceedings of the National Academy of Sciences of the U.S.A., 1999, vol. 96 (4), pp. 1526-1531.
Sarkar A., et al., "Molecular Evolutionary Analysis of the Widespread PiggyBac Transposon Family and Related "Domesticated" Sequences," Molecular Genetics & Genomics, 2003, vol. 270 (2), pp. 173-180.
Sasso E.H., et al., "Ethnic Differences of Polymorphism of an Immunoglobulin VH3 Gene," Journal of Clinical Investigation, 1995, vol. 96 (3), pp. 1591-1600.
Sasso E.H., et al., "Expression of the Immunoglobulin VH Gene 51p1 is Proportional to its Germline Gene Copy Number," Journal of Clinical Investigation, 1996, vol. 97 (9), pp. 2074-2080.
Sauer B., "Functional Expression of the cre-lox Site-Specific Recombination System in the Yeast Saccharomyces cerevisiae," Molecular and Cellular Biology, 1987, vol. 7 (6), pp. 2087-2096.
Sauer B., et al., "Cre-Stimulated Recombination at loxP-Containing DNA Sequences Placed into the Mammalian Genome," Nucleic Acids Research, 1989, vol. 17 (1), pp. 147-161.
Geurts A.M., et al., "Knockout Rats via Embryo Microinjection of Zinc-Finger Nucleases," Science, 2009, vol. 325 (5939), p. 433.
Giallourakis C.C., et al., "Elements Between the IgH Variable (V) and Diversity (D) Clusters Influence Antisense Transcription and Lineage-Specific V(D)J Recombination," Proceedings of the National Academy of Sciences of the U.S.A., 2010, vol. 107 (51), pp. 22207-22212.
Gibson D.G., et al., "Complete Chemical Synthesis, Assembly, and Cloning of a Mycoplasma genitalium Genome," Science, Feb. 2008, vol. 319, pp. 1215-1220.
Giraldo P., et al., "Size Matters: Use of YACs, BACs and PACs in Transgenic Animals," Transgenic Research, 2001, vol. 10 (2), pp. 83-103.

(56) References Cited

OTHER PUBLICATIONS

Giudicelli V., et al., "IMGT/GENE-DB: a comprehensive database for human and mouse immunoglobulin and T cell receptor genes," Nucleic Acids Research, 2005, vol. 33, pp. D256-D261.

Giusti A.M., et al., "Hypermutation is Observed only in Antibody H Chain V Region Transgenes that have Recombined with Endogenous Immunoglobulin H DNA: Implications for the Location of cis-acting Elements Required for Somatic Mutation," The Journal of Experimental Medicine, Mar. 1993, vol. 177 (3), pp. 797-809.

Glanville J., et al., "Naive Antibody Gene-Segment Frequencies are Heritable and Unaltered by Chronic Lymphocyte Ablation," Proceedings of the National Academy of Sciences of the U.S.A, Dec. 2011, vol. 108 (50), pp. 20066-20071.

Glaser S. et al., "Current issues in mouse genome engineering," Nature Genetics, Nov. 2005, Vo. 37 (11), pp. 1187-1193.

Gluzman Y., "SV40-Transformed Simian Cells Support the Replication of Early SV40 Mutants," Cell, 1981, vol. 23 (1), pp. 175-182.

Goding J.W., "Differences Between Conventional and Monoclonal Serology," Monoclonal Antibodies: Principles and Practice, Production and Application of Monoclonal Antibodies in Cell Biology, Biochemistry and Immunology, 1996, Third Edition, Section 7.3, pp. 129-130.

Goldman I.L., et al., "Transgenic Animals in Medicine: Integration and Expression of Foreign Genes, Theoretical and Applied Aspects," Medical Science Monitor, 2004, vol. 10 (11), pp. RA274-RA285.

Gondo Y., et al., Next-generation gene targeting in the mouse for functional genomics, BMB reports, Jul. 2009, vol. 42(6), pp. 315-323.

Goodhardt M., et al., "Rearrangement and Expression of Rabbit Immunoglobulin κ Light Chain Gene in Transgenic Mice," Proceedings of the National Academy of Sciences of the U.S.A., 1987, vol. 84 (12), pp. 4229-4233.

Goodnow, Christopher Carl, Declaration (Evidence in Support of Opposition thereto by Regeneron Pharmaceuticals. Inc.) for Application No. 2011266843, dated Jan. 29, 2016, 21 pages.

Goodnow, Christopher Carl, Second Declaration (Evidence in Support of Opposition thereto by Regeneron Pharmaceuticals, Inc.) for Application No. 2011266843, dated Jul. 4, 2016, 9 pages.

Goodnow, Christopher Carl, Third Declaration (Evidence in Support of Opposition thereto by Regeneron Pharmaceuticals, Inc.) for Application No. 2011266843, dated Aug. 29, 2017, 7 pages.

Gorman J.R., et al., "The IgK 3' Enhancer Influences the Ratio of Igκ Versus Igλ B lymphocytes," Immunity, Sep. 1996, vol. 5, pp. 241-252.

Gorny M.K., et al., "Human Anti-V3 HIV-1 Monoclonal Antibodies Encoded by the VH5-51/VL Lambda Genes Define a Conserved Antigenic Structure," PLoS One, Dec. 2011, vol. 6 (12), pp. e27780-1-e27780-10.

Goyenechea B., et al., "Cells Strongly Expressing IgK Transgenes Show Clonal Recruitment of Hypermutation: A Role for Both MAR and the Enhancers," EMBO Journal, 1997, vol. 16 (13), pp. 3987-3994.

Grandea A.G., III., et al., "Human antibodies reveal a protective epitope that is highly conserved among human and honhuman influenza A viruses," Proceedings of the National Academy of Sciences of the U.S.A., Jul. 2010, vol. 107 (28), pp. 12658-12663.

Gratz S. et al., "Genome Engineering of Drosophila with the CRISPR RNA-Guided Cas9 Nuclease," Genetics, Aug. 2013, vol. 194, pp. 1029-1035.

Green L.L., "Antibody Engineering via Genetic Engineering of the Mouse: XenoMouse Strains are a Vehicle for the Facile Generation of Therapeutic Human Monoclonal Antibodies," Journal of Immunological Methods, Dec. 1999, vol. 231 (1-2), pp. 11-23.

Green L.L., et al., "Antigen Specific Human Monoclonal Antibodies From Mice Engineered with Human Ig Heavy and Light Chain YACs," Nature Genetics, May 1994, vol. 7 (1), pp. 13-21.

Green L.L., et al., "Regulation of B Cell Development by Variable Gene Complexity in Mice Reconstituted with Human Immunoglobulin Yeast Artificial Chromosomes," The Journal of Experimental Medicine, Aug. 1998, vol. 188 (3), pp. 483-495.

Grippo V., et al., "The Heavy Chain Variable Segment Gene Repertoire in Chronic Chagas' Heart Disease," The Journal of Immunology, Dec. 2009, vol. 182 (12), pp. 8015-8025.

Grund M., European Patent Attorney, Grund Intellectual Property Group, Third-Party Observations according to Article 115 EPC regarding 18153154.2, dated Mar. 18, 2022, 3 pages.

Grund M., European Patent Attorney, Grund Intellectual Property Group, Third-Party Observations according to Article 115 EPC regarding 11705964.2, dated Apr. 30, 2014, 4 pages.

Grund M., European Patent Attorney, Grund Intellectual Property Group, Third-Party Observations according to Article 115 EPC regarding 11705964.2, dated Aug. 5, 2016, 11 pages.

Grund M., European Patent Attorney, Grund Intellectual Property Group, Third-Party Observations according to Article 115 EPC regarding 11705964.2, dated Feb. 26, 2015, 5 pages.

Grund M., European Patent Attorney, Grund Intellectual Property Group, Third-Party Observations according to Article 115 EPC regarding 11705964.2, dated Oct. 9, 2013, 8 pages.

Grund M., European Patent Attorney, Grund Intellectual Property Group, Third-Party Observations according to Article 115 EPC regarding 12171791.2, dated Aug. 4, 2014, 6 pages.

Grund M., European Patent Attorney, Grund Intellectual Property Group, Third-Party Observations according to Article 115 EPC regarding 12171791.2, dated Dec. 19, 2014, 7 pages.

Grund M., European Patent Attorney, Grund Intellectual Property Group, Third-Party Observations according to Article 115 EPC regarding 12171791.2, dated Feb. 26, 2014, 9 pages.

Grund M., European Patent Attorney, Grund Intellectual Property Group, Third-Party Observations according to Article 115 EPC regarding 12171793.8, dated Jun. 25, 2014, 7 pages.

Grund M., European Patent Attorney, Grund Intellectual Property Group, Third-Party Observations according to Article 115 EPC regarding 12171793.8, dated Mar. 17, 2015, 4 pages.

Grund M., European Patent Attorney, Grund Intellectual Property Group, Third-Party Observations according to Article 115 EPC regarding 12171793.8, dated May 22, 2015, 5 pages.

Grund M., European Patent Attorney, Grund Intellectual Property Group, Third-Party Observations according to Article 115 EPC regarding 12171793.8, dated Oct. 10, 2013, 10 pages.

Grund M., European Patent Attorney, Grund Intellectual Property Group, Third-Party Observations according to Article 115 EPC regarding 12194970.5, dated Apr. 25, 2014, 6 pages.

Grund M., European Patent Attorney, Grund Intellectual Property Group, Third-Party Observations according to Article 115 EPC regarding 12194970.5, dated Aug. 12, 2014, 5 pages.

Grund M., European Patent Attorney, Grund Intellectual Property Group, Third-Party Observations according to Article 115 EPC regarding 12194970.5, dated Mar. 5, 2014, 9 pages.

Grund M., European Patent Attorney, Grund Intellectual Property Group, Third-Party Observations according to Article 115 EPC regarding 12194970.5, dated Nov. 15, 2013, 6 pages.

Grund M., European Patent Attorney, Grund Intellectual Property Group, Third-Party Observations according to Article 115 EPC regarding 12194970.5, dated Sep. 9, 2013, 11 pages.

Grund M., European Patent Attorney, Grund Intellectual Property Group, Third-Party Observations according to Article 115 EPC regarding 12194977.0, dated Mar. 26, 2014, 4 pages.

Grund M., European Patent Attorney, Grund Intellectual Property Group, Third-Party Observations according to Article 115 EPC regarding 12194977.0, dated May 12, 2015, 5 pages.

Grund M., European Patent Attorney, Grund Intellectual Property Group, Third-Party Observations according to Article 115 EPC regarding 12195041.4, dated Jul. 30, 2014, 5 pages.

Grund M., European Patent Attorney, Grund Intellectual Property Group, Third-Party Observations according to Article 115 EPC regarding 12762377.5, dated Feb. 12, 2016, 8 pages.

Grund M., European Patent Attorney, Grund Intellectual Property Group, Third-Party Observations according to Article 115 EPC regarding 12762377.5, dated Jun. 20, 2017, 4 pages.

Grund M., European Patent Attorney, Grund Intellectual Property Group, Third-Party Observations according to Article 115 EPC regarding 12762377.5, dated May 22, 2015, 7 pages.

(56) References Cited

OTHER PUBLICATIONS

Grund M., European Patent Attorney, Grund Intellectual Property Group, Third-Party Observations according to Article 115 EPC regarding 12762378.3, dated Feb. 15, 2017, 6 pages.

Grund M., European Patent Attorney, Grund Intellectual Property Group, Third-Party Observations according to Article 115 EPC regarding 12772122.3, dated Mar. 12, 2015, 5 pages.

European Patent Office, Notice of Opposition, together with Ground of Opposition and accompanying cited documents, related to European Patent EP3128009 in the name of Kymab Limited pertaining to Application No. 16189625.3, dated May 6, 2021, 55 pages.

European Patent Office, Opposition against EP 2758535 Antibodies, Variable Domains and Chains Tailored for Human Use in the name of Kymab Limited pertaining to Application No. 12772122.3, dated Aug. 9, 2017, 75 pages.

European Patent Office, Opposition against EP 2798950 Animal Models and Therapeutic Molecules in the hame of Kymab Limited pertaining to Application No. 14170196.1, dated Jan. 18, 2018, 33 pages.

European Patent Office, Opposition against EP2421357 Animal Models and Therapeutic Molecules in the name of Kymab Limited pertaining to Application No. 10734546.4, dated Jan. 23, 2013, 41 pages.

European Patent Office, Opposition against EP2421357 Animal Models and Therapeutic Molecules in the hame of Kymab Limited pertaining to Application No. 10734546.4, dated Oct. 23, 2013, 44 pages.

European Patent Office, Opposition against EP2604110 Animal Models and Therapeutic Molecules in the name of Kymab Limited pertaining to Application No. 12194777.0, dated Aug. 28, 2017, 73 pages.

European Patent Office, Statement of Fact and Arguments in Support of Opposition against EP2421357 Animal Models and Therapeutic Molecules in the name of Kymab Limited pertaining to Application No. 10734546.4, dated Oct. 22, 2013, 41 pages.

European Patent Office, Invitation to Pay Additional Fees and, Where Applicable, Protest Fee, Application No. PCT/GB2012/052296, mailed on Jan. 24, 2013, 9 pages.

Evans J.P., "Fertilin β and Other ADAMs as Integrin Ligands: Insights into Cell Adhesion and Fertilization," Bioessays, 2001, vol. 23 (7), pp. 628-639.

Evans M.J., Declaration of Martin J. Evans with appendices, dated Dec. 23, 2016, 99 pages.

Ewert, H.T. et al., "Biophysical Properties of human antibody variable domains," J. Mol. Biol., Jan. 2003, vol. 325 (3), pp. 531-553.

Featherstone K., et al., "The Mouse Immunoglobulin Heavy Chain V-D Intergenic Sequence Contains Insulators that May Regulate Ordered V(D)J Recombination," Journal of Biological Chemistry, 2010, vol. 285 (13), pp. 9327-9338.

Feeney A.J., "Genetic and Epigenetic Control of V Gene Rearrangement Frequency," Advances in Experimental Medicine and Biology, Chapter 6, 2009, vol. 650, pp. 73-81.

Fell H.P. et al., "Homologous Recombination in Hybridoma Cells: Heavy Chain Chimeric Antibody Produced by Gene Targeting," Proceedings of the National Academy of Sciences of the U.S.A, 1989, vol. 86 (21), pp. 8507-8511.

Feng Y.Q., et al., "Site-Specific Chromosomal Integration in Mammalian Cells: Highly Efficient CRE Recombinase-Mediated Cassette Exchange," Journal of Molecular Biology, 1999, vol. 292 (4), pp. 779-785.

Feschotte C., et al., "DNA Transposons and the Evolution of Eukaryotic Genomes," Annual Review of Genetics, 2007, vol. 41, pp. 331-368.

Festing, M.F.W., et al., "Revised nomenclature for strain 129 mice," Mammalian Genome, 1999, vol. 10, p. 836.

Finn C.A., "Reproductive Capacity and Litter Size In Mice: Effect of Age and Environment," J. Reprod. Fertil., 1963, vol. 6, pp. 205-214.

Fleischer B., et al., "Reactivity of Mouse T-Cell Hybridomas Expressing Human Vβ Gene Segments With Staphylococcal and Streptococcal Superantigens," Infection and Immunity, Mar. 1996, vol. 64 (3), pp. 987-994.

Folger K.R., et al., "Patterns of Integration of DNA Microinjected into Cultured Mammalian Cells: Evidence for Homologous Recombination Between Injected Plasmid DNA Molecules," Molecular and Cellular Biology, 1982, vol. 2 (11), pp. 1372-1387.

Forconi F., et al., "The Normal IGHV1-69-Derived B-Cell Repertoire Contains Stereotypic Patterns Characteristic of Unmutated CLL," Blood, 2010, vol. 115 (1), pp. 71-77.

Forsman A., et al., "Llama Antibody Fragments with Cross-Subtype Human Immunodeficiency Virus Type I (HIV-1)-Neutralizing Properties and High Affinity for HIV-1 gp120," Journal of Virology, Dec. 2008, vol. 82 (24), pp. 12069-12081.

Fraser M.J., et al., "Precise excision of TTAA-specific lepidopteran transposons piggyBac (IFP2) and tagalong (TFP3) from the baculovirus genome in cell lines from two species of Lepidoptera," Insect. Molecular Biology, 1996, vol. 5, Issue No. 2, pp. 141-151.

Fraser, N., et al., "The VH gene repertoire of splenic B cells and somatic hypermutation in systemic lupus erythematosus, " Arthritis Research and Therapy, 2003, vol. 5, Issue No. 2, pp. R114-R121.

French Patent Office, INPI, Laurent Deleu, Authorized officer, International Search Report for Patent Application No. 1359518, dated Aug. 20, 2014, 3 pages.

Friedrich G., Statement of Dr. Glenn Friedrich, dated Mar. 3, 2016, 4 pages.

Friedrich G., Statement of Dr. Glenn Friedrich, dated Mar. 31, 2014, 9 pages.

Friedrich G., Statement of Dr. Glenn Friedrich, dated Oct. 16, 2014, 9 pages.

Frigerio B., et al., "Antibody Engineering as Opportunity for Selection and Organization of Anti-HIV Therapeutic Agents," The Open Autoimmunity Journal, 2010, vol. 2, pp. 127-138.

Fujieda S., et al., "Multiple Types of Chimeric Germ-Line Ig Heavy Chain Transcripts in Human B Cells: Evidence for Trans-Splicing of Human Ig RNA," Journal of Immunology, 1996, vol. 157 (8), pp. 3450-3459.

Fukita Y., et al., "Somatic Hypermutation in the Heavy Chain Locus Correlates with Transcription," Immunity, 1998, vol. 9 (1), pp. 105-114.

Gallo M.L., et al., "The Human Immunoglobulin Loci Introduced into Mice: V (D) and J Gene Segment Usage Similar to that of Adult Humans," European Journal of Immunology, 2000, vol. 30 (2), pp. 534-540.

Gama Sosa M.A., et al., "Animal Transgenesis: An Overview," Brain Structure and Function, 2010, vol. 214 (2-3), pp. 91-109.

Gavilondo J.V., et al., "Antibody Engineering at the Millennium," BioTechniques, Jul. 2000, vol. 29 (1), pp. 128-145.

Genbank "Immunoglobulin Heavy Chain Variable Region (*Homo sapiens*)," Accession No. BAA75060, dated Jul. 2, 2008, 1 page.

Genbank (D. Muzny et al.), "Rattus norvegicus clone CH230-30N12, * Sequencing in Progress * , 6 unordered pieces," Accession No. AC111740, Nov. 9, 2002, 42 pages. [Retrieved from the Internet: http://www.ncbi.nlm.nih.gov/nuccore/AC111740 on Feb. 28, 2013].

Genbank, "DNA Sequence of the Human Immunoglobulin D Segment Locus," Accession No. x97051.1 S64822, dated Aug. 6, 2014, 29 pages. [Retrieved from the Internet: http://www.ncbi.nlm.nih.gov/nuccore/X97051].

Genbank, "DNA Sequence of the Human Immunoglobulin D Segment Locus," Accession No. x97051.1 S64822, dated Mar. 3, 2015 (Updated version), 26 pages.

Genbank, "*H.sapiens* immunoglobulin heavy chain J region, B1C haplotype," Accession No. X86356, 2 pages.

Genbank, "*Homo sapiens* DNA, immunoglobulin heavy-chain variable region, complete sequence, 5 of 5," AB019441.1, dated Jun. 18, 2018, 36 pages.

Genbank, *Homo sapiens* immunoglobulin heavy chain (IGH.1@) on chromosome 14, NCBI Ref. Sequence No. NG_001019.1, dated Jun. 26, 2002, 261 pages.

(56) References Cited

OTHER PUBLICATIONS

Genbank, "*Homo sapiens* immunoglobulin heavy-chain (IGHV2-5) gene, IGHV2-5*10 allele, partial sequence," Accession No. KF698731. 1, dated Nov. 18, 2013, 1 page.

Genbank, "*Homo sapiens* partial IGHJ6 gene for immunoglobulin heavy joining 6, exon 1, allele 4," Accession No. AJ879487.1, dated Jul. 26, 2016, 1 page.

Genbank, "Human Ig germline J6-region, partial cds," Accession No. M63030, 1 page.

Genbank, Mus musculus immunoglobulin heavy chain locus constant region and partial variable region, strain 129S1, NCBI Reference Sequence No. AJ851868.3, dated Jul. 26, 2007, 23 pages.

Genbank, "Mus musculus Ig kappa germline J-C region: J1-5 and C genes, and flanks," GenBank No. L80040.1, dated Sep. 2, 2003, 5 pages.

Genbank, "Mus musculus strain 129S1/SvlmJ chromosome 12 genomic sca locus group 129S1/SvlmJ 129S1/SVIMJ_MMCHR12_CTG1," NCBI Reference Sequence No. NT_114985.3, dated May 5, 2014, 1 page.

Genecards, "IGKV1-13 Gene—Immunoglobulin Kappa Va . . . Pseudogene," IGKV1-13 Gene—GeneCards | IGKV1-13 Pseudogene, dated Nov. 4, 2021, 14 pages [retreived online Apr. 11, 2021, https://www.genecards.org/cgi-bin/carddisp.pl?gene=IGKV1-13].

Gerdes T., et al., "Physical Map of the Mouse λ Light Chain and Related Loci," Immunogenetics, 2002, vol. 54 (1), pp. 62-65.

Gerstein R.M., et al., "Isotype Switching of an Immunoglobulin Heavy Chain Transgene Occurs by DNA Recombination Between Different Chromosomes," Cell, 1990, vol. 63 (3), pp. 537-548.

Van Dijk, Marcus, Third Declaration (Evidence in Support of Opposition thereto by Regeneron Pharmaceuticals, Inc. for Application No. 2011266843), dated Mar. 28, 2018, 6 pages.

Van Loo, P.F., et al., "Surrogate-Light-Chain Silencing Is Not Critical for the Limitation of Pre-B Cell Expansion but Is for the Termination of Constitutive Signaling," Immunity, Sep. 2007, vol. 27, pp. 468-480.

Van Snick J.L., et al., "Genetic Control of Rheumatoid Factor Production in the Mouse. Role of Genes Linked to the Immunoglobulin Heavy Chain Locus and to the Major Histocompatibility Complex," Arthritis and Rheumatism, Sep. 1983, vol. 26 (9), pp. 1085-1090.

Van Spriel A.B., et al., "Immunotherapeutic Perspective for Bispecific Antibodies," Immunology Today, 2000, vol. 21 (8), pp. 391-397.

Vasicek T.J., et al., "Structure and Expression of the Human Immunoglobulin λ Genes," The Journal of Experimental Medicine, 1990, vol. 172 (2), pp. 609-620.

Vassilieva S., et al., "Establishment of SSEA-1- and Oct-4-Expressing Rat Embryonic Stem-Like Cell Lines and Effects of Cytokines of the IL-6 Family on Clonal Growth," Experimental Cell Research, 2000, vol. 258 (2), pp. 361-373.

Venken K.J.T., et al., "P[acman]: a BAC Transgenic Platform for Targeted Insertion of Large DNA Fragments in *D. Melanogaster*," Science, 2006, vol. 314 (5806), pp. 1747-1751.

Vieira P., et al., "The half-lives of serum immunoglobulins in adult mice," European Journal of Immunology, 1988, vol. 18, pp. 313-316.

Vollmer J., et al., "Antigen Contacts by Ni-Reactive TCR: Typical αβ Chain Cooperation Versus α Chain-Dominated Specificity," International Immunology, 2000, vol. 12 (12), pp. 1723-1731.

Volpe J.M., et al., "Large-scale analysis of human heavy chain V(D)J recombination patterns," Immunome Research, 2008, vol. 4, Issue No. 3, 10 pages.

Vora K.A., et al., "Altering the Antibody Repertoire via Transgene Homologous Recombination: Evidence for Global and Clone-Autonomous Regulation of Antigen-Driven B Cell Differentiation," The Journal of Experimental Medicine, 1995, vol. 181 (1), pp. 271-281.

Voronina V.A., et al., "Deletion of Adam6 in Mus musulus leads to male subfertility an deficits in sperm ascent into the oviduct," Biology of Reproduction, 2019, vol. 100, Issue No. 3, pp. 686-696.

Wagner S.D., et al., "Antibodies Generated from Human Immunoglobulin Miniloci in Transgenic Mice," Nucleic Acids Research, 1994, vol. 22 (8), pp. 1389-1393.

Wagner, S., et al., "The diversity of antigen-specific monoclonal antibodies from transgenic mice bearing human immunoglobulin gene miniloci," European Journal of Immunology 1994, vol. 24, pp. 2672-2681.

Wallace H.A.C., et al., "Manipulating the Mouse Genome to Engineer Precise Functional Syntenic Replacements with Human Sequence," Cell, Jan. 2007, vol. 128 (1), pp. 197-209.

Wang M., et al., "AID Upmutants Isolated Using a High-Throughput Screen Highlight the Immunity/Cancer Balance Limiting DNA Deaminase Activity," Nature Structural & Molecular Biology, 2009, vol. 16 (7), pp. 769-776.

Wang M., et al., "Altering the Spectrum of Immunoglobulin V Gene Somatic Hypermutation by Modifying the Active Site of AID," The Journal of Experimental Medicine, 2010, vol. 207 (1), pp. 141-153.

Wang T.T., et al., "Catching a Moving Target," Science, 2011, vol. 333 (6044), pp. 834-835.

Wang W., et al., "Chromosomal Transposition of PiggyBac in Mouse Embryonic Stem Cells," Proceedings of the National Academy of Sciences of the U.S.A., 2008, vol. 105 (27), pp. 9290-9295.

Wang X., et al., "Recombination, transcription, and diversity of a partially germline-joined VH in a mammal," Immunogenetics, 2012, vol. 64, pp. 713-717.

Wang Y., et al., "Many Human Immunoglobulin Heavy-Chain IGHV Gene Polymorphisms have been Reported in Error," Immunology and Cell Biology, 2008, vol. 86 (2), pp. 111-115.

Wasserman R., et al., "The Pattern of Joining (JH) Gene Usage in the Human IgH Chain Is Established Predominantly at the B PreCursor Cell Stage," The Journal of Immunology, Jul. 1992, vol. 149 (2), pp. 511-516.

Waterhouse P., et al., "Combinatorial Infection and in Vivo Recombination: a Strategy for Making Large Phage Antibody Repertoires," Nucleic Acids Research, 1993, vol. 21 (9), pp. 2265-2266.

Waterston R.H., et al., "Initial Sequencing and Comparative Analysis of the Mouse Genome," Nature, Dec. 2002, vol. 420 (6915), pp. 520-562.

Webpage corroborating non-confidential nature of 2006 MUGEN Conference, Athens (www.mugen.noe.org), accessed Aug. 9, 2016, 4 pages.

Weichhold G.M., et al., "Megabase Inversions in the Human Genome as Physiological Events," Nature, Sep. 1990, vol. 347 (6288), pp. 90-92.

Weichhold G.M., et al., "The Human Immunoglobulin ? Locus Consists of Two Copies that are Organized in Opposite Polarity," Genomics, 1993, vol. 16 (2), pp. 503-511.

Weiner L.M., "Fully Human Therapeutic Monoclonal Antibodies," Journal of Immunology, Jan./Feb. 2006, vol. 29 (1), pp. 1-9.

West, J., et al., "Genome Editing in Large Animals," J Equine Vet Sci. 2016, 41, pp. 1-6.

White J.K., et al., "Genome-Wide Generation and Systematic Phenotyping of Knockout Mice Reveals New Roles for Many Genes," Cell, 2013, vol. 154 (2), pp. 452-464.

Wikipedia, "Monoclonal antibody," 2008, 8 pages.

Wikipedia, "Polyclonal antibodies," 2008, 5 pages.

Wilke K., et al., "Diagnosis of Haploidy and Triploidy Based on Measurement of Gene Copy Number by Real-Time PCR," Human Mutation, 2000, vol. 16 (5), pp. 431-436.

Wilkie T.M., et al., "Analysis of the Integrant in MyK-103 Transgenic Mice in which Males Fail to Transmit the Integrant," Molecular and Cellular Biology, 1987, vol. 7 (5), pp. 1646-1655.

Williams G.S., et al., "Unequal VH Gene Rearrangement Frequency within the Large VH7183 Gene Family is not due to Recombination Signal Sequence Variation, and Mapping of the Genes Shows a Bias of Rearrangement Based on Chromosomal Location," Journal of Immunology, 2001, vol. 167 (1), pp. 257-263.

Williams K., Attorney for Applicant, Third-Party Pre-Issuance Submission Under 37 CFR 1.290 in U.S. Appl. No. 14/600,829, dated Apr. 1, 2016, 18 pages.

Williams K., Attorney for Applicant, Third-Party Pre-Issuance Submission Under 37 CFR 1.290 in U.S. Appl. No. 14/679,949, dated Apr. 1, 2016, 18 pages.

(56)		References Cited

OTHER PUBLICATIONS

Wilson, M.H., et al., "PiggyBack Transposon-mediated Gene Transfer in Human Cells, The American Society of Gene Therapy, Molecular Therapy," Jan. 2007, vol. 15, Issue No. 1, pp. 136-145.
Woloschak G.E., et al., "Regulation of ? / ? Immunoglobulin Light Chain Expression in Normal Murine Lymphocytes, " Molecular Immunology, 1987, vol. 24, Issue No. 7, pp. 751-757.
Woltjen K. et al., "piggyBac transposition reprograms fibroblast to induced pluripotent stem cells," Nature, Apr. 2009, vol. 458, pp. 766-771.
Wooddard L.E.et al., "piggyBac-ing models and new therapeutic strategies," Trends in Biotechnology, Sep. 2015, vol. 33, Issue No. 9, pp. 525-533.
Wozniak-Knopp G., et al., "Introducing antigen-binding sites in structural loops of immunoglobulin constant domains: Fc fragments with engineered HER2/neu-binding sites and antibody properties," Protein Engineering Design & Selection, 2010, vol. 23(4), pp. 289-297.
Wu H., et al., "Double replacement: Strategy for efficient introduction of subtle mutations into the murine Colla-1 gene by homologous recombination in embryonic stem cells," Proc. National Academy of Sciences of the U.S.A., Mar. 1994, vol. 91, pp. 2819-2823.
Wuerffel R., et al., "S-S Synapsis During Class Switch Recombination is Promoted by Distantly Located Transcriptional Elements and Activation-Induced Deaminase," Immunity, Nov. 2007, vol. 27 (5), pp. 711-722.
Xiao X., et al., "Germline-like predecessors of broadly neutralizing antibodies lack measurable binding to HIV-1 envelope glycoproteins: Implications for evasion of immune responses and design of vaccine immunogens," Biochemical and Biophysical Communications, 2009, vol. 390, pp. 404-409.
Xu J.L., et al., "Diversity in the CDR3 Region of VH Is Sufficient for Most Antibody Specificities," Immunity, vol. 13, Jul. 2000, pp. 37-45.
Xu L., et al., "Combinatorial Surrobody Libraries," Proceedings of the National Academy of Sciences of the U.S.A., 2008, vol. 105 (31), pp. 10756-10761.
Xu Y., et al., "Deletion of the Igk Light Chain Intronic Enhancer/ Matrix Attachment Region Impairs but does not Abolish VkJk Rearrangement," Immunity, Apr. 1996, vol. 4 (4), pp. 377-385.
Xu Z., et al., "Site-specific recombination in Schizosaccharomyces pombe and systematic assembly of a 400kb transgene array iin mammalian cells using the integrase of Steptomyces phage ?Bt1," Nucleic Acids Research, Dec. 2007, vol. 36(1), pp. e9-1-e9-9.
Yamada M., et al., "Preferential Utilization of Specific Immunoglobulin Heavy Chain Diversity and Joining Segments in Adult Human Peripheral Blood B Lymphocytes," Journal of Experimental Medicine, Feb. 1991, vol. 173, pp. 395-407.
Lyon C., Attorney for Applicant, Third-Party Pre-Issuance Submission Under 37 CFR Sec. 1.290 in U.S. Appl. No. 14/040,427, dated Jan. 16, 2015, 20 pages.
Lyon C., Attorney for Applicant, Third-Party Pre-Issuance Submission Under 37 CFR Sec. 1.290 in U.S. Appl. No. 14/056,434, dated Dec. 15, 2014, 6 pages.
Lyon C., Attorney for Applicant, Third-Party Pre-Issuance Submission Under 37 CFR Sec. 1.290 in U.S. Appl. No. 14/056,700, dated Nov. 28, 2014, 6 pages.
Lyon C., Attorney for Applicant, Third-Party Pre-Issuance Submission Under 37 CFR Sec. 1.290 in U.S. Appl. No. 14/056,707, dated Nov. 28, 2014, 10 pages.
Lyon C., Attorney for Applicant, Third-Party Pre-Issuance Submission Under 37 CFR Sec. 1.290 in U.S. Appl. No. 14/080,630, dated Oct. 31, 2014, 8 pages.
Lyon C., Attorney for Applicant, Third-Party Pre-Issuance Submission Under 37 CFR Sec. 1.290 in U.S. Appl. No. 14/137,902, dated Nov. 13, 2014, 9 pages.
Lyon C., Attorney for Applicant, Third-Party Pre-Issuance Submission Under 37 CFR Sec. 1.290 in U.S. Appl. No. 14/220,080, dated Jul. 28, 2015, 28 pages.
Lyon C., Attorney for Applicant, Third-Party Pre-Issuance Submission Under 37 CFR Sec. 1.290 in U.S. Appl. No. 14/220,095, dated Aug. 4, 2015, 19 pages.
Lyon C., Attorney for Applicant, Third-Party Pre-Issuance Submission Under 37 CFR Sec. 1.290 in U.S. Appl. No. 14/220,099, dated Apr. 29, 2015, 43 pages.
Lyon C., Attorney for Applicant, Third-Party Pre-Issuance Submission Under 37 CFR Sec. 1.290 in U.S. Appl. No. 14/226,698, dated Jun. 3, 2015, 53 pages.
Lyon C., Attorney for Applicant, Third-Party Pre-Issuance Submission Under 37 CFR Sec. 1.290 in U.S. Appl. No. 14/226,706, dated Jul. 28, 2015, 53 pages.
Lyon C., Attorney for Applicant, Third-Party Pre-Issuance Submission Under 37 CFR Sec. 1.290 in U.S. Appl. No. 14/263,158, dated Apr. 29, 2015, 16 pages.
Lyon C., Attorney for Applicant, Third-Party Pre-Issuance Submission Under 37 CFR Sec. 1.290 in U.S. Appl. No. 14/263,176, dated Apr. 29, 2015, 16 pages.
Lyon C., Attorney for Applicant, Third-Party Pre-Issuance Submission Under 37 CFR Sec. 1.290 in U.S. Appl. No. 14/497,054, dated Oct. 21, 2015, 81 pages.
Lyon C., Attorney for Applicant, Third-Party Pre-Issuance Submission Under 37 CFR Sec. 1.290 in U.S. Appl. No. 14/498,685, dated Sep. 18, 2015, 37 pages.
Lyon C., Attorney for Applicant, Third-Party Pre-Issuance Submission Under 37 CFR Sec. 1.290 in U.S. Appl. No. 14/516,461, dated Aug. 4, 2015, 27 pages.
Lyon C., Attorney for Applicant, Third-Party Pre-Issuance Submission Under 37 CFR Sec. 1.290 in U.S. Appl. No. 14/543,359, dated Nov. 13, 2015, 36 pages.
Ma B., et al., "Human Antibody Expression in Transgenic Rats: Comparison of Chimeric IgH Loci with Human VH, D and JH but Bearing Different Rat C-Gene Regions," Journal of Immunological Methods, 2013, vols. 400-401, pp. 78-86.
MacDonald L., Curriculum Vitae of Lynn E. MacDonald, Ph.D., 3 pages.
MacDonald L., Declaration of Lynn E. MacDonald with Exhibits, dated Feb. 3, 2015, relating to International Application No. PCT/ US02/04500 (Published as WO02/066630 A1), 13 pages.
MacDonald L., Declaration of Lynne E. Macdonald, dated Jun. 29, 2016, 4 pages.
MacDonald L., Declaration of Lynne E. Macdonald, dated May 16, 2018, including Annex 1, 10 pages.
MacDonald L., et al., "Velocigene® Technology Extended to Humanization of Several Megabases of Complex Gene Loci," (Abstract-21) 1st International MUGEN Conference on Animal Models for Human Immunological Disease, Athens Greece, Sep. 10-13, 2006, 1 page.
MacDonald L., et al., Expanded Poster: "Velocigene® Technology Extended to Humanization of Several Megabases of Complex Gene Loci," Sep. 2006, 6 pages.
MacDonald L., et al., Poster (Exhibit IJR-47): "Velocigene® Technology Extended to Humanization of Several Megabases of Complex Gene Loci," and evidence of unavailability, Sep. 2006, 42 pages.
MacDonald L.E., et al., "Precise and in Situ Genetic Humanization of 6 Mb of Mouse Immunoglobulin Genes," Proceedings of the National Academy of Sciences of the U.S.A., 2014, vol. 111 (14), pp. 5147-5152.
Mack M., et al., "A Small Bispecific Antibody Construct Expressed as a Functional Single-Chain Molecule with High Tumor Cell Cytotoxicity," Proceedings of the National Academy of Sciences of the U.S.A., 1995, vol. 92 (15), pp. 7021-7025.
Magadán S., et al., "Production of Antigen-Specific Human Monoclonal Antibodies: Comparison of Mice IgH/κ or IgH/κ/λ transloci," Biotechniques, 2002, vol. 33 (3), pp. 680, 682, 684 passim.
Magdelaine-Beuzelin C., et al., "Structure-function relationships of the variable domains of monoclonal antibodies approved for cancer treatment," Critical Reviews in Oncology/Hematology, 2007, vol. 64, pp. 210-225.
Maitta R.W., et al., "Immunogenicity and Efficacy of Cryptococcus neoformans Capsular Polysaccharide Glucuronoxylomannan Peptide

(56)     References Cited

OTHER PUBLICATIONS

Mimotope-Protein Conjugates in Human Immunoglobulin Transgenic Mice," Infection and Immunity, 2004, vol. 72 (1), pp. 196-208.

Makris J.C., et al., "Mutational Analysis of Insertion Sequence 50 (IS50) and Transposon 5 (Tn5) Ends," Proceedings of the National Academy of Sciences of the U.S.A., 1988, vol. 85 (7), pp. 2224-2228.

Maksimenko O.G., et al., "Use of Transgenic Animals in Biotechnology: Prospect and Problems," ACTA Naturae, Reviews, 2013, vol. 5, Issue No. 1, pp. 33-46.

Mallender W.D., et al., "Construction, Expression, and Activity of a Bivalent Bispecific Single-Chain Antibody," The Journal of Biological Chemistry, 1994, vol. 269 (1), pp. 199-206.

Manis J.P., et al., "Mechanism and Control of Class-Switch Recombination," Trends in Immunology, 2002, vol. 23 (1), pp. 31-39.

Marcello M.R., et al., "Lack of Tyrosylprotein Sulfotransferase-2 Activity Results in Altered Sperm-Egg Interactions and Loss of ADAM3 and ADAM6 in Epididymal Sperm," The Journal of Biological Chemistry, 2011, vol. 286 (15), pp. 13060-13070.

Marchalonis J.J., et al., "Emergence of the immunoglobulin family: conservation in protein sequence and plasticity in gene organization," Glycobiology, vol. 6 (7), 1996, pp. 657-663.

Martínez P., et al., "Antibody Synthesis in Vitro," Encyclopedia of Life Sciences, 2005, pp. 1-8.

Martinez C., et al., "The Mouse (Mus musculus) Immunoglobulin Kappa Variable (IGKV) Genes and Joining (IGKJ) Segments," Experimental and Clinical Immunogenetics, Jul. 1998, vol. 15, pp. 184-193.

Martinez-Jean C., et al., "Nomenclature and Overview of the Mouse (Mus musculus and Mus sp.) Immunoglobulin Kappa (IGK) Genes," Experimental and Clinical Immunogenetics, 2001, vol. 18 (4), pp. 255-279.

Matthews V.B., et al., "A Locus Affecting Immunoglobulin Isotype Selection (Igis1) Maps to the MHC Region in C57BL, BALB/c and NOD Mice," Immunology and Cell Biology, 2001, vol. 79 (6), pp. 576-582.

Mattila P.S., et al., "Extensive Allelic Sequence Variation in the J Region of the Human Immunoglobulin Heavy Chain Gene Locus," European Journal of Immunology, 1995, vol. 25 (9), pp. 2578-2582.

Maul R.W., et al., "AID and Somatic Hypermutation," Advances in Immunology, Chapter 6, 2010, vol. 105, pp. 159-191.

McCreath K.J., et al., "Production of Gene-Targeted Sheep by Nuclear Transfer from Cultured Somatic Cells," Nature, 2000, vol. 405 (6790), pp. 1066-1069.

McMurry M.T., et al., "Enhancer Control of Local Accessibility to V(D)J Recombinase," Molecular and Cellular Biology, Aug. 1997, vol. 17 (8), pp. 4553-4561.

Meier I.D., et al., "Short DNA sequences inserted for gene targeting can accidentally interfere with off-target gene expression," The FASEB Journal, Research Communication, Jun. 2010, vol. 24, pp. 1714-1724.

Mejía J.E., et al., "The Assembly of Large BACs by in Vivo Recombination," Genomics, 2000, vol. 70 (2), pp. 165-170.

Mendez M.J., et al., "Functional Transplant of Megabase Human Immunoglobulin Loci Recapitulates Human Antibody Response in Mice," Nature Genetics, Feb. 1997, vol. 15 (2), pp. 146-156.

Merriam Webster Dictionary, Definition of "population" 2021, 8 pages [retrieved online: https://www.merriam-webster.com/dictionary/population].

Mester G., European Patent Attorney, Grund Intellectual Property Group, Third-Party Observations according to Article 115 EPC regarding 12778780.2, dated Sep. 30, 2016, 5 pages.

MGI, "Guidelines for Nomenclature of Mouse and Rat Strains," International Committee on Standardized Genetic Nomenclature for Mice / Rat Genome and Nomenclature Committee; Chairpersons: J.T. Eppig and G. Levan, Oct. 2011, 11 pages. [printed: Mar. 6, 2012—http://www.informatics.jax.org/mgihome/nomen/strains.shtml].

Kwon, K., et al., "Instructive role of E2A in early B lymphopoiesis and germinal center B cell development," Immunity 2008, vol. 28, No. 6, pp. 751-762.

Kwon, K., et al., "Supplemental Data Instructive role of E2A in early B lymphopoiesis and germinal center B cell development," Immunity 2008, vol. 28, 24 pages.

Köhrer C., et al., "Import of Amber and Ochre Suppressor IRNAs into Mammalian Cells: a General Approach to Site-Specific Insertion of Amino Acid Analogues into Proteins," Proceedings of the National Academy of Sciences of the U.S.A., 2001, vol. 98 (25), pp. 14310-14315.

Laffleur B., et al., "Production of Human or Humanized Antibodies in Mice," Methods in Molecular Biology, Chapter 9, 2012, vol. 901, pp. 149-159.

Largaespada D.A., "Transposon Mutagenesis in Mice," Methods in Molecular Biology, vol. 530, 2009, pp. 379-390.

Laventie B., et al., "Heavy Chain-Only Antibodies and Tetravalent Bispecific Antibody Neutralizing Staphylococcus aureus Leukotoxins," Proceedings of the National Academy of Sciences of the U.S.A., 2011, vol. 108 (39), pp. 16404-16409.

Law M., et al., "Antibodies Against Viruses: Passive and Active Immunization," Current Opinion in Immunology, Aug. 2008, vol. 20(4), pp. 486-492.

Le Mouellic H., et al., "Pattern of Transcription of the Homeo Gene Hox-3.1 in the Mouse Embryo," Genes & Development, 1988, vol. 2 (1), pp. 125-135.

Lee E., et al., "Complete Humanization of the Mouse Immunoglobulin Loci Enables Efficient Therapeutic Antibody Discovery," Nature Biotechnology, 2014, vol. 32 (4), pp. 356-363.

Lee E., et al., "The Application of Transgenic Mice for Therapeutic Antibody Discovery," Methods in Molecular Biology, Chapter 8, 2012, vol. 901, pp. 137-148.

Lee E., et al., "Use of IGHJ and IGHD gene mutations in analysis of immunoglobulin sequences for the prognosis of chronic lymphocytic leukemia," Leukemia Research, 2007, vol. 31, pp. 1247-1252.

Lee H., et al., "Human C5aR Knock-in Mice Facilitate the Production and Assessment of Anti-Inflammatory Monoclonal Antibodies," Nature Biotechnology, 2006, vol. 24 (10), pp. 1279-1284.

Lee, E-Chiang, "Declaration of E-Chiang Lee," Jun. 13, 2016, 8 pages.

Lefranc M., Appendix 1P, Abbreviations and Useful Data, "Nomenclature of the Human Immunoglobulin Genes," Current Protocols in Immunology, 2000, Supp. 40, pp. A.1P.1-A.1P.37.

Lefranc M.P., "Nomenclature of the Human Immunoglobulin Heavy (IGH) Genes," Experimental and Clinical Immunogenetics, 2001, vol. 18 (2), pp. 100-116.

Lefranc M.P., "Nomenclature of the Human Immunoglobulin Kappa (IGK) Genes," Experimental and Clinical Immunogenetics, 2001, vol. 18 (3), pp. 161-174.

Lefranc M.P., "Nomenclature of the Human Immunoglobulin Lambda (IGL) Genes," Experimental and Clinical Immunogenetics, 2001, vol. 18 (4), pp. 242-254.

Lefranc M.P., et al., "IGHJ group in Annex 3," The Immunoglobulin FactsBook, IMGT, the international ImMunoGeneTics database, May 2001, 4 pages (including cover sheet and copyright pages).

Lefranc M.P., et al., "Immunoglobulin Lambda (IGL) Genes of Human and Mouse," Molecular Biology of B Cells, Chapter 4, p. 47, 2004 (Edtrs. Honjo et al.).

Lefranc M.P., et al., Excerpts from "The Immunoglobulin FactsBook," IMGT, the international ImMunoGeneTics database, May 2001, 455 pages.

Lerner, R.A., "Rare antibodies from combinatorial libraries suggests an S.O.S. component of the human immunological repertoire," Mol. BioSyst., Apr. 2011, vol. 7(4), pp. 1004-1012.

Levin A.M., et al., "Optimizing the affinity and specificity of proteins with molecular display," Molecular Biosystems, 2006, vol. 2, pp. 49-57.

Li H., et al., "Genetic Diversity of the Human Immunoglobulin Heavy Chain VH Region," Immunological Reviews, Dec. 2002, vol. 190, pp. 53-68.

Li L., et al., "Transgenic Mice with a Diverse Human T Cell Antigen Receptor Repertoire," Nature Medicine, 2010, vol. 16 (9), pp. 1029-1034.

(56)         References Cited

OTHER PUBLICATIONS

Li M., Second Declaration of Dr. Meng (Amy) Li, dated Sep. 5, 2016, 2 pages.
Li M.A., et al., "Crafting Rat Genomes with Zinc Fingers," Nature Biotechnology, 2011, vol. 29 (1), pp. 39-41.
Li P., et al., "Germline Competent Embryonic Stem Cells Derived from Rat Blastocysts," Cell, 2008, vol. 135 (7), pp. 1299-1310.
Li X., et al., "The Minimum Internal and External Sequence Requirements for Transposition of the Eukaryotic Transformation Vector PiggyBac," Molecular Genetics & Genomics, 2001, vol. 266 (2), pp. 190-198.
Li Z., et al., "The generation of antibody diversity through somatic hypermutation and class switch recombination," Genes & Development, 2004, vol. 18, pp. 1-11.
Liang Q., et al., "Extensive genomic copy number variation in embryonic stem cells," Proceedings of the National Academy of Sciences of the U.S.A., Nov. 2008, vol. 105 (45), pp. 17453-17456.
Liao J., et al., "Generation of Induced Pluripotent Stem Cell Lines from Adult Rat Cells," Cell Stem Cell, 2009, vol. 4 (1), pp. 11-15.
Little M., et al., "Generation of a Large Complex Antibody Library from Multiple Donors," Journal of Immunological Methods, 1999, vol. 231 (1-2), pp. 3-9.
Little M., et al., "Of mice and men: hybridoma and recombinant antibodies," Review Immunology Today, Aug. 2000, vol. 21, Issue No. 8, pp. 364-370.
Liu L., et al., "IGH V3-23*01 and its allele V3-23*03 differ in their capacity to form the canonical human antibody combining site specific for the capsular polysaccharide of Haemophilus influenzae type b," Immunogenetics, 2003, vol. 55, pp. 336-338.
Liu L., et al., "Potent and Broad Anti-HIV-1 Activity Exhibited by a Glycosyl-Phosphatidylinositol-Anchored Peptide derived from the CDR H3 of Broadly Neutralizing Antibody PG16," Journal of Virology, 2011, vol. 85 (17), pp. 8467-8476.
Liu X., et al., "Trisomy Eight in ES Cells Is a Common Potential Problem in Gene Targeting and Interferes With Germ Line Transmission," Developmental Dynamics, vol. 209, 1997, pp. 85-91.
Logtenberg T., "Antibody Cocktails: Next-Generation Biopharmaceuticals With Improved Potency," Trends in Biotechnology, Sep. 2007, vol. 25(9), pp. 390-394.
Lonberg N., "Fully Human Antibodies from Transgenic Mouse and Phage Display Platforms," Current Opinion in Immunology, 2008, vol. 20 (4), pp. 450-459.
Lonberg N., "Human Antibodies from Transgenic Animals," Nature Biotechnology, Sep. 2005, vol. 23 (9), pp. 1117-1125.
Lonberg N., "Human Monoclonal Antibodies from Transgenic Mice," Therapeutic Antibodies. Handbook of Experimental Pharmacology, 2008, pp. 69-97.
Lonberg N., et al., "Antigen-specific human antibodies from mice comprising four distinct genetic modifications," Nature, Apr. 1994, vol. 368, pp. 856-859.
Lonberg N., et al., "Human Antibodies from Transgenic Mice," Intern. Rev. Immunol., 1995, vol. 13, pp. 65-93.
Loveslati B.Y., et al., "A Study of Gm Allotypes and Immunoglobulin Heavy Gamma IGHG Genes in Berbers, Arabs and Sub-Saharan Africans from Jerba Island, Tunisia," European Journal of Immunogenetics, 2001, vol. 28 (5), pp. 531-538.
Luby T.M., et al., "The p. Switch Region Tandem Repeats are Important, but not Required, for Antibody Class Switch Recombination," The Journal of Experimental Medicine, 2001, vol. 193 (2), pp. 159-168.
Luciw P.A., et al., "Location and Function of Retroviral and SV40 Sequences that Enhance Biochemical Transformation after Microinjection of DNA," Cell, 1983, vol. 33 (3), pp. 705-716.
Luo G., et al., "Chromosomal Transposition of a Tc1/Mariner-like Element in Mouse Embryonic Stem Cells," Proceedings of the National Academy of Sciences of the U.S.A., 1998, vol. 95 (18), pp. 10769-10773.
Lyon C., Attorney for Applicant, Third-Party Pre-Issuance Submission Under 37 CFR Sec. 1.290 in U.S. Appl. No. 13/846,672, dated Mar. 17, 2015, 32 pages.

Lyon C., Attorney for Applicant, Third-Party Pre-Issuance Submission Under 37 CFR Sec. 1.290 in U.S. Appl. No. 13/875,892, dated May 5, 2015, 49 pages.
Lyon C., Attorney for Applicant, Third-Party Pre-Issuance Submission Under 37 CFR Sec. 1.290 in U.S. Appl. No. 13/886,511, dated May 5, 2015, 18 pages.
Sauer B., et al., "Site-Specific DNA Recombination in Mammalian Cells by the Cre Recombinase of Bacteriophage P1," Proceedings of the National Academy of Sciences of the U.S.A., 1988, vol. 85 (14), pp. 5166-5170.
Scapini P., et al., "Myeloid Cells, BAFF, and IFN-λ Establish an Inflammatory Loop that Exacerbates Autoimmunity in Lyn-Deficient Mice," The Journal of Experimental Medicine, Jul. 2010, vol. 207 (8), pp. 1757-1773.
Scarselli, M., et al., "Epitope Mapping of a Bactericidal Monoclonal Antibody against the Factor H Binding Protein pf Neisseria meningitidis," The Journal of Molecular Biology, Feb. 2009, vol. 386(1), pp. 97-108.
Schaller, M et al., "The splenic autoimmune response to ADAMTS13 in thrombotic thrombocytopenia purpura contains recurrent antigen-binding CDR3 motifs," Blood, Nov. 2014, vol. 124(23), pp. 3469-3479.
Scherer S., et al., "Replacement of Chromosome Segments With Altered DNA Sequences Constructed in Vitro," Proc. Natl. Acad. Sci. USA, Oct. 1979, vol. 76(10), pp. 4951-4955.
Schlake T., et al., "Use of Mutated FLP Recognition Target (FRT) Sites for the Exchange of Expression Cassettes at Defined Chromosomal Loci," Biochemistry, 1994, vol. 33 (43), pp. 12746-12751.
Schnütgen F., et al., "A Directional Strategy for Monitoring Cre-Mediated Recombination at the Cellular Level in the Mouse," Nature Biotechnology, 2003, vol. 21 (5), pp. 562-565.
Schonewald S.L., Attorney for Applicant, Third-Party Pre-Issuance Submission Under 37 CFR Sec. 1.290 in U.S. Appl. No. 14/935,010, dated Aug. 19, 2016, 27 pages.
Schonewald, S.L., Attorney for Applicant, Third-Party Pre-Issuance Submission Under 37 CFR Sec. 1.290 in U.S. Appl. No. 14/220,074, dated Jul. 12, 2016, 46 pages.
Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.
Schonewald, S.L., Attorney for Applicant, Third-Party Pre-Issuance Submission Under 37 CFR Sec. 1.290 in U.S. Appl. No. 14/818,162, dated May 24, 2016, 47 pages.
Schonewald, Stephanie L., Choate Hall & Stewart LLP, Petition for Inter Parties Review—AIA Review No. IPR2019-01577, filed Sep. 20, 2019, 86 pages.
Schonewald, Stephanie L., Choate Hall & Stewart LLP, Petition for Inter Parties Review—AIA Review No. IPR2019-01578, filed Sep. 20, 2019, 83 pages.
Schonewald, Stephanie L., Choate Hall & Stewart LLP, Petition for Inter Parties Review—AIA Review No. IPR2019-01579, filed Sep. 20, 2019, 84 pages.
Schonewald, Stephanie L., Choate Hall & Stewart LLP, Petition for Inter Parties Review—AIA Review No. IPR2019-01580, filed Sep. 20, 2019, 87 pages.
Schonewald, Stephanie L., Choate Hall & Stewart LLP, Petition for Inter Parties Review—AIA Review No. IPR2020-00389, filed Jan. 3, 2020, 89 pages.
Schroeder Jr. H.W, et al., "Preferential Utilization of Conserved Immunoglobulin Heavy Chain Variable Gene Segments During Human Fetal Life," Proceedings of the National Academy of Sciences of the U.S.A., 1990, vol. 87 (16), pp. 6146-6150.
Schroeder, Jr. H.W., "Similarity and divergence in the development and expression of the mouse and human antibody repertoires," Developmental and Comparative Immunology, vol. 30, 2006, pp. 119-135.
Schröck E., et al., "Comparative Genomic Hybridization (CGH)-Detection of Unbalanced Genetic Aberrations Using Conventional and Micro-Array Techniques," Current Protocols in Cytometry, Chapter 8, 2001, Unit 8.12.1, Supplement 18, 30 pages.
Schweinfest C.W., et al., "A Heat-Shock-Inducible Eukaryotic Expression Vector," Gene, 1988, vol. 71 (1), pp. 207-210.

(56) References Cited

OTHER PUBLICATIONS

Scott C.T., "Mice with a Human Touch," Nature Biotechnology, 2007, vol. 25 (10), pp. 1075-1077.

Seals D.F., et al., "The ADAMs Family of Metalloproteases: Multidomain Proteins with Multiple Functions," Genes & Development, 2003, vol. 17 (1), pp. 7-30.

Seed B., "Purification of Genomic Sequences from Bacteriophage Libraries by Recombination and Selection in Vivo," Nucleic Acids Research, 1983, vol. 11 (8), pp. 2427-2445.

Seidl K.J., et al., "An Expressed neor Cassette Provides Required Functions of the 1Y2b Exon for Class Switching," International Immunology, 1998, vol. 10 (11), pp. 1683-1692.

Seidl K.J., et al., "Position-Dependent Inhibition of Class-Switch Recombination by PGK-neor Cassettes Inserted into the Immunoglobulin Heavy Chain Constant Region Locus," Proceedings of the National Academy of Sciences of the U.S.A., Mar. 1999, vol. 96 (6), pp. 3000-3005.

Sekiguchi J., et al., "The Mechanism of V(D)J Recombination," Molecular Biology of B Cells, Chapter 5, 2004, pp. 61-82.

Sen R., et al., "Multiple Nuclear Factors Interact with the Immunoglobulin Enhancer Sequences," Cell, 1986, vol. 46 (5), pp. 705-716.

Seong E., et al., "To Knockout in 129 or in C57BL/6: That is the Question," Trends in Genetics, 2004, vol. 20 (2), pp. 59-62.

Sequence Listing to WO2008054606A2, 163 pages.

Serwe M., et al., "V(D)J Recombination in B Cells is Impaired but not Blocked by Targeted Deletion of the Immunoglobulin Heavy Chain Intron Enhancer," The EMBO Journal, 1993, vol. 12 (6), pp. 2321-2327.

Sharan S.K., et al., "Recombineering: a homologous recombination-based method of genetic engineering," Nature Protocols, 2009, vol. 4(2), pp. 206-223.

Sharon J., et al., "Expression of a VHC Kappa Chimaeric Protein in Mouse Myeloma Cells," Nature, 1984, vol. 309 (5966), pp. 364-367.

Shaul Y., et al., "Homologous Recombination Between a Defective Virus and a Chromosomal Sequence in Mammalian Cells," Proceedings of the National Academy of Sciences of the U.S.A., 1985, vol. 82 (11), pp. 3781-3784.

Shaw, D.J., Ja Kemp, European Patent Attorney, Response to Summons to attend Oral Proceedings in re Opposition against EP2757875 in the name of Kymab Limited pertaining to Application No. 12762378.8, dated Apr. 16, 2020, 21 pages.

Sheng Y., et al., "Transformation of Escherichia coli with large DNA molecules by electroporation," Nucleic Acids Research, 1995, vol. 23, Issue No. 11, pp. 1990-1996.

Shi B., et al., "Comparative Analysis of Human and Mouse Immunoglobulin Variable Heavy Regions from IMGT/LIGM-DB with IMGT/HighV-QUEST," Theoretical Biology and Medical Modelling, 2014, vol. 11, No. 30, pp. 1-11.

Shi Y.P., et al., "The Mapping of Transgenes by Fluorescence in Situ Hybridization on G-Banded Mouse Chromosomes," Mammalian Genome, 1994, vol. 5 (6), pp. 337-341.

Shih H.H., "Discovery Process for Antibody-Based Therapeutics," Development of Antibody-Based Therapeutics, Chapter 2, 2012, pp. 9-32.

Shimizu A., et al., "Immunoglobulin Double-Isotype Expression by Trans-mRNA in a Human Immunoglobulin Transgenic Mouse," Proceedings of the National Academy of Sciences of the U.S.A., 1989, vol. 86 (20), pp. 8020-8023.

Shiokawa S., et al., "IgM Heavy Chain Complementarity-Determining Region 3 Diversity Is Constrained by Genetic and Somatic Mechanisms Until Two Months After Birth," Journal of Immunology, May 1999, vol. 162, Issue No. 10, pp. 6060-6070.

Shore D.E., Attorney for Applicant, Third-Party Pre-Issuance Submission Under 37 CFR Sec. 1.290 in U.S. Appl. No. 15/088,805, filed Nov. 17, 2017, 44 pages.

Shore D.E., Attorney for Applicant, Third-Party Pre-Issuance Submission Under 37 CFR Sec. 1.290 in U.S. Appl. No. 15/199,575, filed May 31, 2017, 37 pages.

Shore D.E., Attorney for Applicant, Third-Party Pre-Issuance Submission Under 37 CFR Sec. 1.290 in U.S. Appl. No. 15/656,897, filed May 4, 2018, 55 pages.

Shore D.E., Attorney for Applicant, Third-Party Pre-Issuance Submission Under 37 CFR Sec. 1.290 in U.S. Appl. No. 15/690,183, filed Feb. 28, 2018, 60 pages.

Shore D.E., Attorney for Applicant, Third-Party Pre-Issuance Submission Under 37 CFR Sec. 1.290 in U.S. Appl. No. 15/786,281, filed Jun. 27, 2018 (Second Submission), 62 pages.

Shore D.E., Attorney for Applicant, Third-Party Pre-Issuance Submission Under 37 CFR Sec. 1.290 in U.S. Appl. No. 15/786,281, filed Jun. 27, 2018 (Third Submission), 53 pages.

Shore D.E., Attorney for Applicant, Third-Party Pre-Issuance Submission Under 37 CFR Sec. 1.290 in U.S. Appl. No. 15/786,281, filed Jun. 27, 2018, 63 pages.

Shore D.E., Attorney for Applicant, Third-Party Pre-Issuance Submission Under 37 CFR Sec. 1.290 in U.S. Appl. No. 15/948,709, filed Jan. 10, 2019, 43 pages.

Shore D.E., Attorney for Applicant, Third-Party Pre-Issuance Submission Under 37 CFR Sec. 1.290 in U.S. Appl. No. 15/955,216, dated Feb. 5, 2019, 52 pages.

Shore D.E., Attorney for Applicant, Third-Party Pre-Issuance Submission Under 37 CFR Sec. 1.290 in U.S. Appl. No. 16/216,666, filed Dec. 11, 2019, 42 pages.

Mills F.C., et al., "Enhancer Complexes Located Downstream of Both Human Immunoglobulin C$\alpha$ Genes," The Journal of Experimental Medicine, Sep. 1997, vol. 186 (6), pp. 845-858.

Milner E.C., et al., "Polymorphism and Utilization of Human VH Genesa," Annals of the New York Academy of Sciences, 1995, vol. 764, pp. 50-61.

Minaee S., et al., "Mapping and Functional Analysis of Regulatory Sequences in the Mouse ?5-VpreB1 Domain," Molecular Immunology, 2005, vol. 42 (11), pp. 1283-1292.

Mir K.U., "Sequencing Genomes: From Individuals to Populations," Briefings in Functional Genomics & Proteomics, 2009, vol. 8 (5), pp. 367-378.

Missirlis P.I., et al., "A high-throughout screen identifying sequence and promiscuity characteristics of the loxP spacer region in Cre-mediated recombination," BMC Genomics, Apr. 2006, vol. 7(73), 13 pages.

Mitra R., et al., "PiggyBac can bypass DNA synthesis during cut and paste transposition," The EMBO Journal, 2008, vol. 27, pp. 1097-1109.

Moffatt S., et al., "PEGylated J591 mAb loaded in PLGA-PEG-PLGA tri-block copolymer for targeted delivery: In vitro evaluation in human prostate cancer cells," International Journal of Pharmaceutics, 2006, vol. 317, pp. 10-13.

Monaco A.P., et al., "YACs, BACs, PACs and MACs: Artificial Chromosomes as Research Tools," Trends in Biotechnology, Jul. 1994, vol. 12 (7), pp. 280-286.

Moran N., "Mouse Platforms Jostle for Slice of Humanized Antibody Market," Nature Biotechnology, Apr. 2013, vol. 31 (4), pp. 267-268.

Moreau P., et al., "The SV40 72 Base Repair Repeat has a Striking Effect on Gene Expression Both in SV40 and Other Chimeric Recombinants," Nucleic Acids Research, 1981, vol. 9 (22), pp. 6047-6068.

Moreno R.D., et al., "The Emerging Role of Matrix Metalloproteases of the ADAM Family in Male Germ Cell Apoptosis," Spermatogenesis, 2011, vol. 1 (3), pp. 195-208.

Morrison S.L., et al. "Vectors and Approaches for the Eukaryotic Expression of Antibodies and Antibody Fusion Proteins" Antibody Engineering, 2nd Edition, Chapter 9, 1995, 31 pages.

Mortuza F.Y., et al., "Immunoglobulin Heavy-Chain Gene Rearrangement in Adult Acute Lymphoblastic Leukemia Reveals Preferential Usage of JH-Proximal Variable Gene Segments," Blood, May 2001, vol. 97 (9), pp. 2716-2726.

Mullins L.J., et al., "Transgenesis in the Rat and Larger Mammals," Perspective Series: Molecular Medicine in Genetically Engineered Animals, Journal of Clinical Investigation, Apr. 1996, vol. 97 (7), pp. 1557-1560.

Muramatsu M., et al., "Specific Expression of Activation-induced Cytidine Deaminase (AID), a Novel Member of the RNA-editing

(56) References Cited

OTHER PUBLICATIONS

Deaminase Family in Germinal Center B Cells," 1999, The Journal of Biological Chemistry, vol. 274 (26), pp. 18470-18476.

Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," cited in an IDS in U.S. Appl. No. 14/192,051 of MacDonald et al., dated Oct. 6, 2014, 62 pages.

Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," including course timetables, 72 pages.

Murphy A., "VelocImmune: Immunoglobulin Variable Region Humanized Mice," Recombinant Antibodies for Immunotherapy, 1st Edition, Chapter 8, 2009, pp. 100-108.

Murphy A.J., et al., "Mice with megabase humanization of their Immunoglobulin Genes Generate Antibodies as Efficiently as Normal Mice," Proceedings of the National Academy of Sciences of the U.S.A., 2014, vol. 111 (14), pp. 5153-5158.

Murphy D., "BAC-based Modifications of the Mouse Genome: The Big and the Backward," The Advanced Course: Genetic Manipulation of ES Cells, dated Nov. 3, 2009, VP Target Discovery, Regeneron Pharmaceuticals, 58 pages.

Murphy K., et al., The Generation of Lymphocyte Antigen Receptors, excerpt from Janeway's Immunobiology, Seventh edition, Chapter 4, 2008, p. 158.

Muyrers J.P.P., et al., "Rapid Modification of Bacterial Artificial Chromosomes by ET-Recombination," Nucleic Acids Research, 1999, vol. 27 (6), pp. 1555-1557.

Muyrers J.P.P., et al., "Techniques: Recombinogenic engineering—new options for cloning and manipulating DNA," Trends in Biochemical Sciences, May 2001, vol. 26(5), pp. 325-331.

Muñoz M., et al., "Constraints to Progress in Embryonic Stem Cells from Domestic Species," Stem Cell Review and Reports, 2009, vol. 5, pp. 6-9.

Muñoz-López M., et al., "DNA Transposons: Nature and Applications in Genomics," Current Genomics, 2010, vol. 11, pp. 115-128.

Mårtensson I.L., et al., "Role of the Surrogate Light Chain and the Pre-B-Cell Receptor in Mouse B-Cell Development," Immunology, 2000, vol. 101 (4), pp. 435-441.

Mårtensson I.L., et al., "The pre-B-cell receptor," Current Opinion in Immunology, 2007, vol. 19, pp. 137-142.

Müller U., "Ten Years of Gene Targeting: Targeted Mouse Mutants, from Vector Design to Phenotype Analysis," Mechanisms of Development, 1999, vol. 82 (1-2), pp. 3-21.

Nadel B., et al., "Sequence of the Spacer in the Recombination Signal Sequence Affects V(D)J Rearrangement Frequency and Correlates with Nonrandom Vκ Usage in Vivo," The Journal of Experimental Medicine, 1998, vol. 187 (9), pp. 1495-1503.

Nagle M., "Regeneron Helps Make Sanofi Velocimmune to its 'Weak' Pipeline," Dec. 2007, 2 pages [outsourcing-pharmac.com].

Nandi A.K., et al., "Regulated Expression of Genes Inserted at the Human Chromosomal β-globin Locus by Homologous Recombination," Proceedings of the National Academy of Sciences of the U.S.A., 1988, vol. 85 (11), pp. 3845-3849.

Narayanan K., et al., "Bacterial Artificial Chromosome Mutagenesis Using Recombineering, Article ID: 971296," Journal of Biomedicine and Biotechnology, 2010, vol. 2011, Article ID No. 971296, 10 pages.

Narayanan K., et al., "Efficient and Precise Engineering of a 200 kb _-Globin Human/Bacterial Artificial Chromosome in E. coli DH10B using an Inducible Homologous Recombination System," Gene Therapy, 1999, vol. 6 (3), pp. 442-447.

Nelson A.L., et al., "Development Trends for Human Monoclonal Antibody Therapeutics," Nature Reviews Drug Discovery, 2010, vol. 9 (10), pp. 767-774.

Neuberger M.S., "Expression and regulation of immunoglobulin heavy chain gene transfected into lymphoid cells," The EMBO Journal, 1983, vol. 2 (8), pp. 1373-1378.

Neuberger M.S., et al., "Isotype Exclusion and Transgene Down-Regulation in Immunoglobulin-λ Transgenic Mice," Nature, Mar. 1989, vol. 338 (6213), pp. 350-352.

Neuberger M.S., et al., "Somatic Hypermutation," Current Opinion in Immunology, 1995, vol. 7 (2), pp. 248-254.

New Zealand Patent Office, Simon Maguire, Authorized Officer, Further Examination Report for Patent No. 623756, mailed on Sep. 9, 2015, 3 pages.

Newcombe C., et al., "Antibody Production: Polyclonal-Derived Biotherapeutics," Journal of Chromatography B, 2007 vol. 848, pp. 2-7.

Ni J.M., et al., "Transposon tools hopping in vertebrates," Briefings in Functional Genomics and Proteomics, 2008, vol. 7, Issue No. 6, pp. 444-453.

Nicholls, James, Ja Kemp, Reply to Patentee's Grounds of Appeal, Opposition roceedings in relation to EP Patent No. 3,028,564 B1 (Appln. No. EP1615124.0), dated Nov. 24, 2021, 12 pages.

Nicholls, James, Ja Kemp, Statement of Facts and Arguments in Support of Opposition, Opposition proceedings in relation to EP Patent No. 3,622,813 B1 (Appln. No. EP19207050.6), dated Nov. 17, 2021, 56 pages.

Nicholls, James, Ja Kemp, Third-Party Observations according to Article 115 EPC regarding European Patent Application No. 21169076. 3, dated May 27, 2022, 12 pages.

Nicholson I.C., et al., "Antibody Repertoires of Four- and Five-Feature Translocus Mice Carrying Human Immunoglobulin Heavy Chain and K and λ Light Chain Yeast Artificial Chromosomes," Journal of Immunology, 1999, vol. 163 (12), pp. 6898-6906.

Niemann H., et al., "Transgenic Farm Animals: Present and Future," Revue scientifique et technique (International Office of Epizootics), 2005, vol. 24 (1), pp. 285-298.

Nitschke, L., et al., "Deletion of the DQ52 Element Within the Ig Heavy Chain Locus Leads to a Selective Reduction in VDJ Recombination and Altered D Gene Usage," The Journal of Immunology, 2001, vol. 166(4), pp. 2540-2552.

Nucleotide Sequence RID Y55HBK1W114, accessed Aug. 6, 2014, 2 pages.

O'Dea, T.P., Attorney for Applicant, Third-Party Pre-Issuance Submission Under 37 CFR Sec. 1.290 in U.S. Appl. No. 15/383,342, filed Aug. 7, 2017, 32 pages.

O'Dea, T.P., Attorney for Applicant, Third-Party Pre-Issuance Submission Under 37 CFR Sec. 1.290 in U.S. Appl. No. 15/385,348, filed Jul. 28, 2017, 48 pages.

O'Dea, T.P., Attorney for Applicant, Third-Party Pre-Issuance Submission Under 37 CFR Sec. 1.290 in U.S. Appl. No. 15/385,372, filed Jul. 28, 2017, 48 pages.

Australian IP Office, Melissa Adams, Examiner, Examination Report No. 2 for Standard Patent Application No. 2021200079, dated Jun. 29, 2023, 4 pages.

Blair, K., et al., "Culture parameters for stable expansion, genetic modification and germline transmission of rat pluripotent stem cells," Biology Open, vol. 1, No. 1, Jan. 15, 2012, pp. 58-65.

European Patent Office, Extended European Search Report for Application No. 23201805.1, dated Feb. 15, 2024, 19 pages.

European Patent Office, Extended European Search Report for Application No. 23161385.2, dated May 26, 2023, 11 pages.

Eyer, L., et al., "Single-domain antibody fragments derived from heavy-chain antibodies: a review," Veterinarni Medicina, 57, 2012 (9), pp. 439-513.

Gregory, L., CMS Cameron McKenna Nabarro Olswang LLP, Response to Search Opinion dated Jan. 16, 2023 to the European Patent Office with corresponding claims for Application No. 22173215. 9, dated Jun. 28, 2023, 26 pages.

Hoffmann, R., et al., "Changes in Gene Expression Profiles in Developing B Cells of Murine Bone Marrow," Genome Res 2002, vol. 12, pp. 98-111.

Hollywood J., Cameron McKenna Nabarro Olswang LLP, Response to Opposition for European Patent No. 3311661 as filed with the European Patent Office on Jun. 9, 2023, 21 pages.

(56)　　　　　References Cited

OTHER PUBLICATIONS

Japanese Patent Office, Notice of Reasons for Refusal—Application No. 2022-177513, mailed Oct. 23, 2023, together with English translation, 5 pages.

Merriam Webster Dictionary, Definition of "a" 2023, 21 pages [retrieved online: https://www.merriam-webster.com/dictionary/a].

Prak, E., et al., "Light chain editing in kappa-deficient animals: a potential mechanism of B cell tolerance," J Exp Med. Nov. 1, 1994;180(5):1805-15.

Vale, A., et al., "Clinical Consequences of Defects in B cell Development," The Journal of Allergy and Clinical Immunology, 2010, vol. 125, Issue 4, pp. 778-787.

Stevens S., et al., Poster (Exhibit IJR-46): "VelocImmuneTM: Humanization of immunoglobulin loci using VelociGene® technology," and evidence of unavailability, Sep. 2006, 42 pages.

Storb U., et al., "Physical Linkage of Mouse A Genes by Pulsed-Field Gel Electrophoresis Suggests that the Rearrangement Process Favors Proximate Target Sequences," Molecular and Cellular Biology, Feb. 1989, vol. 9 (2). pp. 711-718.

Sullivan P.M., et al., "Targeted Replacement of the Mouse Apolipoprotein E Gene With the Common Human APOE3 Allele Enhances Diet-Induced Hypercholesterolemia and Atherosclerosis," The Journal of Biological Chemistry, 1997, vol. 272, No. 2, pp. 17972-17980.

Sun Y., et al., "Repertoire of Human Antibodies against the Polysaccharide Capsule of Streptococcus pneumoniae Serotype 6B," Infection and Immunity, Mar. 1999, vol. 67 (3), pp. 1172-1179.

Suárez E., et al., "Human monoclonal antibodies produced in transgenic BABκ,λ mice recognising idiotypic immunoglobulins of human lymphoma cells," Molecular Immunology, 2004, vol. 41, pp. 519-526.

Suárez E., et al., "Rearrangement of Only One Human IGHV Gene is Sufficient to Generate a Wide Repertoire of Antigen Specific Antibody Responses in Transgenic Mice," Molecular Immunology, 2006, vol. 43 (11), pp. 1827-1835.

Table S1 (from Breden F., et al., "Comparison of Antibody Repertoires Produced by HIV-1 Infection, Other Chronic and Acute Infections, and Systemic Autoimmune Disease," PLoS One, 2011, vol. 6 (3), pp. e16857-1-e16857-11.), 60 pages.

Table S2 (from Breden F., et al., "Comparison of Antibody Repertoires Produced by HIV-1 Infection, Other Chronic and Acute Infections, and Systemic Autoimmune Disease," PLoS One, 2011, vol. 6 (3), pp. e16857-1-e16857-11.), 14 pages.

Taiwanese Patent Office, Search Report , Taiwanese Patent Application No. 107123525, dated Nov. 14, 2022, 1 page.

Takeda S., et al., "Construction of Chimaeric Processed Immunoglobulin Genes Containing Mouse Variable and Human Constant Region Sequences," Nature, Apr. 1985, vol. 314 (6010), pp. 452-454.

Taki S., et al., "Targeted Insertion of a Variable Region Gene into the Immunoglobulin Heavy Chain Locus," Science, 1993, vol. 262 (5137), pp. 1268-1271.

Talbot P., et al., "Cell Adhesion and Fertilization: Steps in Oocyte Transport, Sperm-Zona Pellucida Interactions, and Sperm-Egg Fusion," Biology of Reproduction, 2003, vol. 68 (1), pp. 1-9.

Tan L.K., et al., "A Human-Mouse Chimeric Immunoglobulin Gene with a Human Variable Region is Expressed in Mouse Myeloma Cells," Journal of Immunology, Nov. 1985, vol. 135 (5), pp. 3564-3567.

Tanaka, M., et al., "Somatic chromosomal translocation between Ewsr1 and Fli1 loci leads to dilated cardiomyopathy in a mouse model," Scientific Reports, 2015, vol. 5: 7826, 9 pages.

Tanimoto Y., et al., "Embryonic Stem Cells Derived from C57BL/6J and C57BL/6N Mice," Comparative Medicine, Aug. 2008, vol. 58 (4), pp. 347-352.

Taylor L.D., et al., "A transgenic mouse that expresses a diversity of human sequence heavy and light chain Immunoglobulins," Nucleic Acids Research, 1992, vol. 20 (23), pp. 6287-6295.

Taylor L.D., et al., "Human Immunoglobulin Transgenes Undergo Rearrangement, Somatic Mutation and Class Switching in Mice that Lack Endogenous IgM," International Immunology, 1994, vol. 6 (4), pp. 579-591.

Te Riele H., et al., "Highly Efficient Gene Targeting in Embryonic Stem Cells through Homologous Recombination with Isogenic DNA Constructs," Proceedings of the National Academy of Sciences of the U.S.A., 1992, vol. 89 (11), pp. 5128-5132.

The Jackson Laboratory, "Breeding Strategies for Maintaining Colonies of Laboratory Mice," A Jackson Laboratory Resource Manual, 2007, pp. 1-29.

Thomas K.R., et al., "High Frequency Targeting of Genes to Specific Sites in the Mammalian Genome," Cell, 1986, vol. 44 (3), pp. 419-428.

Thomas K.R., et al., "Introduction of Homologous DNA Sequences into Mammalian Cells Induces Mutations in the Cognate Gene," Nature, 1986, vol. 324 (6092), pp. 34-38.

Thomas K.R., et al., "Site-Directed Mutagenesis by Gene Targeting in Mouse Embryo-Derived Stem Cells," Cell, 1987, vol. 51 (3), pp. 503-512.

Throsby M., et al., "Heterosubtypic Neutralizing Monoclonal Antibodies Cross-Protective against H5N1 and H1N1 Recovered from Human IgM+ Memory B Cells," PLoS One, Dec. 2008, vol. 3, Issue No. 12, pp. e3942-1-e3942-15.

Thykjaer T., et al., "Gene Targeting Approaches Using Positive-Negative Selection and Large Flanking Regions," Plant Molecular Biology, 1997, vol. 35 (4), pp. 523-530.

Tomizuka K., et al., "Double Trans-Chromosomic Mice: Maintenance of Two Individual Human Chromosome Fragments Containing Ig Heavy and κ Loci and Expression of Fully Human Antibodies," Proceedings of the National Academy of Sciences of the U.S.A., Jan. 2000, vol. 97 (2), pp. 722-727.

Tonegawa S., "Somatic Generation of Antibody Diversity," Nature, Apr. 1983, vol. 302 (5909), pp. 575-581.

Tong C., et al., "Production of p53 gene knockout rats by homologous recombination in embryonic stem cells," Nature, Sep. 2010, vol. 467 (7312), pp. 211-213.

Torres R., et al., "Flox and Modify", Laboratory Protocols for Conditional Gene Targeting, Institute for Genetics, University of Cologne, 1997, pp. 37-41.

Traggiai, E. et al., "An efficient method to make human monoclonal antibodies from memory B cells: potent neutralization of SARS coronavirus", Nature Medicine, Aug. 2004, vol. 10(8), pp. 871-875.

Tuaillon N., et al., "Human immunoglobulin heavy-chain minilocus recombination in transgenic mice: Gene-segment use in μand λ transcripts," Proceedings of the National Academy of Sciences of the U.S.A., Apr. 1993, vol. 90, pp. 3720-3724.

Tucker P.W., et al., "Mouse IgA Heavy Chain Gene Sequence: Implications for Evolution of Immunoglobulin Hinge Axons," Proceedings of the National Academy of Sciences of the U.S.A., Dec. 1981, vol. 78 (12), pp. 7684-7688.

Tung J.W., "Phenotypically distinct B cell development pathways map to the three B cell lineages in the mouse," Proceedings of the National Academy of Sciences of the U.S.A., Apr. 2006, vol. 103(16), pp. 6293-6298.

U.S. Patent and Trademark Office, Before the Patent and Appeal Board, AIA Review No. IPR2019-01577, Decision (Denying Institution of Inter Parties Review 35 U.S.C. Sec. 314), dated Apr. 1, 2020, 20 pages.

U.S. Patent and Trademark Office, Before the Patent and Appeal Board, AIA Review No. IPR2019-01578, Decision (Denying Institution of Inter Parties Review 35 U.S.C. Sec. 314), dated Apr. 1, 2020, 17 pages.

U.S. Patent and Trademark Office, Before the Patent and Appeal Board, AIA Review No. IPR2019-01579, Decision (Denying Institution of Inter Parties Review 35 U.S.C. Sec. 314), dated Mar. 20, 2020, 20 pages.

U.S. Patent and Trademark Office, Before the Patent and Appeal Board, AIA Review No. IPR2019-01580, Decision (Denying Institution of Inter Parties Review 35 U.S.C. Sec. 314), dated Mar. 18, 2020, 26 pages.

(56) References Cited

OTHER PUBLICATIONS

U.S. Patent and Trademark Office, Before the Patent and Appeal Board, AIA Review No. IPR2020-00389, Decision (Denying Institution of Inter Parties Review 35 U.S.C. Sec. 314), dated May 26, 2020, 21 pages.

U.S. Patent and Trademark Office, Office Action for U.S. Appl. No. 13/310,431, dated Sep. 7, 2021, 109 pages.

Ungrin M.D., et al., "Strict Control of Telomerase Activation Using Cre-Mediated Inversion," BMC Biotechnology, 2006, vol. 6, pp. 1-9, 2006.

United Kingdom Intellectual Property Office, Combined Search and Examination Report under Sections 17 and 18(3) for Application No. GB1317410.7, dated Nov. 21, 2013, 8 pages.

United Kingdom Intellectual Property Office, Combined Search and Examination Report under Sections 17 and 18(3) for Application No. GB1317447.9, dated Jan. 14, 2014, 7 pages.

United Kingdom Intellectual Property Office, Corrected Search Report Under Section 17 for Application No. GB1122047.2, mailed on Apr. 20, 2012, 5 pages.

United Kingdom Intellectual Property Office, Search Report under Section 17 for Application No. GB1116122.1, dated Feb. 2, 2012, 1 page.

University of California Santa Cruz, "Human Genome Browser GRCh37/hg19 Assembly," Feb. 2009, 3 pages.

Urquhart-Dykes & Lord LLP, Third-Party Observation for Application No. EP20140772198, dated Dec. 14, 2015, 8 pages.

USPTO, Excerpts from U.S. Appl. No. 14/682,859, filed Apr. 9, 2015, including Applicant-initiated Interview Summary; Amendments to the Claims and Information Disclosure Statement, 14 pages.

Valancius V., et al., "Testing an "In-Out" Targeting Procedure for Making Subtle Genomic Modifications in Mouse Embryonic Stem Cells," Molecular and Cellular Biology, Mar. 1991, vol. 11(3), pp. 1402-1408.

Valenzuela D.M., et al., "High-Throughput Engineering of the Mouse Genome Coupled with High-Resolution Expression Analysis," Nature Biotechnology, 2003, vol. 21 (6), pp. 652-659 and vol. 21 (7), p. 822.

Van Der Weyden L., et al., "Mouse Chromosome Engineering for Modeling Human Disease," Ann. Rev. Genomics Hum. Genet., 2006, vol. 7, pp. 247-276.

Van Dijk M., Declaration of Marcus Van Dijk with exhibits, Apr. 30, 2016, 139 pages.

European Patent Office, Communication purusant to Article 94(3) EPC regarding 24178098.0, dated Mar. 11, 2026, 8 pages.

Inlay Matthew A et al.: "Roles of the Ig Light Chain Intronic and 3 Enhancers in Igk Somatic Hypermutation1", Jul. 15, 2006 (Jul. 15, 2006), pp. 1-7.

Xiang Yogui et al: "The Downstream Transctiptional Enhancer, Ed, Postively Regulates Mouse Ig[kappa] Gene Expression and Somatic Hypermutation", The Journal of immunology (1950), vol. 180, No. 10, May 15, 2008 (May 15, 2008), pp. 6725-6732.

* cited by examiner

Fig. 1

Pecentage CD19$^+$ / B220$^+$ B-cell Population Present in Spleen Following Immunisation With An Undisclosed Antigen

SEQUENCE LISTING

<160> NUMBER OF SEQ ID NOS: 1

<210> SEQ ID NO 1
<211> LENGTH: 107
<212> TYPE: PRT
<213> ORGANISM: Homo sapiens

<400> SEQUENCE: 1

-continued

```
Tyr Val Leu Thr Gln Pro Pro Ser Val Ser Val Ala Pro Gly Glu Thr
1               5                   10                  15

Ala Arg Ile Thr Cys Gly Gly Asp Asn Ile Gly Arg Lys Ser Val Tyr
                20                  25                  30

Trp Tyr Gln Gln Lys Ser Gly Gln Ala Pro Val Leu Val Ile Tyr Tyr
        35                  40                  45

Asp Ser Asp Arg Pro Ser Gly Ile Pro Glu Arg Phe Ser Gly Ser Asn
        50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Gly Ser Ser Asp His Trp
                85                  90                  95

Val Phe Gly Gly Gly Thr Lys Leu Thr Val Leu
                100                 105
```

CELLS, VERTEBRATES, POPULATIONS AND METHODS

PRIORITY

This application is a continuation-in-part of PCT/EP2018/068309 filed Jul. 5, 2018, and claims the benefit of GB 1710984.4 filed Jul. 7, 2017. The contents of each application being incorporated by reference herein in their entirety.

FIELD OF THE INVENTION

The invention relates to cells and non-human vertebrates for producing antibody chains, in particular for use in producing multi-specific antibodies useful for therapy or diagnosis.

BACKGROUND

Antibodies are a rapidly growing drug class. A typical 4-chain antibody contains two identical heavy chains and two identical light chains, which form a molecule with bivalent and monospecific antigen binding features. The bispecific antibody is a new class of drug which can bind two different antigens or two different epitopes of the same antigen at the same time. There are several applications of bispecific antibodies for disease treatment. The most widely used application of this concept is in cancer immunotherapy, where bispecific antibodies engage cytotoxic T cells and target to tumour cells to be destroyed. They can also be applied to simultaneously block to two targets (Klein, C et al. MABs. 2016. 8: 1010-20), or act as a cofactor for an enzymatic pathway (Kitazawa, T. et al. Nat Med. 2012. 18: 1570-4). Two bispecific antibodies, catumaxomab (anti-EpCAM×anti-CD3) and blinatumomab (anti-19×anti-CD3) have been approved for therapy, and several additional bispecific antibodies are currently in clinical development. There are five different structural groups for bispecific antibodies: (i) bispecific IgG (BsIgG) (ii) IgG appended with an additional antigen-binding moiety (iii) BsAb fragments (iv) bispecific fusion proteins and (v) BsAb conjugates (Spiess, C. et al Mol. Immunol. 2015. 67:95-106). Among them, BsIgG is a bispecific antibody with molecular weight close to a IgG molecule. It usually has similar biological and biophysical features to a typical IgG. Production of BsIgG by co-expression of the two antibodies in cells is a highly challenge because of the low yield of desired BsIgG and the difficulty to remove closely related mispaired IgG molecules. Two heavy chains can from homodimers as well as desired heterodimers. In addition, light chains can mispair with non-cognate heavy chains. Consequently, coexpression of two antibodies results in nine unwanted IgG species and only one desired BsIgG due to the heavy chain pairing and light chain pairing problems.

Engineering heavy chains to favour the heterodimerization has been demonstrated by the "knob-into-hole" technology (idgway, J. B. et al. Protein Eng. 1996. 9: 617-21; Atwell, S. et al. J. Mol. Biol. 1997. 270: 26-35) or the "charge pairing" technology (Gunasekaran, K. et al. J. Biol. Chem. 2010. 285: 19637-46; Strop, P. et al. J. Mol. Biol. 2012. 420: 204-19). These technologies aim to resolve the heavy chain pairing problem. The light chain pairing problem is obviated by expression of antibodies using common light chains (Merchant, M. et al. Nat. Biotechnol. 1998. 16: 677-81). By applying the "knob-into-hole" or "charge pairing", and common light chain technologies, coexpression of one light chain and two heavy chains results in one dominant BsIgG and three minor mispairing species. The knobs-into-holes technology is described in U.S. Pat. No. 5,731,168 and WO098/50431. Purification steps using cation exchange (Sampei, Z. et al. PLoS One. 2013. 8: e57479) or differential protein A binding (Smith, E. J. et al. Sci. Rep. 2015. 5: 17943) have been applied to isolate this dominant expressed BsIgG.

It is challenging to identify a common light chain for BsIgG. Forced pairing of non-cognate heavy and light chains usually results in low yield of expression or instability of molecules. Light chain shuffling between two cognate paired light chains has been used to identify the common light chain (Sampei, Z. et al. PLoS One. 2013. 8: e57479). This, however, relies on tedious steps and a lot of effort, and the outcome is also uncertain. Compared to this method, the "common light chain transgenic" technology is promised to be more straightforward and simple, relying on in vivo selection to generate the natural pairing molecules. In these applications, mice engineered to contain only one chimeric light chain-encoding sequence (human variable and mouse constant regions) are used to identify antibodies sharing the similar but not necessarily identical light chain because the inserted rearranged light chain sequence is still susceptible to somatic hypermutation (SHM). The inserted light chain choice is also limited as it relies on germline transmitted mice with one light chain sequence insertion. WO2004/106375, WO2009/1577771, EP2147594 and WO2014/160179 discuss techniques relevant to production of bispecific antibodies and common light chain mice.

STATEMENT OF INVENTION

The inventors realised that the provision of a V domain coding variable region sequence 3' of the intronic enhancer in an antibody chain locus minimises SHM of the V region, which allows the invention to be used to identify and use true common light chains, VL domains and VH domains that can pair with these to produce antigen binding sites.

Thus, in a first configuration, the invention provides:—A cell comprising an antibody light chain locus (first locus), wherein the locus comprises (in 5' to 3' direction)
- (a) a light chain intronic enhancer;
- (b) a rearranged antibody variable region encoding a rearranged antibody V domain; and
- (c) an antibody light chain constant region encoding a light chain C domain;
- wherein the locus is operable to express an antibody chain comprising (in N- to C-terminal direction) said rearranged V domain and said C domain.

In a second configuration, the invention provides:—A cell comprising an antibody heavy chain locus (first locus), wherein the locus comprises (in 5' to 3' direction)
- (a) a heavy chain intronic enhancer (Eμ);
- (b) a rearranged antibody variable region encoding a rearranged antibody V domain;
- (c) an optional switch sequence; and
- (d) an antibody heavy chain constant region encoding a heavy chain CHI domain;
- wherein the locus is operable to express an antibody chain comprising (in N- to C-terminal direction) said rearranged V domain and said CHI domain.

In a third configuration, the invention provides:—A transgenic non-human vertebrate comprising a plurality of cells according to the invention.

In a fourth configuration, the invention provides:—A transgenic non-human vertebrate whose antibody light chain repertoire is at least 95% pure for a single rearranged VL domain species.

In a fifth configuration, the invention provides:—A transgenic non-human vertebrate whose antibody light chain repertoire comprises VL domains derived from the recombination of a first VL gene segment and a first JL gene segment, wherein at least 95% of all VL domains derived from said recombination comprise the same VL amino acid sequence.

In a sixth configuration, the invention provides:—A plurality of spleen, bone marrow, B-cells or blood cells of a vertebrate according to the invention comprising a plurality of said first loci.

In a seventh configuration, the invention provides:—A population of spleen, bone marrow, B-cells, hybridomas, CHO cells, HEK cells, MEF cells, COS cells, HeLa cells or blood cells, wherein each cell is according to the invention; and wherein (a) at least 95% of the antibodies share the same light chain VL domain and the population comprises at least 10 different VH domain species; or (b) the antibodies comprise VL domains derived from the recombination of a first VL gene segment and a first JL gene segment, wherein at least 95% of all said VL domains derived from said recombination comprise the same VL amino acid sequence and the population comprises at least 10 different VH domain species.

In a eighth configuration, the invention provides:—A polyclonal antibody population, wherein at least 95% of the antibodies comprised by the population share the same light chain VL domain and the population comprises at least 10 different VH domain species.

In a ninth configuration, the invention provides:—A polyclonal antibody population, comprising VL domains derived from the recombination of a first VL gene segment and a first JL gene segment, wherein at least 95% of all said VL domains derived from said recombination comprise the same VL amino acid sequence and the population comprises at least 10 different VH domain species.

In a tenth configuration, the invention provides:—A method of identifying or obtaining an antibody, an antibody variable domain, a nucleotide sequence encoding an antibody or an antibody variable domain, or an expression vector or host cell that is capable of expressing the antibody or domain, wherein the antibody or domain is capable of specifically binding to a target antigen, the method comprising (a) contacting the cell population of the invention, or the antibody population of the invention with said antigen (eg, immobilised on a solid support);

(b) binding antibodies expressed or comprised by said population to said antigen; and (c) isolating or identifying one or more antibodies that bind to the antigen, or isolating or identifying a VH and/or a VL domain of a said one or more antibody; or identifying a nucleotide sequence encoding a said VH or VL; and (d) optionally (i) correlating a said identified antibody or domain with a nucleotide sequence encoding therefor, thereby identifying said sequence;

(ii) amplifying said sequence (eg, using PCR) and inserting the sequence into an expression vector or a host cell genome for expression of the encoded antibody or domain; and

(iii) optionally expressing and isolating said antibody or domain (eg, wherein the domain is comprised by an antibody chain), wherein steps (i) and (ii) can be carried out in any order.

In a eleventh configuration, the invention provides:—A plurality of B-cells, hybridomas, CHO cells, HEK cells, MEF cells, COS cells, HeLa cells that expresses the polyclonal antibody population of the invention.

In a twelfth configuration, the invention provides:—A method obtaining a nucleotide sequence encoding an antibody or an antibody variable domain, wherein the antibody or domain is capable of specifically binding to a target antigen, the method comprising (a) obtaining VL and/or VH-encoding nucleotide sequences from the cells of the invention;

(b) amplifying said sequence (eg, using PC); and (c) optionally inserting the sequence into an expression vector or a host cell genome for expression of the encoded antibody or domain.

In a thirteenth configuration, the invention provides:—A method obtaining an antibody-producing cell line for the production of antibodies that specifically bind to an antigen, the method comprising inserting VH and VL-encoding nucleotide sequences into the genome of a host cell (eg, a CHO, HEK, MEF, COS or HeLa cell), wherein (a) each VH sequence is operably inserted 5' of an antibody heavy chain constant region (eg, a human constant region) for expression of heavy chains by the cell comprising VH and C domains;

(b) each VL sequence is operably inserted 5' of an antibody light chain constant region (eg, a human constant region) for expression of light chains by the cell comprising VL and C domains;

(c) wherein the expressed heavy chains are capable of pairing with the light chains to produce heavy-light chain pairs, each pair comprising a VH/VL binding site that is capable of binding to an antigen; and (d) wherein VH and VL-encoding nucleotide sequences are the sequences of VH and VL-encoding nucleotide sequences of one or more cells of the invention.

In a fourteenth configuration, the invention provides:—A method of producing bi-specific 4-chain antibodies wherein the bi-specific antibodies comprise a respective binding site for first and second antigens, wherein the antigens are different, each antibody comprising a first heavy chain-light chain pair and a second heavy chain-light chain pair, wherein (a) the heavy chain of the first heavy chain-light chain pair comprises a first VH, wherein the first VH (when expressed as part of first heavy chains) is capable of pairing with a VL (when expressed as part of light chains) to form a first VH/VL binding site that is capable of specifically binding to the first antigen; and (b) the heavy chain of the second heavy chain-light chain pair comprises a second VH, wherein the second VH (when expressed as part of second heavy chains) is capable of pairing with said VL (when expressed as part of light chains) to form a second VH/VL binding site that is capable of specifically binding to the second antigen;

the method comprising (c) producing a first cell line that is capable of expressing the first heavy chains by (i) inserting into a first cell genome a nucleotide sequence encoding said first VH, wherein the VH sequence is operably inserted 5' of an antibody heavy chain constant region (eg, a human constant region) for expression of first heavy chains comprising first VH and C domains; and (ii) culturing the cell to produce a first cell line that expresses first heavy chains;

(d) producing a second cell line that is capable of expressing the second heavy chains by (i) inserting into a second cell genome a nucleotide sequence encoding said second VH, wherein the VH sequence is operably inserted 5' of an antibody heavy chain constant region (eg, a human constant region) for expression of second heavy chains comprising second VH and C domains; and (ii) culturing the cell to produce a second cell line that expresses second heavy chains;

(e) expressing first heavy chains from the first cell line and second heavy chains from the second cell line and mixing together first heavy chains comprising said first VH, second heavy chains comprising said second VH and light chains comprising said VL, whereby (iii) first heavy chains pair with light chains to produce said first heavy chain-light chain pairs, (iv) second heavy chains pair with light chains to produce said second heavy chain-light chain pairs; and (v) the first heavy chain-light chain pairs pair with the second heavy chain-light chain pairs, thereby producing said bi-specific antibodies wherein VH and/or VL-encoding nucleotide sequences are the sequences of VH and/or VL-encoding nucleotide sequences of one or more cells of the invention.

In a fifteenth configuration, the invention provides:—A method of producing bi-specific 4-chain antibodies wherein the bi-specific antibodies comprise a respective binding site for first and second antigens, wherein the antigens are different, each antibody comprising a first heavy chain-light chain pair and a second heavy chain-light chain pair, wherein (a) the heavy chain of the first heavy chain-light chain pair comprises a first VH, wherein the first VH (when expressed as part of first heavy chains) is capable of pairing with a VL (when expressed as part of light chains) to form a first VH/VL binding site that is capable of specifically binding to the first antigen; and (b) the heavy chain of the second heavy chain-light chain pair comprises a second VH, wherein the second VH (when expressed as part of second heavy chains) is capable of pairing with said VL % (when expressed as part of light chains) to form a second VH/VL binding site that is capable of specifically binding to the second antigen;

the method comprising (c) mixing together first heavy chains comprising said first VH, second heavy chains comprising said second VH and light chains comprising said VL, whereby (i) first heavy chains pair with light chains to produce said first heavy chain-light chain pairs, (ii) second heavy chains pair with light chains to produce said second heavy chain-light chain pairs; and (iii) the first heavy chain-light chain pairs pair with the second heavy chain-light chain pairs, thereby producing said bi-specific antibodies wherein VH and/or VL are encoded by VH and/or VL-encoding nucleotide sequences, wherein the nucleotide sequences are the sequences of VH and/or VL-encoding nucleotide sequences of one or more cells of the invention.

In a sixteenth configuration, the invention provides:—A method of producing a pharmaceutical composition for treating or preventing a disease or condition. (eg, a cancer) in a human or non-human animal subject, the method comprising (a) expressing an antibody from a cell line produced by the method of the invention;

(b) mixing the antibody with a diluent or excipient;

(c) optionally wherein the antibody is identical, to an antibody obtained by the method of the invention.

In a seventeenth configuration, the invention provides:—A method of producing a pharmaceutical composition for treating or preventing a disease or condition. (eg, a cancer) in a human or non-human animal subject, the method comprising mixing a bi-specific antibody with a diluent or excipient, wherein the antibody is identical to an antibody obtained by the method of the invention.

In a eighteenth configuration, the invention provides:—A method of producing a cell or vertebrate of the invention, the method comprising (a) obtaining a nucleic acid comprising a rearranged antibody variable region encoding a rearranged antibody V domain; and (b) inserting the variable region or a copy thereof into the genome of a cell, whereby the variable region is comprised by an antibody locus in said genome, wherein the locus comprises (in 5' to 3' direction)

(c) an antibody locus intronic enhancer;

(d) said rearranged antibody variable region; and (e) an antibody constant region encoding an antibody C domain;

wherein the locus is operable to express an antibody chain comprising (in N- to C-terminal direction) said rearranged V domain and said C domain; and (f) optionally, wherein the cell is a non-human vertebrate ES cell or an iPS cell, the method further comprising generating the non-human vertebrate of the invention from the cell.

In a nineteenth configuration, the invention provides:—A non-human vertebrate (eg, rodent, rat or mouse) blastocyst or pre-morula embryo implanted with an ES or iPS cell according to the invention or obtained according to the method of the invention.

In a twentieth configuration, the invention provides:—A nucleic acid comprising a transgene for use in the method of the invention, the transgene comprising (in 5' to 3' direction)

(a) said intronic enhancer;

(b) said rearranged antibody variable region; and (c) said antibody constant region.

In a twenty-first configuration, the invention provides:—A nucleic acid comprising a rearranged variable region sequence encoding a rearranged V domain for use in the method of the invention, the nucleic acid comprising said rearranged variable region sequence flanked (a) 5' by a homology arm for hybridising to a first nucleotide sequence of the cell genome, and/or (b) 3' by a homology arm for hybridising to a second nucleotide sequence of the cell genome; Wherein (c) the first nucleotide sequence is homologous to a sequence of an antibody light chain (eg, kappa) locus of the cell 5' of the CL region thereof, and the second nucleotide sequence is homologous to a sequence of said locus 3' of the intronic enhancer (eg, Eric) of the locus, whereby homologous recombination between the homology arms and the genome of the cell is capable of inserting the variable region sequence, thereby producing a locus comprising (in 5 to 3' direction) an intronic enhancer, said variable region and a CL region; or (d) the first nucleotide sequence is homologous to a sequence of a heavy chain antibody locus of the cell 5' of the Cμ region thereof, and the second nucleotide sequence is homologous to a sequence of said locus 3' of the intronic enhancer (Eμ) of the locus, whereby homologous recombination between the homology arms and the genome of the cell is capable of inserting the variable region sequence, thereby producing a locus comprising (in 5 to 3' direction) an intronic enhancer, said variable region and a Cμ region.

Further exemplification is provided below by way or worked experiments and data.

BRIEF DESCRIPTION OF THE DRAWINGS

FIG. 1 A schematic of the targeting strategy of generating a common light chain allele. The mouse κ intronic enhancer and mouse κ constant region (4.6 kb) in mouse ES cells were replaced by a synthesised DNA fragment of 6.8 kb, which contains a EFla-Puro-2A-EGFP cassette, the natural promoter and signal peptide of human vλ 3-21, mouse κ intronic enhancer, as well as a recombined human common lambda light chain allele from an antibody that specifically binds Target X.

FIGS. 3A-F are sorting plots and show the flow of sorting. The cells selected in the first sort were used for the subsequent sort and the selection process continued. FIG. 3A. Sorting plot selecting lymphocytes. SSC-A (side scatter area) versus FSC-A (forward scatter area). FIG. 3B. Sorting plot selecting single cells. FSC-W (forward scatter width) versus FSC-A (forward scatter area). FIG. 3C. Sorting plot selecting single cells. SSC-W (side scatter width) versus SSC-A (side scatter area). FIG. 3D. Sorting plot selecting live cells. SSC-A (side scatter area) versus live/dead 7-AAD. FIG. 3E. Sorting plot selecting CD19$^+$ B-cells. Y-axis indicates markers used versus CD19-PB. FIG. 3F. Sorting plot of B-cells that express human lambda light chain and specifically bind human Target X. Human Target X antigen labelled with AF647 versus human lambda light chain labelled with PE.

8 blastocysts micro-injected with targeted ES cells (targeted Rag$^{7''}$) was similar to wild-type mice (Wild-Type).

Figure 9:
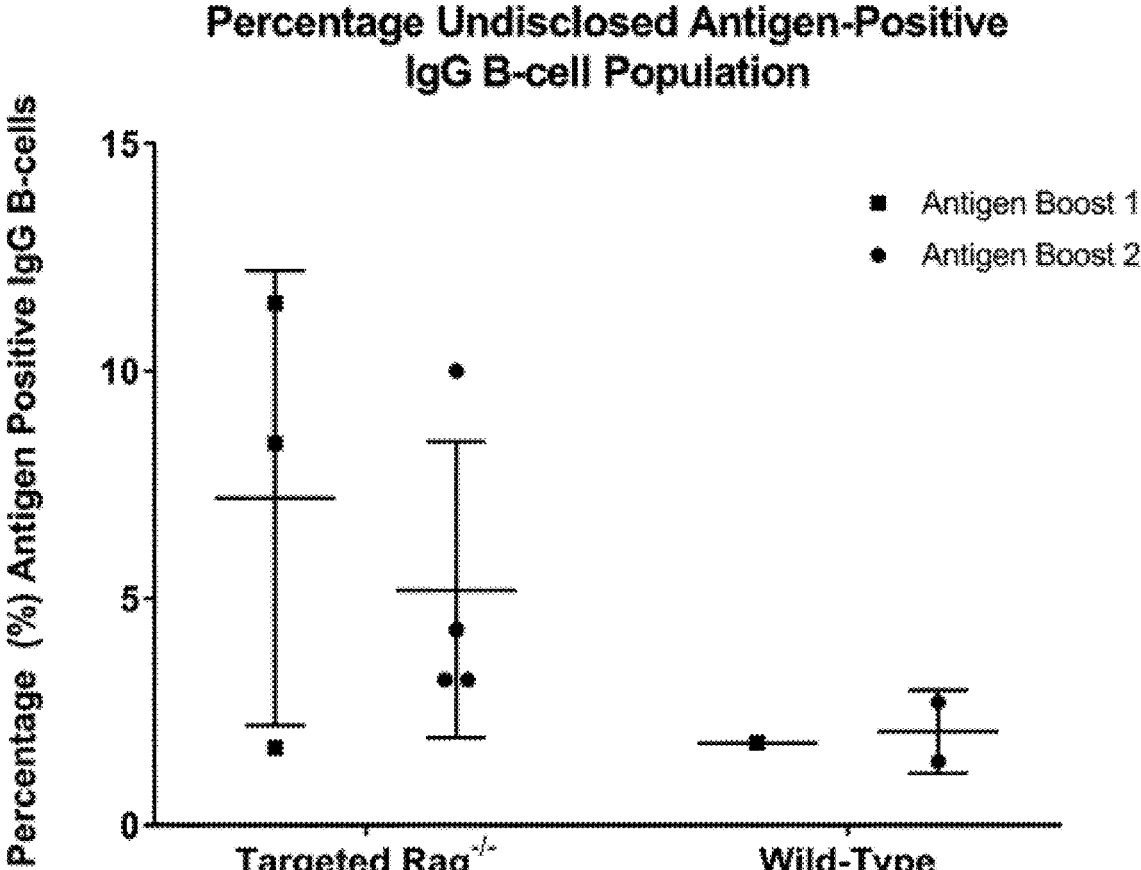

FIG. 9 Percentage antigen positive IgG B-cell population in chimera mice generated from Rag$^{7''}$ blastocysts micro-injected with targeted ES cells (targeted Rag$^7$) was similar to wild-type mice (Wild-Type).

DETAILED DESCRIPTION

Aspects herein may be expressed in terms of the non-human vertebrate being a mouse, but it is to be understood that rodents, rats, rabbits or any other non-human vertebrate may be suitable for performing the present invention.

The inventors realised that the provision in an antibody light or heavy chain locus of a V domain coding variable region sequence 3' of the intronic enhancer in an antibody chain locus minimises SHM of the V region, which allows the invention to be used to identify true common light or heavy chains. In some embodiments, the locus is a modified version of an endogenous antibody locus of a wild-type or transgenic vertebrate cell or non-human vertebrate. In other embodiments, the locus is not at an endogenous antibody chain locus, but instead is comprised by a locus inserted at Rosa 26 or another location where the locus is capable of expressing antibody chains. For example, the locus of the invention is comprised by a randomly inserted transgene in the cell or vertebrate genome. By minimising or eliminating SHM of the V region, a single (ie, "common") light chain is more likely to be expressed by the cell or such cells comprised by the vertebrate. When SHM is eliminated the variable region expresses only a single type of VL domain which may pair with different VH domains expressed by the vertebrate, thereby allowing screening and identification of one or more VH domains that may functionally pair with the VL to form VH/VL binding sites for an antigen or epitope. Even if some mutation may occur, the invention restricts the possibility of this so that the purity of VL domains produced by the same V-J recombination is likely to be such that a single rearranged VL by far predominates (eg, at a level of at least 95% or 100% as described further below). Usefully, therefore, the expression of a desired common light chain can be pre-determined (eg, by providing a known variable region (or light chain) sequence in the locus or transgene, such as a known rearranged variable region (or light chain) sequence encoding a VL (or light chain) of a known antibody that can specifically bind to a predetermined antigen or epitope. Advantageously, the ability in embodiments to use a light chain sequence (eg, a human rearranged VKJCK of a predetermined human antibody of known binding specificity and/or affinity for an antigen or epitope) is useful as pairings and selection in vivo in the vertebrate of the invention is then possible in the context of the complete human light chain that will be used in a final antibody product (eg, a bispecific antibody medicament).

Optionally, the common light chain comprises or consists of the amino acid sequence of SEQ ID NO: 1, or an amino acid sequence that is at least 70, 75, 80, 85, 90, 95, 96, 97, 98 or 99% identical thereto. Optionally, the variable domain of the common light chain comprises or consists of the variable domain of the light chain sequence of SEQ ID NO: 1, optionally with 5 or less, 4 or less, 3 or less, 2 or 1 amino acid change. Each change can be an amino acid deletion, substitution or addition. In an example, the sequence of the variable domain is determined by Kabat numbering. In an example, the sequence of the variable domain is determined by IMGT numbering.

An example of an in vivo approach using the chimaeric mouse (or other no-human vertebrate) to identify common light chains for multi- or bi-specific antibodies is provided, wherein B cells from the mouse are derived from ES cells with rearranged light chain loci and expressing an immunoglobulin light chain repertoire with a single or highly limited number of light chain variable domains. The chimeric mouse is, for example, generated from wild type, RAG knock-out or IgH knock-out mouse blastocysts injected with mouse ES cells carrying the knock-in rearranged human light chain encoding sequence and an unrearranged human or endogenous IgH locus. The DNA sequence of the rearranged human light chain is inserted such that it may be free of somatic hypermutation (SHM). Methods for making such a chimaeric mouse or other non-human vertebrate expressing common light chains are provided. Methods for identify antigen-specific common light chain antibodies useful as bispecific antibodies (eg, for cancer therapy in a human) are provided, as are such antibodies per se and cells expressing these.

A particular example work flow may be:—1. Obtaining a first antibody comprising first human VH and VL domains, wherein the antibody specifically binds to a first predetermined antigen; or obtaining nucleotide sequences encoding said VL or the light chain of the antibody;

Obtaining a transgenic mouse ES cell comprising an IgH locus (in heterozygous or homozygous form), wherein the IgH locus comprises a humanised variable region for expressing a plurality of different human VH domains;

Inserting a nucleotide sequence encoding the light chain of the antibody or the VL thereof into the genome of the ES cell, wherein the insertion is between the Eιк and CK of a kappa locus allele of the ES cell genome;

Optionally modifying the other kappa locus allele so that it is not capable of expressing kappa light chains, or modifying the allele whereby a nucleotide sequence encoding the light chain of the first or a second antibody or the VL thereof is inserted between the Eιк and CK of said other kappa locus allele;

Developing the ES cell into a mouse (eg, by implanting the ES cell into a recipient blastocyst or pre-morula embryo (eg, a RAG and/or IgH knock-out blastocyst or pre-morula embryo) and implanting the blastocyst or pre-morula embryo into a pseudopregnant female mouse, whereby one or more pups are birthed from the female), wherein the mouse or pup(s) so developed comprises at least one kappa locus that is capable of expressing the light chain or VL, wherein the light chain or VL pair with heavy chains or VH expressed by the mouse to form VH/VL antigen binding sites;

Optionally obtaining progeny mice, wherein the progeny each comprise at least one kappa locus that is capable of expressing the light chain or VL, wherein the light chain or VL pair with heavy chains or VH expressed by the progeny mouse to form VH/VL antigen binding sites;

Immunizing the mouse of step 5 or a said progeny mouse with a second antigen, wherein the first and second antigens are different;

Obtaining from an immunised mouse of step 7 (eg, using PCR of DNA of a B-cell and/or hybridoma technology of a B-cell of an immunised mouse of step 7) a nucleotide sequence encoding a VH (second VH) that pairs with the VL (or a VH of a heavy chain that pairs with the VL of the light chain), wherein the second VH and VL form an antigen binding site that specifically binds to the second antigen;

Optionally inserting a nucleotide sequence encoding the first VH, a nucleotide sequence encoding the second VH, and a nucleotide sequence encoding the VL into one or more expression vectors or into the genome of one or more host cells, each V nucleotide sequence being in operable connection 5' of an antibody first CH, second CH or CL region respectively for expression of first antibody heavy chains, second antibody heavy chains or antibody light chains respectively; optionally wherein the first and second CH regions encode first and second CH domains that are mutated human CH domains that pair together (eg, using charge pair mutation or knob-in-hole mutation) and/or wherein the first and second chains have different pi (eg, separated by 0.5-1 pi unit);

10. Optionally obtaining host cells of step 9 and expressing the heavy and light chains in the host cells, whereby bi-specific antibodies are produced each comprising a first heavy chain/light chain pair comprising a VH/VL binding site that is capable of specifically binding to the first antigen, and a second heavy chain/light chain pair comprising a VH/VL binding site that is capable of specifically binding to the second antigen; and 11. Optionally isolating said bi-specific antibodies.

In an alternative, first and second epitopes of an antigen are used instead of first and second antigens. In an embodiment, the method comprises steps 1 to 8; 1 to 9; 1 to 10 or 1 to 11. In an example, there is provided a method for obtaining a bispecific antibody, the method commencing at step 7. In an example, there is provided a method for obtaining a bispecific antibody, the method commencing at step 8. In an example, there is provided a method for obtaining a bispecific antibody, the method commencing at step 9. In an example, there is provided a method for obtaining a bispecific antibody, the method commencing at step 10. In an example, there is provided a method for obtaining a bispecific antibody, the method commencing at step 11.

In an example, the light chain repertoire of each mouse used in step 7 is at least 95, 96, 97, 98 or 99% pure (or 100% pure) for the VL. This can be determined, for example, by obtaining a B-cell sample (eg, spleen and/or bone marrow B-cell sample) from the mouse, obtaining VL-encoding nucleotide sequences thereof (eg, m NA or cDNA) and carrying out next-generation sequencing (NGS) to determine the percentage of the VL (and any other VL species) in the sampled nucleotide sequences. The skilled person will be familiar with routine NGS techniques. Thus, for example, herein "95% pure" in respect of the VL means that the repertoire (eg, a sampled repertoire of the mouse) comprises sequences (eg, mRNA, cDNA or DNA) encoding said predetermined VL in a proportion in the repertoire or sample of 95% or higher, eg, as determined by NGS. In an embodiment, all of (or substantially all of) the VL domains expressed by the mouse are identical to the VL of the antibody of step 1. This may be advantageously be achieved due to the positioning according to the invention of the VL-encoding sequence 3' of the intronic enhancer, such as between this enhancer and the constant region.

In an alternative, the VL-encoding variable region sequence (eg, in steps 3 and 4 above) is an insert in the lambda locus allele(s) of the cell or mouse between mouse lambda 2-4 and CX or between mouse lambda 4-10 enhancer and CX. Additionally, in an embodiment the VL-encoding variable region sequence is an insert in the kappa locus allele(s) of the cell or mouse between Eιк and CK.

In an alternative, only one of the lambda locus alleles comprises a said insert; and only one of the kappa locus alleles comprises a said insert.

The VL-encoding variable region inserts in the lambda and kappa, or in the 2 lambda or in the 2 kappa alleles may be the same or different (ie, encode the same or different VLs, such as VLs of 2 different antibodies of predetermined specificity for the same or different antigens).

In an embodiment, first and second mouse (or other non-human vertebrate, such as rat) ES cells are modified to comprise first and second loci of the invention, eg, each cell being modified according to steps 1 to 4, but wherein the VL-encoding nucleotide sequence inserts in the cells are different (ie, encode different VL domains, such as VL domains of different antibodies of different antigen or epitope specificity). The first and second ES cells (or progeny thereof) are implanted into the same blastocyst or pre-morula embryo and a mouse (or progeny thereof) developed, wherein the mouse or progeny express said different VL domains for pairing with VH domains (eg, human VH) expressed by the mouse or progeny.

Advantageously, a first generation mouse (ie, grown directly from the ES cell-implanted blastocyst or pre-morula herein) is useful as it can be immunised without the need for further breeding to subsequent generation mice. This saves time and complexity of breeding. It may be desirable, for example, for the blastocyst or pre-morula that receives the ES cell implant to comprise a knock-out of its IgH loci or be a RAG knock-out, as this forces all productive B-cells produced in the first generation mouse (or subsequent generation mice) to be ES cell derived, thereby ensuring that all productive B-cells comprise one or more loci of the invention.

Optionally, thus generally it may advantageously not be necessary to obtain germline transmission of the loci of the invention in non-human vertebrate progeny or lineages, instead it is possible to work with chimaera vertebrates grown from the blastocyst or pre-morula embryo which provides significant time advantages over prior art techniques where germline transmission of light chain allele modifications is described. Thus, in one embodiment, a mouse or vertebrate of the invention is a chimaera comprising a first plurality of cells of the invention and a second plurality of cells that are not according to the invention (eg, wild-type or transgenic cells that do not comprise a locus of the invention). Optionally, the chimaera may comprise a third plurality of cells according to the invention comprising loci according to the invention but that are capable of expressing V domains that are different from the V domains expressed by the loci of the invention of the first plurality of cells. Thus, it is possible to develop a chimaeric vertebrate that can express first and second VL domains that are different but which are predetermined as they are expressed from loci of the invention. It may be advantageous to knock out expression of one or more light and/or heavy chain loci of the second plurality of cells so that heavy and light chains in the vertebrate are only contributed by the first and optional third plurality of cells. In addition or alternatively, the second plurality of cells may have a RAG (eg, RAG-1 and/or RAG-2) knock-out to eliminate antibody chain contribution from such cells in the vertebrate.

In an alternative configuration, it is recognised that such generation and use of chimaeras and first generation non-human vertebrates of the invention is advantageous as so described due to the lack of need for breeding and time saving, and this is not dependent upon the feature of the invention directed to providing the variable region insert 3' of the intronic enhancer. Thus, an alternative configuration is provided wherein any feature herein is mutatis mutandis applicable with the alternative that the locus of the invention comprises said variable region 5' of the intronic enhancer, whereby the locus is capable of expressing an antibody chain comprising the V and C domains.

Furthermore, in the alternative configuration, the variable region may be an unrearranged variable region comprising a plurality of VH gene segments, one or more D gene segments and one or more JH gene segments, wherein the variable region is capable of rearranging for the expression of a plurality of different VH domains; or the variable region may be an unrearranged variable region comprising a plurality of VL gene segments and one or more JH gene segments, wherein the variable region is capable of rearranging for the expression of a plurality of different VL domains; or only one two, three, four or five rearranged variable regions may be 5' of the enhancer for expressing a restricted diversity of V domains (eg, VL domains). Particularly, this configuration is useful wherein the vertebrate is a chimaera, such a first generation vertebrate as described herein. This alternative configuration of the invention also provides for a method of immunizing such a chimaera or vertebrate with an antigen and isolating an antibody that specifically binds to the antigen, a VH domain thereof, a VL domain thereof, or a nucleotide sequence encoding any of these. Beneficially, this method is streamlined by the possibility of immunizing a vertebrate that is produced without need for breeding cycles.

A V domain or binding site that "specifically binds to" or is "specific for" a particular antigen or epitope is one that binds to that particular antigen or epitope without substantially binding to other antigens or epitopes. For example, binding to the antigen or epitope is specific when the antibody binds with a $K_D$ of 1mM or less, eg, 100 μM or less, 10 μM or less, 1 μM or less, 100 nM or less, eg, 10 nM or less, 1 nM or less, 500 μM or less, 100 μM or less, or 10 μM or less. The binding affinity ($K_D$) can be determined using standard procedures as will be known by the skilled person, eg, binding in ELISA and/or affinity determination using surface plasmon resonance (eg, Biacore™, Proteon™ or KinExA™ solution phase affinity measurement which can detect down to f affinities (Sapidyne Instruments, Idaho)). In one embodiment, the surface plasmon resonance (SPR) is carried out at 25° C. In another embodiment, the SPR is carried out at 37° C. In one embodiment, the SPR is carried out at physiological pH, such as about pH7 or at pH7.6 (eg, using Hepes buffered saline at pH7.6 (also referred to as HBS-EP)). In one embodiment, the SPR is carried out at a physiological salt level, eg, 150 mM NaCl. In one embodiment, the SPR is carried out at a detergent level of no greater than 0.05% by volume, eg, in the presence of P20 (polysorbate 20; eg, Tween-20™) at 0.05% and EDTA at 3 mM. In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity is determined using SPR by

1. Coupling anti-mouse (or other relevant non-human vertebrate, to match the C region of an antibody for example) IgG (eg, Biacore BR-1008-38) to a biosensor chip (eg, GLM chip) such as by primary amine coupling;

2. Exposing the anti-mouse IgG (non-human vertebrate antibody) to a test IgG antibody or heavy chain to capture test antibody on the chip;

3. Passing the test antigen over the chip's capture surface at 1024 nM, 256 nM, 64 nM, 16 nM, 4 nM with a 0nM (i.e. buffer alone); and 4. And determining the affinity of binding of test antibody/chain to test antigen using surface plasmon resonance, eg, under an SPR condition discussed above (eg, at 25° C. in physiological buffer).

SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, eg, using a model inherent to the ProteOn XPR36™ analysis software.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2) having paired VH/VL antigen binding site(s).

A "domain" is a folded protein structure which has tertiary structure independent of the rest of the protein. Generally, domains are responsible for discrete functional properties of proteins and in many cases may be added, removed or transferred to other proteins without loss of function of the remainder of the protein and/or of the domain.

Optionally, any multispecific antibody herein is a bispecific antibody. This includes formats such as DVD-lg, mAb$^2$, FIT-lg, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, TriBi minibody, scFv-CH-3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-lgG, DutaMab, lgG(HI)-scFv, scFv-(H)lgG, lgG(L)-scFv, scFv-(L)lgG, lgG(L,H)-Fv, lgG(H)-V, V(H)-lgG, lgG(L)-V, V(L)-lgG, KIH lgG-scFab, 2scFv-lgG, lgG-2scFv, scFv4-lg and zybody. For a review of bispecific formats, see Spiess, C, et al., Mol. Immunol. (2015). Optionally, the multispecific ligand is a DVD-lg, mAb$^2$, FIT-lg, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, minibody, knobs-in-holes ligand, knobs-in-holes ligand with common light chain, knobs-in-holes ligand with common light chain and charge pairs, charge pairs, ligand having charge pairs with common light chain; in each case comprising at least one VH/VL antigen binding site.

Optionally, the rearranged variable region (eg, a rearranged variable region encoding a VL, vλ or VK domain, eg, a human domain) in the light chain locus comprises upstream one of the following pairs of promoter and signal peptide (ie, promoter, SP and V region in 5' to 3' order):—

) Mouse vλ promoter+Mouse vλ SP
) Mouse V\ promoter+Non-mouse rodent V\SP
) Mouse V\promoter+Human V\SP
) Mouse V\promoter+Non-human primate vλ SP
) Mouse VK promoter+Mouse V\SP

14

) Mouse VK promoter+Non-mouse rodent vλ SP
) Mouse VK promoter+Human V\SP
) Mouse VK promoter+Non-human primate vλ SP
) Non-mouse rodent vλ promoter+Mouse V SP
0) Non-mouse rodent vλ promoter+Non-mouse rodent vλ SP 1) Non-mouse rodent vλ promoter+Human vλ SP
2) Non-mouse rodent vλ promoter+Non-human primate V\SP
3) Non-mouse rodent VK promoter+Mouse V\SP
4) Non-mouse rodent VK promoter+Non-mouse rodent vλ SP 5) Non-mouse rodent VK promoter+Human vλ SP
6) Non-mouse rodent VK promoter+Non-human primate V\SP
7) Human vλ promoter+Mouse vλ SP
8) Human vλ promoter+Non-mouse rodent vλ SP
9) Human vλ promoter+Human vλ SP
0) Human V\promoter+Non-human primate vλ SP
1) Human VK promoter+Mouse vλ SP
2) Human VK promoter+non-mouse rodent V\SP
3) Human VK promoter+Human vλ SP
) Human VK promoter+Non-human primate vλ SP
) Non-human primate vλ promoter+Mouse vλ SP
) Non-human primate vλ promoter+Non-mouse rodent vλ SP Non-human primate vλ promoter+Human vλ SP
Non-human primate vλ promoter+Non-human primate vλ SP
) Non-human
) Non--human
) Non--human
) Non--human
Mouse vλ promoter+Mouse VK SP
Mouse V\promoter+Non-mouse rodent VK SP
Mouse V\promoter+Human VK SP
Mouse V\promoter+Non-human primate VK SIP
Mouse VK promoter+Mouse VK SP
Mouse VK promoter+Non-mouse rodent VK SP
Mouse VK promoter+Human VK SP
Mouse VK promoter+Non-human primate VK SP
) Non--mouse rodent vλ promoter+Mouse VK SP
) Non--mouse rodent vλ promoter+Non-mouse rodent VK SP) Non--mouse rodent vλ promoter+Human VK SP
) Non--mouse rodent vλ promoter+Non-human primate VK SP
) Non--mouse rodent VK promoter+Mouse VK SP
) Non--mouse rodent VK promoter+Non-mouse rodent VK SP) Non--mouse rodent VK promoter+Human VK SP
) Non--mouse rodent VK promoter+Non-human primate VK SP
Human vλ promoter+Mouse VK SP
Human vλ promoter+Non-mouse rodent VK SP
Human vλ promoter+Human VK SP
Human vλ promoter+Non-human primate VK SP
53) Human VK promoter+Mouse VK SP
54) Human VK promoter+non-mouse rodent VK SP
55) Human VK promoter+Human VK SP
56) Human VK promoter+Non-human primate VK SP
57) Non-human primate vλ promoter+Mouse VK SP
58) Non-human primate vλ promoter+Non-mouse rodent VK SP
59) Non-human primate vλ promoter+Human VK SP
60) Non-human primate vλ promoter+Non-human primate VK SP
61) Non-human primate VK promoter+Mouse VK SP

US 12,696,885 B2

15

62) Non-human primate VK promoter+Non-mouse rodent VK SP
63) Non-human primate VK promoter+Human VK SP
64) Non-human primate VK promoter+Non-human primate VK SP Example rodents are rat, beaver, gopher, hamster, gerbil, porcupine, chinchilla, lemming or vole. Example non-human primates are chimpanzee, ape, gorilla, orangutan, simian, monkey (eg, rhesus macaque or cynonmnolgus monkey), lemur or baboon. Sources of sequences for the promoter and/or SP include, for example, ww.imgt.org, www.ensembl.org and sequences obtained using a sample (eg, blood sample and PCR of the sequence) from such a rodent or primate or human, as will be readily apparent to the skilled addressee.

In an example, the light chain locus of the cell, vertebrate, mammal or mouse of the invention is devoid of a selection marker. In the examples below, a selection marker was retained and the locus performed desirably. In an alternative, an 0 selection marker can be included when constructing the locus, followed by excision of the marker before developing the vertebrate or mouse. In an example the marker is flanked by piggyBac terminal repeats and PBase is transiently expressed in the ES cell in which the locus has been constructed, thereby excising the marker. In an example, the marker compriss puro-delta-tk flanked by piggyBac terminal repeats.

The invention can be illustrated by the following Statements.
Statements:
1. A cell comprising an antibody light chain locus (first locus), wherein the locus comprises (in 5' to 3' direction)
(a) a light chain intronic enhancer;
(b) a rearranged antibody variable region encoding a rearranged antibody V domain (eg, a VH, V\ or VK, eg, a VL); and
(c) an antibody light chain constant region encoding a light chain C domain;
wherein the locus is operable to express an antibody chain comprising (in N- to C-terminal direction) said rearranged V domain and said C domain.

For example, the V domain and C domain are human. For example, the V domain and C domain are a human VK and a human CK, eg, as comprised by a known antibody that binds a predetermined antigen (eg, the first antigen mentioned above). For example, the V domain and C domain are a human vλ and a human CX, eg, as comprised by a known antibody that binds a predetermined antigen (eg, the first antigen mentioned above). For example, the cell is a rodent, rat our mouse cell.

Optionally, the variable domain comprises or consists of the variable domain of the light chain sequence of SEQ ID NO: 1, optionally with 5 or less, 4 or less, 3 or less, 2 or 1 amino acid change. Each change can be an amino acid deletion, substitution or addition. In an example, the sequence of the variable domain is determined by Kabat numbering. In an example, the sequence of the variable domain is determined by IMGT numbering. Optionally, the variable domain specifically binds to a protein antigen, eg, a human protein antigen.

For example, the cell is a rodent, rat our mouse cell and the V domain and C domain are a human VK and a mouse CK, eg, as comprised by a known antibody that binds a predetermined antigen (eg, the first antigen mentioned above); or the V domain and C domain are a human vλ and

16 a mouse CX, eg, as comprised by a known antibody that binds a predetermined antigen (eg, the first antigen mentioned above).

In an example, the constant region encodes a CK or a CX and there is no further C domain-encoding nucleotide sequence 3' of said constant region.

Preferably, the V domain is capable of specifically binding an antigen, eg, a human antigen, such as when comprised by a VH/VL binding site of an antibody.

Optionally, a cell of the invention is a vertebrate, mammalian, non-human mammalian, rodent, mouse, rat or human cell. Optionally, the cell is a human or rodent (eg, a mouse or a rat) cell. Optionally, the cell or mouse is a 129 or C57BL/6 strain cell or mouse (eg, a hybrid 129 or hybrid C57BL/6 strain cell or mouse). Optionally, the cell or mouse is a hybrid 129/C57BL/6 strain cell or mouse, such as a F1H4 strain cell or mouse.

Optionally, the locus is comprised by a transgene randomly inserted in the cell genome, or at a position outside an endogenous antibody locus of the cell. Optionally, the locus is at an endogenous antibody locus of the cell. Optionally, the locus is immediately adjacent to an endogenous antibody locus of the cell, or within 10, 5, 1 or 0.5 kb of an endogenous antibody locu of the cell, such as 3' or 5' thereof. Optionally, the enhancer and/or constant region is an endogenous antibody locus enhancer or constant region of the cell. Optionally, the constant region is 5' of (eg, immediately 5' of or within 500, 400, 300, 200, 100 or 50 bp 5' of) an endogenous antibody locus constant region of the cell. For example, the constant region (eg, a human CK or CX) of the locus of the invention is immediately 5' of or within 500, 400, 300, 200, 100 or 50 bp 5' of an endogenous CK constant region of the cell.

Optionally, in any cell of the invention, the antibody variable region is no more than 400, 300, 200, 150, 100, 50, 30, 20, 10 or 5 bp 3' (or 5' in the alternative configuration) of the enhancer of the locus.

Optionally, in any cell of the invention, the antibody variable region is no more than 400, 300, 200, 150, 100, 50, 30, 20, 10 or 5 bp 5' of the constant region of the locus.

In an alternative configuration, the antibody variable region is 3' of the 3' enhancer of an endogenous antibody (eg, kappa or lambda) locus of the cell (eg, wherein the cell is a rodent, mouse or rat cell). Optionally in this configuration, the antibody variable region is no more than 400, 300, 200, 150, 100, 50, 30, 20, 10 or 5 bp 3' of the 3' enhancer.

In an example, the constant region of the locus of the invention is an endogenous antibody constant region of the cell (eg, wherein the cell is a rodent, mouse or rat cell). In another example, the constant region of the locus of the invention is a human antibody constant region (eg, wherein the cell is a rodent, mouse or rat eel), optionally wherein the human constant region is 5' of an endogenous antibody constant region of the cell (eg, an endogenous CK or CX).

For example, the locus comprises (in 5' to 3' direction)
(a) a light chain intronic enhancer;
(b) a rearranged antibody human variable region encoding a rearranged antibody V domain (eg, a human V domain);
(c) a human or mouse or rat antibody light chain constant region encoding a light chain C domain;
wherein the locus is operable to express an antibody chain comprising (in N- to C-terminal direction) said rearranged V domain and said C domain.

For example, the locus comprises (in 5' to 3' direction)
(a) a light chain intronic enhancer;

(b) a rearranged antibody variable region encoding a rearranged antibody V domain (eg, a human V domain);

(c) an exogenous antibody light chain constant region (eg, a human CK or CX) encoding a light chain C domain; and (d) an endogenous antibody light chain constant region of the cell (eg, wherein the cell is a rodent, mouse or rat cell.)

wherein the locus is operable to express an antibody chain comprising (in N- to C-terminal direction) said rearranged V domain and said C domain.

For example, the locus comprises (in 5' to 3' direction)

(a) an endogenous light chain intronic enhancer of the cell (eg, wherein the cell is a rodent, mouse or rat cell);

(b) a rearranged antibody variable region encoding a rearranged antibody V domain (eg, a human V domain);

(c) an antibody light chain constant region encoding a light chain C domain (eg, a human C domain, such as when the cell is a rodent, mouse or rat cell); and (d) optionally an endogenous antibody light chain constant region of the cell;

wherein the locus is operable to express an antibody chain comprising (in N- to C-terminal direction) said rearranged V domain and said C domain.

Preferably, the intronic enhancer is an endogenous enhancer of the cell (eg, wherein the cell is a rodent, mouse or rat cell), preferably a kappa locus Eικ enhancer. Preferably, the cell is a cell of a first species or strain (eg, a mouse or rat species or strain) and the intronic enhancer of the invention comprises a wild-type intronic enhancer sequence of said species or strain. For example, the cell is a F1H4, 129 or C57BL6 strain cell and the enhancer is an intronic enhancer of said strain; optionally wherein the enhancer is a Eικ and/or the variable region is an insert upstream of an endogenous kappa constant region of the cell (eg, between an endogenous variable region of the cell (such as a human or mouse variable region in a mouse cell) and an endogenous CK (eg, mouse CK) of a kappa locus of the cell).

The cell of Statement 1, wherein the locus is a kappa light chain locus and the enhancer is Eικ.

In an example the enhancer is Eικ, eg, and the locus is a lambda light chain locus. Preferably in this example or Statement, the V domain and C domain are a human VK and a human CK, eg, as comprised by a known antibody that binds a predetermined antigen (eg, the first antigen mentioned above); or the V domain and C domain are a human vλ and a human CX, eg, as comprised by a known antibody that binds a predetermined antigen (eg, the first antigen mentioned above), wherein example, the cell is a rodent, rat our mouse cell.

For example, the locus is a kappa light chain locus and the enhancer is Eικ, the cell is a mouse cell, and the V domain and C domain are a human VK and a human CK, eg, as comprised by a known antibody that binds a predetermined antigen (eg, the first antigen mentioned above). For example, the locus is a kappa light chain locus and the enhancer is Eικ, the cell is a mouse cell, and the V domain and C domain are a human vλ and a human CX, eg, as comprised by a known antibody that binds a predetermined antigen (eg, the first antigen mentioned above).

In an embodiment, the cell is a rodent, mouse or rat cell and the enhancer is a rodent, mouse or rat intronic enhancer (eg, Eικ) respectively.

In an example the light chain constant region is a CK and the locus comprises a kappa 3' enhancer that is operably connected 3' of the CK. In another example, the light chain constant region is a CX.

Optionally, the constant region is a human constant region. Optionally, the constant region is a mouse constant region. Optionally, the constant region is a rat constant region.

Optionally, the constant region is a human CK. Optionally, the constant region is a mouse CK. Optionally, the constant region is a rat CK.

Optionally, the constant region is a human CX. Optionally, the constant region is a mouse CX. Optionally, the constant region is a rat CX.

Optionally, the enhancer is a human enhancer. Optionally, the enhancer is a mouse enhancer.

Optionally, the enhancer is a rat enhancer.

Optionally, the enhancer is a human Eικ enhancer. Optionally, the enhancer is a mouse Eικ enhancer. Optionally, the enhancer is a rat Eικ enhancer.

Optionally, the enhancer is a human lambda enhancer. Optionally, the enhancer is a mouse lambda enhancer. Optionally, the enhancer is a rat lambda enhancer.

In an example, the enhancer is immediately flanked 5' and/or 3' by human kappa or lambda variable region intron sequence (eg, wherein the enhancer is a mouse enhancer and the cell is a mouse or rat cell; or wherein the enhancer is a rat enhancer and the cell is a mouse or rat cell). Optionally, each flanking sequence is a sequence comprised by a human VL intron between a signal peptide-encoding sequence and a VL-encoding sequence of a nucleotide sequence encoding said V domain (wherein the V domain is said VL). For example, the locus comprises a genomic fragment of a B-cell that is capable of expressing the VL domain (or a light chain comprising the VL), wherein the fragment comprises (in 5' to 3' order) a promoter, a VL signal peptide-encoding sequence, a first intron sequence, said enhancer, as second intron sequence, the variable region and optionally the constant region, wherein the first and second intron sequences are naturally contiguous in the B-cel genome or are spaced by no more than 500, 400, 300, 200, 100, 50 or 20 bp (bp=base pairs).

For example, the locus comprises a nucleotide sequence that encodes a rearranged light chain (eg, a kappa or lambda chain) of an antibody (eg, wherein the antibody specifically binds to a predetermined antigen or epitope). For example, said nucleotide sequence is comprised by a cloned genomic fragment from an antibody-producing cell, such as a B-cell or hybridoma, that expresses the antibody. In an example, the nucleotide sequence is a cloned genomic sequence of said antibody-producing cell comprising a sequence from a promoter of said variable region to (and including) the variable region and optionally also to (and including) the constant region operably linked to the variable region. For example, the cell is a mouse or rat cell and the genomic fragment comprises the sequence of a genomic fragment of a kappa antibody-producing cell that is specific for a predetermined antigen, wherein the genomic sequence comprises the nucleotide sequence from a promoter of said variable region to (and including) the variable region; optionally wherein the sequence is comprised by the locus of the invention 5' of a human CK constant region of the locus. For example, the cell is a mouse or rat cell and the genomic fragment comprises the sequence of a genomic fragment of a lambda antibody-producing cell that is specific for a predetermined antigen, wherein the genomic sequence comprises the nucleotide sequence from a promoter of said variable region to (and including) the variable region; optionally wherein the sequence is comprised by the locus of the invention 5' of a human CX or CK constant region of the locus. In an example, the nucleotide sequence is an insert in a kappa or lambda locus of the cell, eg, operably linked 5' of an endogenous 3' enhancer of the kappa or lambda locus of the cell.

In an example of any cell, vertebrate or other aspect of the invention herein, endogenous lambda and/or kappa chain expression of the cell or vertebrate is inactive or substantially inactive. In an embodiment, inactivation is more than 50% (ie, 50% or less of the antibodies or transcripts are of a said endogenous antibody chain), 60%, 70%, 80%, 85%, 90%, 95%, 96%, 97%, 98% or 99%. For example, in an embodiment, said endogenous lambda chain expression is substantially inactive such that no more than 85%, 90%, 95%, 96%, 97%, 98% or 99% of the lambda chain repertoire of the vertebrate is provided by endogenous lambda chains. For example, endogenous lambda chain expression is inactive such that none or substantially none of the lambda chain repertoire of the vertebrate is provided by endogenous lambda chains. For example, in an embodiment, said endogenous kappa chain expression is substantially inactive such that no more than 85%, 90%, 95%, 96%, 97%, 98% or 99% of the kappa chain repertoire of the vertebrate is provided by endogenous kappa chains. For example, endogenous kappa chain expression is inactive such that none or substantially none of the kappa chain repertoire of the vertebrate is provided by endogenous kappa chains.

In an example, the locus of the invention is a modification of an endogenous kappa locus allele of the cell, and optionally the cell is heterozygous or homozygous for said modification. In an embodiment, the cell is heterozygous for the modification and the cell comprises a wild-type or humanised locus at the other kappa locus allele.

In an example, the locus of the invention is a modification of an endogenous lambda locus allele of the cell, and optionally the cell is heterozygous or homozygous for said modification. In an embodiment, the cell is heterozygous for the modification and the cell comprises a wild-type or humanised locus at the other lambda locus allele.

3. The cell of Statement 1, wherein the cell is a mouse cell, locus is a lambda light chain locus and the enhancer is a mouse lambda 2-4 or 4-10 enhancer.

4. The cell of any preceding Statement, wherein
(a) the rearranged V domain is a VK and the C domain is a CK;
(b) the rearranged V domain is a VK and the C domain is a CX;
(c) the rearranged V domain is a vλ and the C domain is a CX; or
(d) the rearranged V domain is a vλ and the C domain is a CK.

5. A cell comprising an antibody heavy chain locus (first locus), wherein the locus comprises (in 5' to 3' direction)
(a) a heavy chain intronic enhancer (Eμ);
(b) a rearranged antibody variable region encoding a rearranged antibody V domain (eg, a VL, V\ or VK, eg, a VH);
(c) an optional switch sequence; and
(d) an antibody heavy chain constant region encoding a heavy chain CHI domain;
wherein the locus is operable to express an antibody chain comprising (in N- to C-terminal direction) said rearranged V domain and said CHI domain.

Optionally, the constant region encodes an antibody Fc (eg, in N- to C-terminal direction: CHI-optional hinge-CH2-CH3).

Optionally, the CH I is a human or mouse CHI, eg, when the cell is a mouse cell.

In an example, the constant region encodes an antibody Fc (eg, in N- to C-terminal direction: CHI-optional hinge-CH2-CH3) there is no further C domain-encoding nucleotide sequence 3' of said constant region.

6. The cell of any preceding Statement, wherein the locus comprises (in 5' to 3' direction)
(a) a promoter operable for promoting transcription of the variable region;
(b) a nucleotide sequence encoding a variable domain signal peptide;
(c) said intronic enhancer;
(d) said rearranged antibody variable region; and
(e) said antibody light chain constant region,
Wherein the locus is operable to express NA transcripts encoding (in N- to C-terminal direction) said signal peptide sequence fused to the amino acid sequence of said variable domain.

Optionally, the promoter and/or the signal peptide-encoding sequence are those that are operable with the variable region (or a V gene segment sequence thereof) in a wild-type cell (eg, a human cell when the V region is a human V region comprised by the human cell), B-cell or hybridoma, such as a B-cell or hybridoma that comprises a sequence identical to said variable region for expressing antigen-specific V domains.

7. The cell of any preceding Statement, wherein the cell is an ES (eg, a 129, C57BL/6, AB2.1, AB2.2, JM8 or F1H4 type ES cell), iPS, hybridoma or B-cell.

8. The cell of any preceding Statement, wherein the rearranged V domain is a kappa or lambda V domain, eg, a rearranged human kappa or lambda V domain.

9. The cell of any preceding Statement, wherein the variable region encodes for a V domain that has a binding specificity for a first predetermined antigen or a first epitope (eg, when paired with another rearranged V domain), wherein the locus is operable to express an antibody chain that comprises a V domain that retains said specificity (eg, when paired with said other V domain).

For example, the variable region encodes for a VL domain that has a binding specificity for a first predetermined antigen or a first epitope (eg, when paired with a rearranged VH domain), wherein the locus is operable to express an antibody light chain that comprises a VL domain that retains said specificity (eg, when paired with said VH domain). For example, the VL and VH are identical to the VL and VH of a known antibody that is capable of specifically binding to a predetermined antigen.

10. The cell of any preceding Statement, wherein the cell comprises a second antibody locus that is operable to express a second antibody chain, wherein the second chain comprises a second rearranged V domain that forms a binding site with the first rearranged V domain, wherein the binding site is capable of specifically binding to a predetermined antigen or a epitope.

For example, the first locus encodes a VL domain and the second locus encodes a VH domain, wherein the VL and VH are capable of forming a VH/VL binding site for said predetermined antigen or epitope.

11. The cell of Statement 10 when dependent from Statement 9, wherein the predetermined antigens are different and said other and second V domains are different; or wherein the epitopes are different and said other and second V domains are different.

For example, the epitopes are different epitopes comprised by the same antigen.

12. The cell of Statement 11, wherein (a) the first domain is a VL (eg, VK or vλ) domain and the second and said other V domains are VH domains; or (b) wherein the first domain is a VH domain and the second and said other V domains are VL (eg, both VK or vλ) domains.

13. The cell of any preceding Statement, wherein the variable region is within 0.5, 0.4, 0.3, 0.2 or 0.1 kb 3' of the enhancer.

Optionally, the variable region is spaced from the intronic enhancer by no more than 0.5, 0.4, 0.3, 0.2 or 0.1 kb.

14. The cell of any preceding Statement, wherein the locus comprises a second enhancer that is 3' of the constant region.

Optionally, the locus (eg, according to Statement 5) is a heavy chain locus, and the second enhancer is a heavy chain 3' enhancer.

Optionally, the locus (eg, according to Statement 1) is a kappa chain locus, and the second enhancer is a kappa chain 3' enhancer.

Optionally, the locus (eg, according to Statement 1) is a lambda chain locus, and the second enhancer is a lambda chain 3' enhancer, eg, a mouse lambda 3-1 enhancer.

15. The cell of any preceding Statement, wherein the cell is a non-human mammal or rodent (eg, a mouse or rat) cell.

16. The cell of any preceding Statement, wherein said constant region is at an endogenous antibody locus of the cell.

Optionally, a further variable region (eg, a mouse variable region or a human variable region) is 5' of the intronic enhancer; for example, the further variable region is inactive for expression of variable domains. Optionally, no variable region (eg, a mouse variable region or a human variable region) is 5' of the intronic enhancer. Optionally, the further variable region comprises a lesion (eg, a J region lesion or is devoid of J gene segments) or a neo (neomycin resistance) marker, thereby inactivating rearrangement in said further variable region.

17. The cell of Statement 16 when dependent from. Statement 1, wherein said endogenous locus is an endogenous kappa chain locus.

18. The cell of Statement 16 when dependent from Statement 5, wherein said endogenous locus is an endogenous heavy chain locus.

19. The cell of any one of Statements 1 to 15, wherein the locus is comprised by a transgene that is comprised by the genome of the cell at a position outside an endogenous antibody locus, (eg, at Rosa 26).

Optionally, the cell genome comprises a plurality of said transgenes.

20. The cell of any preceding Statement, wherein the cell is homozygous for said locus.

Alternatively, the cell is heterozygous for said locus.

21. The cell of any preceding Statement when dependent from Statement 1, wherein the cell genome comprises a second antibody locus, wherein the second locus is an unrearranged antibody heavy chain locus comprising (in 5' to 3' direction)

(a) one or more VH gene segments;

(b) one or more DH gene segments;

(c) one or more JH gene segments; and (d) a heavy chain constant region encoding one or more CH domains;

Wherein the heavy chain locus is operable to express a plurality of heavy chains, optionally comprising a plurality of antigen specificities or affinities, each said heavy chain being capable of pairing with an antibody chain (eg, a kappa or lambda light chain) encoded by the first locus to produce paired chains that comprise an antigen binding site.

Preferably, the VH (eg, the VH, DH and JH) gene segments are human gene segments. Optionally, the CH is a rodent, eg, a mouse or rat, or a human CH (eg, when the cell is a mouse or rat cell).

Optionally, in an alternative the cell of the invention comprises a heavy chain transgene comprising an unrearranged heavy chain variable region (eg, a human V region) operably connected 5' of a heavy chain constant region (eg, a mouse, rat or human constant region) for expressing a plurality of different heavy chains.

In an example, the second locus according to Statement 21 or said heavy chain variable region of the transgene comprises at least 5, 10, 15 or all human VH gene segments of the group consisting of IGHV1-3, IGHV1-8, IGHV1-18, IGHV1-46, IGHV3-7, IGHV3-9, IGHV3-11, IGHV3-15, IGHV3-20, IGHV3-21, IGHV3-23, IGHV3-30, IGHV3-33, IGHV3-48, IGHV3-53, IGHV4-4, IGHV4-31, IGHV4-34, IGHV4-39, IGHV4-59, IGHV4-61, IGHV5-51, IGHV6-1 and IGHV7-4-1.

In an example, the first locus of the invention encodes a light chain, wherein the light chain pairs with or is capable of pairing with at least 5, 10, 15 or all human VH gene segments of the group consisting of IGHV1-3, IGHV1-8, IGHV1-18, IGHV1-46, IGHV3-7, IGHV3-9, IGHV3-11, IGHV3-15, IGHV3-20, IGHV3-21, IGHV3-21, IGHV3-23, IGHV3-30, IGHV3-33, IGHV3-48, IGHV3-53, IGHV4-4, IGHV4-31, IGHV4-34, IGHV4-39, IGHV4-59, IGHV4-61, IGHV5-51, IGHV6-1 and IGHV7-4-1.

In an example, the light chain pairs with or is capable of pairing with human VH gene segments IGHV1-3, IGHV1-8, IGHV1-18, IGHV1-46, IGHV3-7, IGHV3-9, IGHV3-11, IGHV3-15, IGHV3-20, IGHV3-21, IGHV3-23, IGHV3-30, IGHV3-33, IGHV3-48, IGHV3-53, IGHV4-4, IGHV4-31, IGHV4-34, IGHV4-39, IGHV4-59, IGHV4-61, IGHV5-51, IGHV6-1 and IGHV7-4-1 in a vertebrate of the invention.

In an example, the second locus according to Statement 21 or said heavy chain variable region of the transgene comprises at least 5, 10, 15 or all human VH gene segments of the group consisting of IGHV1-3*01, IGHV1-8*01, IGHV1-18*01, IGHV1-46*03, IGHV3-7*01, IGHV3-9*01, IGHV3-11*01, IGHV3-15*01, IGHV3-20*d01, IGHV3-21*03, IGHV3-23*04, IGHV3-30*18, IGHV3-33*01, IGHV3-48*02, IGHV3-53*01, IGHV4-4*02, IGHV4-31*03, IGHV4-34*01, IGHV4-39*01, IGHV4-59*01, IGHV4-61*01, IGHV5-51*01, IGHV6-1*01 and IGHV7-4-1*01.

In an example, the first locus of the invention encodes a light chain, wherein the light chain pairs with or is capable of pairing with at least 5, 10, 15 or all human VH gene segments of the group consisting of IGHV1-3*01, IGHV1-8*01, IGHV1-18*01, IGHV1-46*03, IGHV3-7*01, IGHV3-9*01, IGHV3-11*01, IGHV3-15*01, IGHV3-20*d01, IGHV3-21*03, IGHV3-23*04, IGHV3-30*18, IGHV3-33*01, IGHV3-48*02, IGHV3-53*01, IGHV4-

4*02, IGHV4-31*03, IGHV4-34*01, IGHV4-39*01, IGHV4-59*01, IGHV4-61*01, IGHV5-51*01, IGHV6-1*01 and IGHV7-4-1*01.

In an example, the light chain pairs with or is capable of pairing with human VH gene segments IGHV1-3*01, IGHV1-8*01, IGHV1-18*01, IGHV1-46*03, IGHV3-7*01, IGHV3-9*01, IGHV3-11*01, IGHV3-15*01, IGHV3-20*d01, IGHV3-21*03, IGHV3-23*04, IGHV3-30*18, IGHV3-33*01, IGHV3-48*02, IGHV3-53*01, IGHV4-4*02, IGHV4-31*03, IGHV4-34*01, IGHV4-39*01, IGHV4-59*01, IGHV4-61*01, IGHV5-51*01, IGHV6-1*01 and IGHV7-4-1*01 in a vertebrate of the invention.

Optionally, the cell is a mouse or rat ES cell that is capable of developing into a mouse or rat respectively, wherein the mouse or rat is capable of expressing a plurality of heavy chains, optionally comprising a plurality of antigen specificities or affinities, each said heavy chain being capable of pairing with an antibody chain (eg, a kappa or lambda light chain) encoded by the first locus to produce paired chains that comprise an antigen binding site.

The cell of any one of Statements 1 to 20 when dependent from Statement 5, wherein the cell comprises one or more further antibody loci, each further locus being capable of expressing a light chain, each said light chain being capable of pairing with an antibody chain (eg, a VH-Fc) encoded by the first locus to produce paired chains that comprise an antigen binding site.

Optionally, the cell is a mouse or rat (or other non-human vertebrate) ES cell that is capable of developing into a mouse or rat (or other vertebrate) respectively, wherein the mouse or rat (or vertebrate) is capable of expressing one or more light chains, optionally comprising a plurality of antigen specificities or affinities, each said light chain being capable of pairing with an antibody chain (eg, a VH-Fc) encoded by the first locus to produce paired chains that comprise an antigen binding site. This may be useful in the practice of the following method of producing a bi-specific antibody:—

A method comprising (i) Providing a non-human vertebrate (eg, a mouse or rat) according to the immediately preceding paragraph, wherein the variable region of the first locus encodes a VH domain of an antibody that specifically binds to a first predetermined antigen;

(ii) immunising the vertebrate with a second predetermined antigen, wherein the vertebrate expresses a plurality of said light chains, wherein VL domains of the chains pair with copies of said VH to form VH/VL antigen binding sites which specifically bind to the second antigen;

(iii) Isolating one or more VH/VL pairs that bind to the first and second antigens; or obtaining one or more B-cells or hybridomas that express said VH/VL pairs that bind the antigens; or obtaining a nucleotide sequence encoding a VL of a said pair and/or a nucleotide sequence of a VH of a said pair;

(iv) Optionally, inserting the nucleotide sequences into one or more expression vectors or one or more host cells for expressing bispecific antibodies comprising VH/VL paired binding sites, where each binding site is capable of specifically binding to the first and second antigens; and (v) Optionally expressing and isolating said bispecific antibodies.

In an example, the vertebrate of step (i) is a chimaera as described herein, wherein the chimaera expresses said one or more light chains.

There is also provided:—A method of producing a bispecific antibody, comprising expressing from a host cell line a plurality of antibodies, wherein the host cell line is obtained by steps (i) to (iv) or is cultured from cells so obtained.

There is also provided:—A method of producing a bispecific antibody, comprising expressing from a host cell line a plurality of antibodies, wherein each host cell genome comprises an expressible nucleotide sequence encoding a heavy chain variable domain of the bispecific antibody, wherein the variable domain is capable of specifically binding a first antigen, the nucleotide sequence being identical (or at least 80, 85, 90 or 95% identical) to a nucleotide sequence of a B-cell of a vertebrate of the invention wherein the vertebrate has been immunised with the first antigen. In an example, each host cell genome comprises a nucleotide sequence encoding light chain variable domain that is identical (or at least 80, 85, 90 or 95% identical) to a nucleotide sequence of the B-cell, wherein the heavy and light chains domains form a paired VH/VL first antigen binding site. Optionally, the method comprises isolating a plurality of such bispecific antibodies, and optionally further formulating the antibodies with a carrier, diluent or excipient to produce a composition (such as a pharmaceutical composition). The invention also relates to such a plurality of antibodies or composition obtained or obtainable by this method or any other method of the invention.

In an alternative, instead of the first locus encoding a VH, the first locus instead encodes a VL or light chain and the vertebrate is capable of expressing one or more heavy chains, optionally comprising a plurality of antigen specificities or affinities, each said heavy chain being capable of pairing with an antibody chain (eg, a light) encoded by the first locus to produce paired chains that comprise an antigen binding site. Such a vertebrate may be used mutatis mutandis in a method comprising steps (i) etc, wherein the VL is a VL of an antibody that specifically binds to the first antigen.

In this way, chain shuffling can be performed in vivo according to the invention, wherein the starting point can be a fixed, predetermined VH or VL of an antibody of known antigen binding specificity. The end result is an antibody, wherein VH/VL binding sites are themselves bispecific for first and second antigens (or alternatively first and second epitopes of the same antigen).

23. The cell of any preceding Statement, wherein each variable region or gene segment is human, and optionally said constant region is human.

Optionally, each gene segment is a human germline gene segment.

24. The cell of any preceding Statement, wherein the cell is a mouse cell and each constant region is a mouse, rat or human constant region.

For example, each constant region is a human constant region.

25. The cell of any preceding Statement, wherein each said enhancer is an endogenous enhancer of the cell.

In an example, the intronic enhancer is of the same species or strain as the cell, comprises the endogenous enhancer sequence of the cell, or comprises an insert into the cell genome (eg, an insert that comprises an enhancer sequence that is identical to the endogenous enhancer sequence).

26. The cell of any preceding Statement, wherein the cell is a mouse cell and each said enhancer is a mouse enhancer.

For example, the enhancer is a 129 hybrid or C57BL6 hybrid strain enhancer (and optionally the cell is a 129 hybrid or C57BL6 hybrid strain respectively). For example, the enhancer is a 129 enhancer and the cell is a FIH4 or AB2.1 cell.

27. The cell of any preceding Statement, wherein
(a) the cell is a mouse cell, the variable region is a human variable region, the intronic enhancer is a mouse intronic enhancer (eg, sequence identical to an endogenous mouse intronic enhancer) at an endogenous antibody locus (eg, a kappa locus) of the cell and said constant region is a mouse, rat or human constant region (eg, an endogenous mouse constant region of the cell); or
(b) the cell is a rat cell, the variable region is a human variable region, the intronic enhancer is a rat intronic enhancer (eg, sequence identical to an endogenous rat intronic enhancer) at an endogenous antibody locus (eg, a kappa locus) of the cell and said constant region is a mouse, rat or human constant region (eg, an endogenous rat constant region of the cell).

For example, the cell is a mouse cell, the variable region is a human variable region, the intronic enhancer comprises a sequence identical to an endogenous mouse intronic enhancer and is at an endogenous kappa locus of the cell and said constant region is a human constant region.

For example, the cell is a mouse F1H4 cell, the variable region is a human variable region, the intronic enhancer comprises a sequence identical to a mouse 129 Eίκ intronic enhancer and is at an endogenous kappa locus of the cell and said constant region is a human constant region. For example, the cell is a mouse AB2.1 cell, the variable region is a human variable region, the intronic enhancer comprises a sequence identical to a mouse 129 Eίκ intronic enhancer and is at an endogenous kappa locus of the cell and said constant region is a human constant region.

For example, the cell is a mouse F1H4 cell, the variable region is a human lambda variable region, the intronic enhancer comprises a sequence identical to a mouse 129 Eίκ intronic enhancer and is at an endogenous kappa locus of the cell and said constant region is a human lambda constant region. For example, the cell is a mouse AB2.1 cell, the variable region is a human lambda variable region, the intronic enhancer comprises a sequence identical to a mouse 129 Eίκ intronic enhancer and is at an endogenous kappa locus of the cell and said constant region is a human lambda constant region.

For example, the cell is a mouse F1H4 cell, the variable region is a human kappa variable region, the intronic enhancer comprises a sequence identical to a mouse 129 Eίκ intronic enhancer and is at an endogenous kappa locus of the cell and said constant region is a human kappa constant region. For example, the cell is a mouse AB2.1 cell, the variable region is a human kappa variable region, the intronic enhancer comprises a sequence identical to a mouse 129 Eίκ intronic enhancer and is at an endogenous kappa locus of the cell and said constant region is a human kappa constant region 28. The cell of any preceding Statement, wherein the rearranged variable region is a rearrangement of
(a) human IGLV3-21 and IGLJ3 (eg, IGLV3-21*01 and IGLJ3*02) and optionally operably connected to human germline IGLV3-21 (eg, IGLV3-21*01) promoter and/or signal peptide-encoding nucleotide sequence;

(b) human IGK1-39 and IGKJ1 or 5 and optionally operably connected to human germline IGKV1-39 promoter and/or signal peptide-encoding nucleotide sequence;
(c) human IGK3-20 and IGKJ1 or 5 and optionally operably connected to human germline IGKV3-20 promoter and/or signal peptide-encoding nucleotide sequence;
(d) a human VpreB and j\5 and optionally operably connected to human germline VpreB promoter and/or signal peptide-encoding nucleotide sequence.

29. A transgenic non-human vertebrate comprising a plurality of cells according to any preceding Statement.

For example, the vertebrate is an embryo comprising at least 20, 30, 40 or 50% of its cells as cells of the invention. For example, the vertebrate is rodent (eg, mouse or rat) child comprising at least 20, 30, 40 or 50% of its cells as cells of the invention, eg, as indicated by percentage of coat colour (eg, total area of albino versus aguti coat colour).

30. The vertebrate of Statement 29, wherein the germline of said vertebrate comprises a first locus (and optionally the second locus) as defined in any one of Statements 1 to 28.

For example, the invention provides a transgenic non-human vertebrate chimaera comprising a plurality of cells according to any preceding Statement. Optionally, the germline of said chimaera (or the chimaera of Statement 31) does not comprise a first locus (and optionally also not the second locus) as defined in any one of Statements 1 to 28. Thus, with the present invention the time and effort required to generate vertebrates that show germline transmission of the locus is avoided, as chimaeras can be simply generated and used without germline transmission, which is a benefit over prior art configurations.

31. The vertebrate of Statement 29, wherein the vertebrate is a chimaera of said cells and a plurality of other cells that do not comprise the first locus (eg, wherein the other cells comprise wild-type antibody loci), wherein the germline of the vertebrate does not comprise a first locus.

Optionally, said other cells comprise a RAG knock-out. This is useful as productive mature B-cells in the chimaera will result only from cells of the invention, thereby removing unwanted background. Here, productive refers to B-cells that can express antibodies that contribute to the antibody repertoire of the vertebrate.

In an example, the cells of the invention are F1H4, AB2.1, AB2.2, 129 or C57BL6 strain cells and said other cells are F1H4, AB2.1, AB2.2, 129 or C57BL6 strain cells (eg, progeny cells of a wild-type blastocyst or pre-morula embryo; or a RAG knock-out blastocyst or pre-morula embryo).

32. The vertebrate of any one of Statements 29 to 31, comprising a first plurality of cells and a second plurality of cells, wherein the cells of the first plurality comprise the same first identical antibody locus, and the cells of the second plurality comprise the same additional identical antibody locus, wherein each said antibody locus is according to the first locus of any one of Statements 1 to 28, wherein the vertebrate is capable of expressing a first plurality of antibody chains from said first identical locus and a second plurality of antibody chains from said additional locus, and wherein the antibody locus of the first cells is different from the antibody locus of the second cells.

33. The vertebrate of Statement 32, wherein the vertebrate comprises a third plurality of cells, wherein the cells of the third plurality comprise the same further antibody locus, wherein the further locus is according to any one of Statements 1 to 28 and is different from said antibody loci of the first and second cells, wherein the vertebrate is capable of expressing a third plurality of antibody chains from the further locus.

34. The vertebrate of Statement 32 or 33, wherein the vertebrate is a chimaera of said cells and a plurality of other cells that do not comprise a first locus according to any one of Statements 1 to 28 or said additional or further loci (eg, wherein the other cells comprise wild-type antibody loci).

35. A transgenic non-human vertebrate whose antibody light chain repertoire is at least 95, 96, 97, 98 or 99% pure (or is 100% pure) for a single rearranged VL domain species.

This, therefore, means that all VL expressed by the vertebrate are said VL domain species, or only less than 5% of VL are of another species.

In an example, a vertebrate herein is naive. In another example, the vertebrate is antigen immunised (eg, human antigen immunised).

Purity may, for example, be determined from a blood sample or VL-encoding nucleotide sequence sample of the vertebrate, using standard NGS and optionally with PC amplification of VL-encoding nucleotide sequences comprised by the sample. Optionally, B-cells or hybridomas from or produced from the sample are sorted into individual wells of one or more plates and then subjected to optional PCR of the VL-encoding nucleotide sequence thereof, followed by NGS to determine the sequence of the nucleotide sequence in each well. The sequences are analysed to determine the proportion that encode said single rearranged VL domain species.

In an example, the VL species is a human VK. In an example, the VL species is a human vλ.

36. The vertebrate of Statement 35, wherein the repertoire is at least 99% pure for a single rearranged VL domain species.

37. The vertebrate of Statement 35 or 36, wherein the remainder of the light chains of the light chain repertoire comprise mutants of said VL domain species.

38. A transgenic non-human vertebrate whose antibody light chain repertoire comprises VL domains derived from the recombination of a first VL gene segment and a first J L gene segment, wherein at least 95% of all VL domains derived from said recombination comprise the same VL amino acid sequence.

In another embodiment, the invention provides a transgenic non-human vertebrate wherein at least 95, 96, 97 98 or 99% (or 1.00%) of all VL domains of the antibody light chain repertoire of the vertebrate are encoded by the same light chain variable region sequence comprised by the genome of the vertebrate.

In another embodiment, the invention provides a transgenic non-human vertebrate wherein at least 95, 96, 97 98 or 99% (or 100%) of all VL domains of the human VL repertoire of the vertebrate are encoded by the same light chain variable region sequence comprised by the genome of the vertebrate.

39. The vertebrate of Statement 38, wherein at least 99% of all VL domains derived from said recombination comprise the same VL amino acid sequence.

40. A plurality of spleen, bone marrow, B-cells or blood cells of a vertebrate according to any one of Statements 29 to 39 or said other embodiments of Statement 38 comprising a plurality of first loci according to any one of Statements 1 to 28.

41. A population of spleen, bone marrow, B-cells, hybridomas, CHO cells, HEK cells, MEF cells, COS cells, HeLa cells or blood cells, wherein each cell is according to Statement 1 or any one of Statements 2 to 28 when dependent from Statement 1; and optionally, wherein the cells express at least 10 different antibody species wherein (a) at least 95, 96, 97, 98 or 99% (or 100%) of the antibodies share the same light chain VL domain and the population comprises at least 10 different VII domain species; or (b) the antibodies comprise VL domains derived from the recombination of a first VL gene segment and a first JL gene segment (eg, human germline VK and JK gene segments or human germline vλ and i\ gene segments), wherein at least 95% of all said VL domains derived from said recombination comprise the same VL amino acid sequence and the population comprises at least 10 different VH domain species.

Optionally, the cells are HEK293 cells, eg, HEK293T or S cells, COS-1 or COS-7 cells.

Optionally, the cells express at least 100, 1000, 10000, 100000, 1000000, 10000000, 100000000, or 1000000000 different antibody species. Optionally, the population comprises at least 100, 1000, 10000, 100000, 1000000, 10000000, 100000000, or 10000000000000 different VH domain species.

42. A polyclonal antibody population, wherein at least 95, 96, 97, 98 or 99% (or 100%) of the antibodies comprised by the population share the same light chain VL domain and the population comprises at least 10 different VH domain species.

Optionally, the population comprises at least 100, 1000, 10000, 100000, 1000000, 100000000000, 100000000, or 1000000000 different VH domain species.

In an example, an antibody population herein is contained in a sterile or medical container, in a test tube, petri dish or a flask. Optionally the population is mixed with B-cells, wherein the B-cells comprise a locus according to the invention.

43. A polyclonal antibody population, comprising VL domains derived from the recombination of a first VL gene segment and a first J L gene segment (eg, human germline VK and JK gene segments or human germline vλ and i\ gene segments), wherein at least 95, 96, 97, 98 or 99% (or 100%) of all said VL domains derived from said recombination comprise the same VL amino acid sequence and the population comprises at least 10 different VH domain species.

Optionally, the population comprises at least 100, 1000, 10000, 100000, 1000000, 10000000, 100000000, or 1000000000 different VH domain species.

A method of identifying or obtaining an antibody, an antibody variable domain, a nucleotide sequence (eg, DNA or NA sequence) encoding an antibody or an antibody variable domain, or an expression vector or host cell that is capable of expressing the antibody or domain, wherein the antibody or domain is capable of specifically binding to a target antigen, the method comprising (a) contacting the cell population of Statement 41, or the antibody population of 42 or 43 with said antigen (eg, immobilised on a solid support);

(b) binding antibodies expressed or comprised by said population to said antigen; and (c) isolating or identifying one or more antibodies that bind to the antigen, or isolating or identifying a VH and/or a VL domain of a said one or more antibody; or identifying a nucleotide sequence encoding a said VH or VL; and (d) optionally (i) correlating a said identified antibody or domain with a nucleotide sequence (eg, DNA, cDNA, RNA or mRNA sequence) encoding therefor, thereby identifying said sequence;

(ii) amplifying said sequence (eg, using PCR) and inserting the sequence into an expression vector or a host cell genome for expression of the encoded antibody or domain; and (iii) optionally expressing and isolating said antibody or domain (eg, wherein the domain is comprised by an antibody chain), wherein steps (i) and (ii) can be carried out in any order. may be used, for example, in said correlating.

The method of Statement 44, comprising using the method to amplify the VH and VL nucleotide sequences encoding the VH and VL domains of the identified antibody and further comprising inserting the VII and VL nucleotide sequences into the vector or cell for co-expression of the VH and VL to produce paired VH/VL binding sites that are capable of binding to the antigen, and expressing (and optionally isolating) the binding sites (eg, comprised by antibodies encoded by the vector or cell).

The method of Statement 45, wherein the method comprises expressing the VH and VL in the presence of a further species of VH domain, wherein the VL and the further VH form further paired VH/VL sites that are capable of binding to a further antigen, wherein the further antigen and the antigen recited in Statement 45 are different, the method comprising co-expressing (and optionally isolating) the binding sites (eg, comprised by bi-specific antibodies encoded by the vector or cell, wherein the bi-specific antibodies comprise a respective binding site for each said antigen).

The method of Statement 46, wherein the bi-specific antibodies are 4-chain antibodies comprising a first heavy chain-light chain pair and a second heavy chain-light chain pair, wherein (a) the light chain in the first and second pairs comprises said VL domain, (b) the heavy chain of the first pair comprises the VH domain recited in Statement 45, wherein the VH domain forms a VH/VL binding site with said VL domain and wherein the binding site is capable of specifically binding to said antigen recited in Statement 45;

(c) the heavy chain of the second pair comprises said further VH domain that forms a VH/VL binding site with said VL domain and wherein the binding site is capable of specifically binding to said further antigen recited in Statement 46.

The method of Statement 47, wherein each 4-chain antibody comprises mutated heavy chain constant regions to promote pairing of the heavy chains of the first and second heavy-light pairs; optionally wherein the mutations are knob-in-hole mutations or charge pair mutations.

example, each constant region is encoded by a heavy chain constant region sequence comprised n expression vector.

Advantageously, in an example the heavy chains of the first pair have a first pi and the heavy chains of the second pair have a second pi, wherein the pi values are different, for example differ by 0.5-1.5 pi units, eg, differ by 0.5-1 pi units. This is useful for separating the first chains from the second chains during in vitro purification of chains, as is useful during antibody manufacture and scale-up. For example, each pi is in the range of 5 to 6.5.

49. A plurality of B-cells, hybridomas, CHO cells, HEK cells, MEF cells, COS cells, HeLa cells that expresses the polyclonal antibody population of Statement 42 or 43.

Optionally, the cells are HEK293 cells, eg, HEK293T or S cells, COS-1 or COS-7 cells.

50. The method of any one of Statements 44 to 48, wherein the method comprises obtaining VL and/or VH-encoding nucleotide sequences from the cells of Statement 41 or 47, and in step (d) (i) using the nucleotide sequences to correlate one or more thereof with one or more VH and/or VL domains of said antibodies that bind the antigen.

51. A method obtaining a nucleotide sequence encoding an antibody or an antibody variable domain, wherein the antibody or domain is capable of specifically binding to a target antigen, the method comprising (a) obtaining VL and/or VH-encoding nucleotide sequences from the cells of Statement 41 or 47;

(b) amplifying said sequence (eg, using PC); and (c) optionally inserting the sequence into an expression vector or a host cell genome for expression of the encoded antibody or domain.

In an example, an expression vector herein is a CHO cell expression vector for use in a CHO host cell. In an example, an expression vector herein is a HEK293 cell expression vector for use in a HEK293 host cell.

52. A method obtaining an antibody-producing cell line for the production of antibodies that specifically bind to an antigen, the method comprising inserting VH and VL-encoding nucleotide sequences into the genome of a host cell (eg, a CHO, HEK, MEF, COS or HeLa cell), wherein (a) each VII sequence is operably inserted 5' of an antibody heavy chain constant region (eg, a human constant region) for expression of heavy chains by the cell comprising VH and C domains;

(b) each VL sequence is operably inserted 5' of an antibody light chain constant region (eg, a human constant region) for expression of light chains by the cell comprising VL and C domains;

(c) wherein the expressed heavy chains are capable of pairing with the light chains to produce heavy-light chain pairs, each pair comprising a VH/VL binding site that is capable of binding to an antigen; and (d) wherein VH and VL-encoding nucleotide sequences are the sequences of VH and VL-encoding nucleotide sequences of one or more cells of Statement 41 or 47.

Optionally, the host cell is a HEK293 cell, eg, HEK293T or S cell, COS-1 or COS-7 cell.

53. The method of Statement 52, comprising inserting first and second VH-encoding nucleotide sequences into the cell genome, wherein (a) the first VH (when expressed as part of first heavy chains) is capable of pairing with the VL (when expressed as part of light chains) to form a first VH/VL binding site that is capable of specifically binding to a first antigen;

(b) the second VH (when expressed as part of second heavy chains) is capable of pairing with the VL (when expressed as part of light chains) to form a second VH/VL binding site that is capable of specifically binding to a second antigen; and (c) the first and second antigens are different;

wherein the first and second heavy chains and the light chains are capable of pairing to produce bi-specific 4-chain antibodies comprising a first heavy chain-light chain pair and a second heavy chain-light chain pair, wherein (d) the heavy chain of the first heavy chain-light chain pair comprises the first VH; and (e) the heavy chain of the second heavy chain-light chain pair comprises the second VH domain.

54. A method of producing bi-specific 4-chain antibodies wherein the bi-specific antibodies comprise a respective binding site for first and second antigens, wherein the antigens are different, each antibody comprising a first heavy chain-light chain pair and a second heavy chain-light chain pair, wherein (a) the heavy chain of the first heavy chain-light chain pair comprises a first VH, wherein the first VH (when expressed as part of first heavy chains) is capable of pairing with a VL (when expressed as part of light chains) to form a first VH/VL binding site that is capable of specifically binding to the first antigen; and (b) the heavy chain of the second heavy chain-light chain pair comprises a second VH, wherein the second VH (when expressed as part of second heavy chains) is capable of pairing with said VL (when expressed as part of light chains) to form a second VH/VL binding site that is capable of specifically binding to the second antigen;

the method comprising (c) producing a first cell line that is capable of expressing the first heavy chains by (i)

inserting into a first cell genome a nucleotide sequence encoding said first VH, wherein the VH sequence is operably inserted 5' of an antibody heavy chain constant region (eg, a human constant region) for expression of first heavy chains comprising first VH and C domains; and (ii) culturing the cell to produce a first cell line that expresses first heavy chains;

(d) producing a second cell line that is capable of expressing the second heavy chains by (i) inserting into a second cell genome a nucleotide sequence encoding said second VH, wherein the VH sequence is operably inserted 5' of an antibody heavy chain constant region (eg, a human constant region) for expression of second heavy chains comprising second VH and C domains; and (ii) culturing the cell to produce a second cell line that expresses second heavy chains;

(e) expressing first heavy chains from the first cell line and second heavy chains from the second cell line and mixing together first heavy chains comprising said first VI, second heavy chains comprising said second VII and light chains comprising said VL, whereby (iii) first heavy chains pair with light chains to produce said first heavy chain-light chain pairs, (iv) second heavy chains pair with light chains to produce said second heavy chain-light chain pairs; and (v) the first heavy chain-light chain pairs pair with the second heavy chain-light chain pairs, thereby producing said bi-specific antibodies wherein VH and/or VL-encoding nucleotide sequences are the sequences of VH and/or VL-encoding nucleotide sequences of one or more cells of Statement 41 or 47.

Optionally, the first heavy chains and second heavy chains have first and second different pi values as described herein, wherein the method further comprises co-expressing the chains to produce a mixture and using pH change of the mixture to separate (eg, elute from a matrix) first chains from second chains, thereby producing a population of first chains that is separate from a population of second chains; and combining the first and second chains with the light chains to produce the bispecific antibodies.

The invention further provides an antibody (eg, a bispecific antibody) obtained or obtainable by a method of the invention. Optionally, the antibody is for treating or preventing a disease or condition in a human or animal subject.

55. The method of Statement 54, comprising (a) producing a third cell line that is capable of expressing the light chains by (i) inserting into a third cell genome a nucleotide sequence encoding said VL, wherein the VL sequence is operably inserted 5' of an antibody light chain constant region (eg, a human constant region) for expression of light chains comprising the VL and C domains; and (ii) culturing the cell to produce a third cell line that expresses the light chains;

(b) expressing the light chains from the third cell line, wherein the light chains are the light chains of step (e) of Statement 54.

56. The method of Statement 54, comprising (a) inserting into the genome of the first and/or second cell or cell lines a nucleotide sequence encoding said VL, wherein the VL sequence is operably inserted 5' of an antibody light chain constant region (eg, a human constant region) for expression of light chains comprising the VL and C domains; and (b) expressing the light chains from the cell lines comprising the VH sequence, wherein the light chains are the light chains of step (e) of Statement 54.

57. The method of Statement 54, 55 or 56, wherein said mixing of chains is carried out by co-culturing the cell lines.

58. The method of Statement 54, 55 or 56, wherein said mixing of chains is carried out by isolating chains expressed by the cell lines and mixing the isolated chains together (eg, in a container that does not comprise said cells).

Said isolating can be performed, for example, using differential pi of chains as described herein.

59. A method of producing bi-specific 4-chain antibodies wherein the bi-specific antibodies comprise a respective binding site for first and second antigens, wherein the antigens are different, each antibody comprising a first heavy chain-light chain pair and a second heavy chain-light chain, pair, wherein (a) the heavy chain of the first heavy chain-light chain pair comprises a first VH, wherein the first VH (when expressed as part of first heavy chains) is capable of pairing with a VL (when expressed as part of light chains) to form a first VH/VL binding site that is capable of specifically binding to the first antigen; and (b) the heavy chain of the second heavy chain-light chain pair comprises a second VH, wherein the second VH (when expressed as part of second heavy chains) is capable of pairing with said VL (when expressed as part of light chains) to form a second VH/VL binding site that is capable of specifically binding to the second antigen;

the method comprising (c) mixing together first heavy chains comprising said first VH, second heavy chains comprising said second VH and light chains comprising said VL, whereby (i) first heavy chains pair with light chains to produce said first heavy chain-light chain pairs, (ii) second heavy chains pair with light chains to produce said second heavy chain-light chain pairs; and (iii) the first heavy chain-light chain pairs pair with the second heavy chain-light chain pairs, thereby producing said bi-specific antibodies wherein VH and/or VL are encoded by VH and/or VL-encoding nucleotide sequences, wherein the nucleotide sequences are the sequences of VH and/or VL-encoding nucleotide sequences of one or more cells of Statement 41 or 47.

60. The method of any one of Statements 54 to 59, wherein each 4-chain antibody comprises
mutated heavy chain constant regions to promote pairing of the heavy chains of the first and second heavy-light pairs; optionally wherein the mutations are knob-in-hole mutations or charge pair mutations.

For example, expression vectors can be provided into which a VH-encoding sequence is inserted 5' in operably connection with a mutated human heavy chain constant region-encoding nucleotide sequence, wherein the mutation is for knob-in-hole pairing with another heavy chain or for charge pairing with another heavy chain. Thus, the VH of the heavy chain of the first heavy-light pair can be inserted into such a vector 5' of a first mutated heavy chain constant region, and the VII of the heavy chain of the second heavy-light pair can be inserted into such a vector (the same or a different vector) 5' or a second mutated heavy chain constant region, wherein the first and second heavy chains are expressible from the vector(s) and can pair using the knob-in-hole or charge pair mutations. Alternatively, the VH-encoding sequences are inserted 5' of respective constant regions in the genome of the same or different host cells for expression of said heavy chains.

61. A method of producing a pharmaceutical composition for treating or preventing a disease or condition (eg, a cancer or autoimmune disease) in a human or non-human animal subject, the method comprising
(a) expressing an antibody from a cell line produced by the method of Statement 52 or 53; and
(b) mixing the antibody with a diluent or excipient;
(c) optionally wherein the antibody is identical to, or comprises variable domains identical to, an antibody obtained by the method of any one of Statements 54 to 60.
62. A method of producing a pharmaceutical composition for treating or preventing a disease or condition (eg, a cancer or autoimmune disease) in a human or non-human animal subject, the method comprising mixing a bi-specific antibody with a diluent or excipient, wherein the antibody is identical to, or comprises variable domains identical to, an antibody obtained by the method of any one of Statements 54 to 60.
63. A method of producing a cell of any one of Statements 1 to 28 or vertebrate of any one of Statements 29 to 39, the method comprising
(a) obtaining a nucleic acid (eg, DNA or cDNA) comprising a rearranged antibody variable region encoding a rearranged antibody V domain; and
(b) inserting the variable region or a copy thereof into the genome of a cell, whereby the variable region is comprised by an antibody locus in said genome, wherein the locus comprises (in 5' to 3' direction)
(c) an antibody locus intronic enhancer;
(d) said rearranged antibody variable region; and (e) an antibody constant region encoding an antibody C domain;
wherein the locus is operable to express an antibody chain comprising (in N- to C-terminal direction) said rearranged V domain and said C domain; and
(f) optionally, wherein the cell is a non-human vertebrate ES cell or an iPS cell, the method further comprising generating the non-human vertebrate of any one of Statements 29 to 39 from the cell.

Optionally, the cell is a pluripotent, ES or iPS cell and the cell is not capable of generating a human or a human embryo. For example, the cell is not a human ES or iPS or pluripotent stem cell.

Optionally, the cell is a non-human vertebrate (eg, rodent, mouse or rat) cell, eg, ES or iPS cell.

Standard techniques will be known by, and readily available to, the skilled addressee for producing transgenic non-human vertebrates (eg, mice and rats) using the ES or iPS cells of the invention. For example, one or more ES cells of the invention can be introduced into a recipient blastocyst or pre-morula embryo before implantation into a female non-human vertebrate (eg, a pseudopregnant mouse or rat when the ES and blastocyst/pre-morula embryo are mouse or rat respectively).

Optionally, said other cells, blastocyst or pre-morula embryo comprise a RAG knock-out (eg, RAG-1 and/or RAG-2 knock-out). This is useful to ensure that all antibody chains, such as chains produced by cells and loci of the invention, are contributed 100% in the non-human vertebrate by the loci of the invention and not the blastocyst or pre-morula embryo cells. Additionally or alternatively, endogenous IgH expression is knocked-out or inactivated, wherein the non-human vertebrate of the invention is capable of expressing antibody heavy chains comprising human variable domains and human or non-human vertebrate constant domains (eg, from a transgenic IgH locus comprised by cells of the vertebrate).

Optionally, the nucleic acid of step (a) comprises (in 5' to 3' direction) said rearranged antibody variable region and a constant region encoding one or more antibody C domains (eg, a CK, CX or heavy chain Fe). Optionally, the nucleic acid further comprises (5' of the variable region) a promoter operable for promoting transcription of the variable region, and a nucleotide sequence encoding a variable domain signal peptide, wherein the nucleic acid encodes a signal peptide-V domain-C domain.

Optionally, the locus is an antibody light chain locus (first locus), wherein the locus comprises (in 5' to 3' direction)
(g) A light chain intronic enhancer;
(h) A rearranged antibody variable region encoding a rearranged antibody V domain; and
(i) An antibody light chain constant region encoding a light chain C domain;
wherein the locus is operable in the cell to express an antibody chain comprising (in N- to C-terminal direction) said rearranged V domain and said C domain.

Optionally, the locus is an antibody light chain locus (first locus), wherein the locus comprises (in 5' to 3' direction) a light chain intronic enhancer and a nucleotide sequence encoding a rearranged light chain, wherein the locus is operable in the cell to express the light chain.

Optionally, the cell is a rodent (eg, a mouse or rata cell) and the locus is an antibody kappa light chain locus (first locus), wherein the locus comprises (in 5' to 3' direction) a mouse or rat Eκ intronic enhancer and a nucleotide sequence encoding a rearranged human light chain, wherein the locus is operable in the cell to express the light chain.

In an example of any cell, vertebrate, population, composition or method of the invention, the V domain is a VK (eg, human VK) and the C domain is a CK (eg, a human CK). In an example, the V domain is a vλ (eg, human vλ) and the C domain is a CX (eg, a human CX). For example, the nucleic acid encodes a rearranged light chain of an antibody (eg, wherein the antibody specifically binds to a predetermined antigen or epitope).

64. The method of Statement 63, wherein the variable domain is a VL (eg, a human vλ or VK) and the C domain is CL (eg, a human CX or CK).

For example, the variable domain is a human vλ and the C domain is a human CX. For example, the variable domain is a human VK and the C domain is a human CK.

65. The method of Statement 63 or 64, wherein said inserting is carried out using homologous recombination or site-specific recombination (eg, using lox sites) with chromosomal DNA of the cell.

66. The method of any one of Statements 63 to 65, comprising obtaining a transgene comprising (in 5' to 3' direction)

(a) said intronic enhancer (eg, an Eιĸ, such as a mouse or rat Eιĸ);

(b) said rearranged antibody variable region (eg, a human VL-encoding variable region); and (c) said antibody constant region (eg, a human CL-encoding region); and Inserting said transgene into the genome of the cell, whereby said antibody locus is comprised by the cell.

For example, the insertion is at or adjacent the osa26 locus of the cell, or randomly made into the genome.

67. The method of any one of Statements 63 to 65, comprising inserting said variable region between (a) the intronic enhancer and the CL of a light chain locus of the cell genome; or (b) the intronic enhancer (Eμ) and the Cμ of a heavy chain locus of the cell genome.

In any insertion herein, nucleotide sequence of the recipient nucleic acid (eg, cell chromosomal DNA) may be deleted simultaneously or sequentially with the deletion. Alternatively, insertion is without deletion of recipient nucleic acid sequence.

68. The method of any one of Statements 63 to 67, wherein the variable region encodes a V domain (eg, a VL domain) of an antibody that specifically binds to a predetermined antigen.

69. The method of Statement 68, wherein the step of obtaining the nucleic acid comprising the rearranged antibody variable region as recited in Statement 63 comprises (a) obtaining a further cell (eg, a hybridoma or B-cell) that expresses said antibody recited in Statement 68;

(b) obtaining or copying (eg, using PCR)

i. a DNA (eg, a chromosomal DNA or a cDNA) sequence of the further cell that comprises a rearranged variable region sequence encoding the V domain; or ii. a RNA sequence (eg, a mRNA sequence) of the further cell that comprises a rearranged variable region sequence encoding the V domain, and creating a DNA copy of said RNA sequence;

thereby obtaining said nucleic acid.

In an example, RNA may be used to produce a cDNA copy thereof, the cDNA being used in the method of the invention.

70. The method of any one of Statement 63 to 69, comprising culturing the resultant cell to produce a plurality of cells, wherein each cell is according to any one of Statements 1 to 28.

Optionally, said plurality comprise at least 100, $10^3$, $10^4$, $10^s$, $10^s$, $10^7$, $10^s$, $10^9$, $10^{10}$, $10^{11}$ or $10^{12}$ cells, wherein each cell is according to the invention (optionally wherein each cell is identical to the other cells or the cells comprise the same first locus of the invention).

71. A non-human vertebrate (eg, rodent, rat or mouse) blastocyst or pre-morula embryo implanted with an ES or iPS cell according to any one of Statements 1 to 28 or obtained according to the method of any one of Statements 63 to 70.

Optionally, said blastocyst or pre-morula embryo comprises a RAG knock-out (eg, RAG-1 and/or RAG-2 knock-out). This is useful to ensure that all antibody chains in non-human vertebrates grown from the blastocyst or pre-morula embryo are contributed 100% in the non-human vertebrate by the loci if the invention and not the blastocyst or pre-morula embryo cells. In an example, the recipient blastocyst or pre-morula is of a mouse strain, such as C57BL/6 and optionally the ES or iPS cells are of a 129, 129 hybrid, F1H4 or AB2.1 strain.

72. A nucleic acid (eg, a DNA) comprising a transgene for use in the method of Statement 66, the transgene comprising (in 5' to 3' direction)

(a) said intronic enhancer;

(b) said rearranged antibody variable region; and (c) said antibody constant region.

73. A nucleic acid comprising a rearranged variable region sequence encoding a rearranged V domain for use in the method of Statement 67, the nucleic acid comprising said rearranged variable region sequence flanked (a) 5' by a homology arm for hybridising to a first nucleotide sequence of the cell genome, and/or (b) 3' by a homology arm for hybridising to a second nucleotide sequence of the cell genome;

Wherein (c) the 5' homology arm is homologous to a sequence of an antibody light chain (eg, kappa) locus of the cell 5' of the CL region thereof, and the 3' homology arm is homologous to a sequence of said locus 3' of the intronic enhancer (eg, Eιĸ) of the locus, whereby homologous recombination between the homology arms and the genome of the cell is capable of inserting the variable region sequence, thereby producing a locus comprising (in 5 to 3 direction) an intronic enhancer, said variable region and a CL region; or (d) the 5' homology arm is homologous to a sequence of a heavy chain antibody locus of the cell 5' of the Cμ region thereof, and the 3' homology arm is homologous to a sequence of said locus 3' of the intronic enhancer (Eμ) of the locus, whereby homologous recombination between the homology arms and the genome of the cell is capable of inserting the variable region sequence, thereby producing a locus comprising (in 5 to 3' direction) an intronic enhancer, said variable region and a Cμ region.

74. The nucleic acid of Statement 73, wherein nucleic acid or the 5' homology arm comprises (in 5' to 3' direction)

(a) a promoter operable for promoting transcription of the variable region;

(b) a nucleotide sequence encoding a variable domain signal peptide; and (c) Optionally a said intronic enhancer sequence, Wherein when the variable region sequence is inserted into the cell genome, the variable region is inserted in operable connection 3' of the promoter and signal peptide-encoding sequence for expression of an antibody chain comprising (in N- to C-terminal direction) a signal sequence-V domain-C domain.

The invention further provides a composition (eg, a pharmaceutical composition or a composition for medical use) comprising an antibody, bispecific antibody, antibody chain (eg, light chain), VL or nucleotide sequence thereof obtained or obtainable by a method of the invention as disclosed herein; optionally wherein the composition comprises a diluent, excipient or carrier, optionally wherein the composition is contained in an IV container (eg, and IV bag) or a container connected to an IV syringe. When the composition is a pharmaceutical composition or a composition for medical use, the diluent, excipient or carrier is pharmaceutically acceptable. "Pharmaceutically acceptable" refers to approved or approvable by a regulatory agency of the USA Federal or a state government or listed in the U.S. Pharmacopeia or other generally recognized pharmacopeia for use in animals, including humans. A "pharmaceutically acceptable carrier, excipient, or adjuvant" refers to a carrier, excipient, or adjuvant that can be administered to a subject, together with an agent, e.g., any antibody, VL or antibody chain described herein, and which does not destroy the pharmacological activity thereof and is nontoxic when administered in doses sufficient to deliver a therapeutic amount of the agent.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications (including the US counterparts of any of these); cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

It will be understood that particular configurations, aspects, examples, embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications (including US equivalents) are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting Examples.

EXAMPLES

Figure 1:
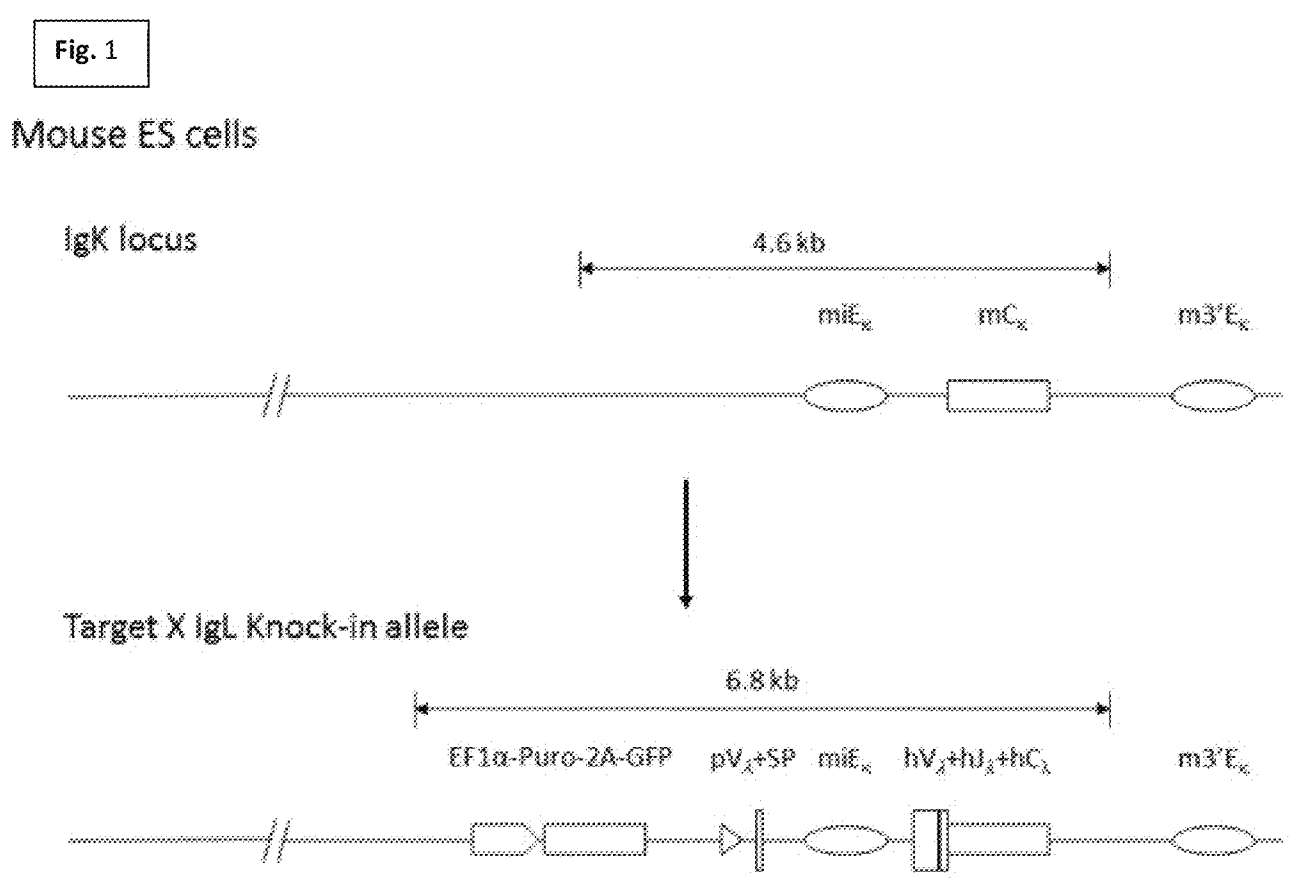

Example 1. Construction of Targeting Vectors for Mouse ES Cell Targeting 1.1 pUC57_N128L_KI Vector DNA Synthesis N128L is a human $\lambda$ light chain rearranged from human IGLV3-21*01 and IGLJ3*02 (VL domain sequence is given below). A DNA fragment containing wildtype human IGLV3-21*01 promoter (pVx) and signal peptide (SP), mouse intronic $\kappa$ enhancer (miE$_K$), and N128L light chain variable region and constant region was synthesized by Genscript. A 1-kb fragment between V$_K$ and J$_K$ region in the kappa locus, and a 1-kb fragment between mouse $\kappa$ constant region (C$_K$) and mouse 3' $\kappa$ enhancer (m3'E$_K$) were used as homology arms for targeting the N128L knock-in cassette. After successful targeting, kappa allele DNA including mouse C$_K$ was replaced by the N128L knock-in (FIG. 1).

1.2 pUC57_N128L_EFla_Puro_2A_EGFP_SV40pA Targeting Vector

EFla_Puro_2A_EGFP_SV40pA vector was digested with NotI and AscI. A 3.6 kb fragment was purified using QIAquick™ PCR Purification Ki (QIAGEN) by the method described in the attached instruction manual. pUC57_N128L_KI vector was digested with NotI and AscI. A 7.9 kb fragment was purified QIAquick PCR Purification Kit (QIAGEN) by the method described in the attached instruction manual. The Notl-AscI-digested EFla_Puro_2A_EGFP_SV40pA and pUC57_N128L_KI fragments were ligated using T4 ligase (New England Biolabs) according to the method described in the attached instruction manual. *E. coli* DH10B strain (ElectroMax™ DH10B (Invitrogen)) was transformed with the ligation solution. Respective plasmid DNAs were isolated from the obtained ampicillin resistant clones using QIAprep™ Spin Miniprep Kit (QIAGEN). The resulting respective ampicillin resistant transformants were confirmed to have the insertion by Sanger sequencing.

1.3 Preparation of Plasmid DNA for Mouse ES Cell Targeting

For pUC57_N128L_EFla_Puro_2A_EGFP_SV40pA targeting vector, plasmid DNA was isolated from the sequencing verified clones using QIAprep Maxi plus Kit™ (QIAGEN) by the method described in the attached instruction manual. Respective plasmid DNAs were confirmed to have the insertion by Sanger sequencing.

Example 2. Generation of N128L Knock-In Mouse ES Cell Lines 2.1 Preparation of Mouse ES Cells Cells from two independent mouse embryonic stem cell (ES) lines were expanded on STO feeder plates for electroporation. ES cells were fed with fresh M15 media until they reached 80% to 85% confluence under microscope. The knock-in construct was introduced using electroporation.

ES cells were cultured in M15 media supplemented with Puromycin (1 μg/mL). Seven days after electroporation, Puromycin resistant colonies were big enough for picking.

2.2 Microinjection of Targeted Mouse ES Cell Clones

Targeted ES cells were injected to C57BL6 strain blastocysts. After injection, blastocysts were transferred to the uterus of C57BL6 strain F1 hybrid females mated with vasectomised males 3 days before injection. The chimaeric embryos were allowed to develop to term in the pseudo-pregnant recipients, which developed into pups comprising the light chain knock-in.

Example 3: Common Light Chain Mice

Eight chimaera mice with common light chain knock-in allele and a functional unrearranged human VH region in an IgH locus were immunized with human Target X.

The knock-in encodes for the following N128L VL (in N- to C-terminal direction):—

```
                                          (SEQ ID NO: 1)
SYVLTQPPSVSVAPGETARITCGGDNIGRKSVYWYQQKSGQAPVLVIYYDS

DRPSGIPERFSGSNSGNTATLTISRVE AGDEADYYCQVWDGSSDHWVTGG

GTKLTVL
```

Figure 2:
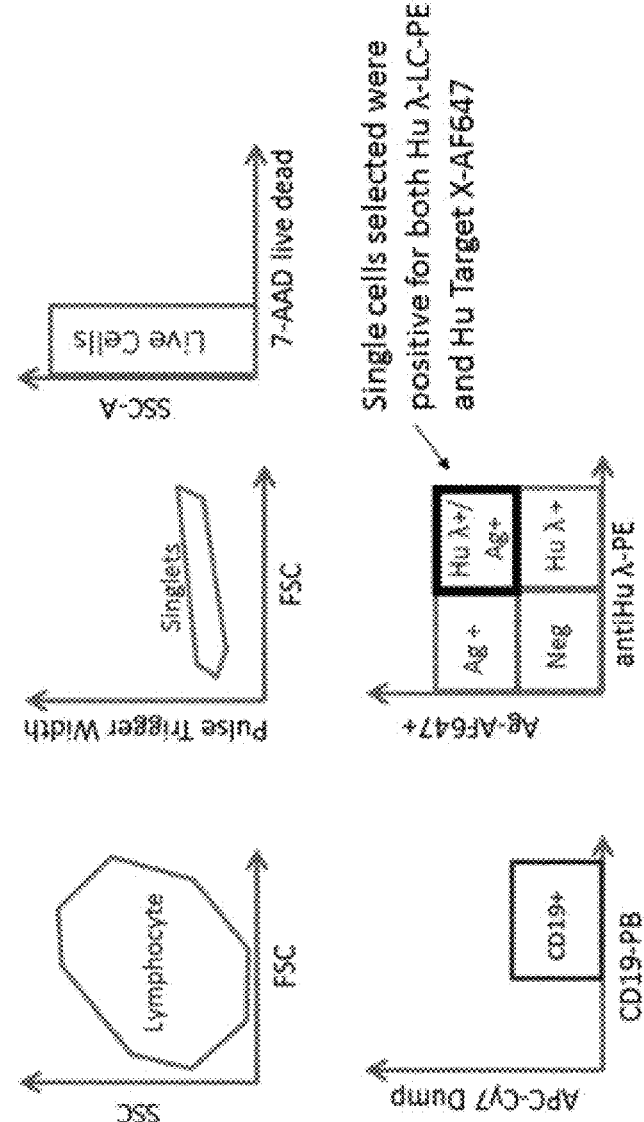
FIG. 2 A schematic of the sorting strategy to isolate spleen B cells that express antibodies with a human λ light chain and specifically bind human Target X from a common light chain knock-in chimera mouse. The sorting strategy involved lymphocyte section, followed by single cell selection, followed by live cell selection, followed by CD19$^+$ B-cell selection and finally human lambda positive and antigen (Target X) positive cell selection. SSC: side scatter. FSC: forward scatter. SSC-A: side scatter area.
Figure 3A:
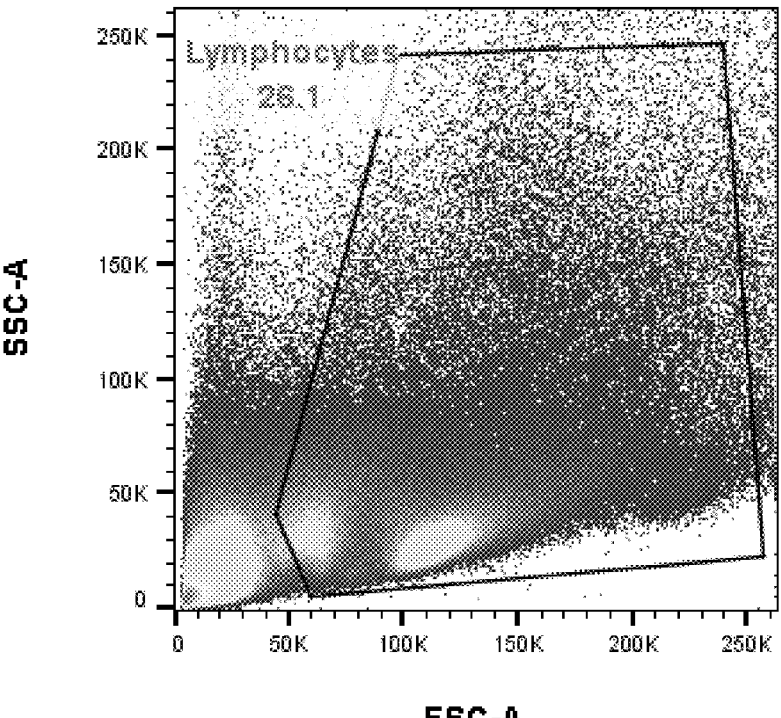
FIGS. 3A-3F Sorting plots showing the isolation of B cells that express antibodies with a human λ light chain and specifically bind human Target X from a common light chain knock-in chimera mouse.
Figure 3B:
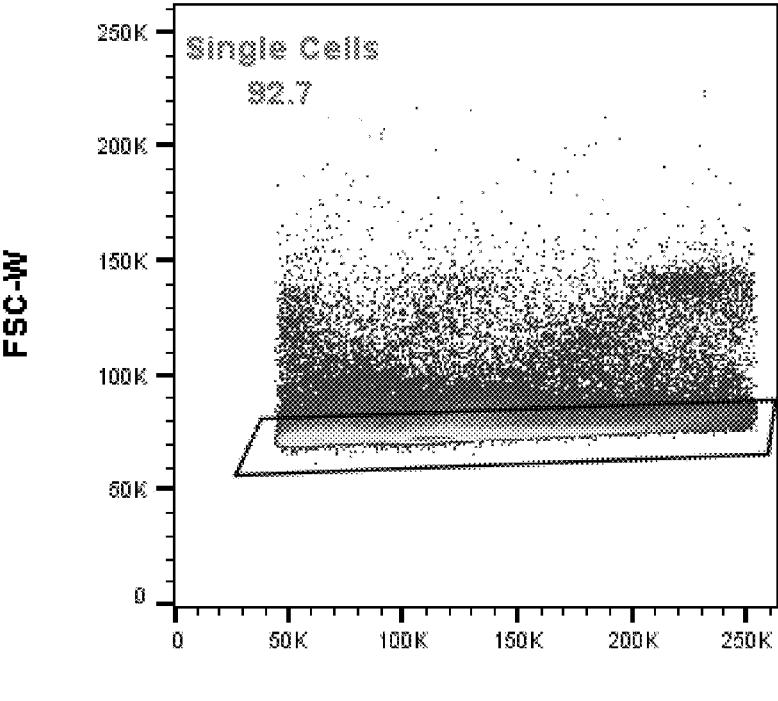
Figure 3C:
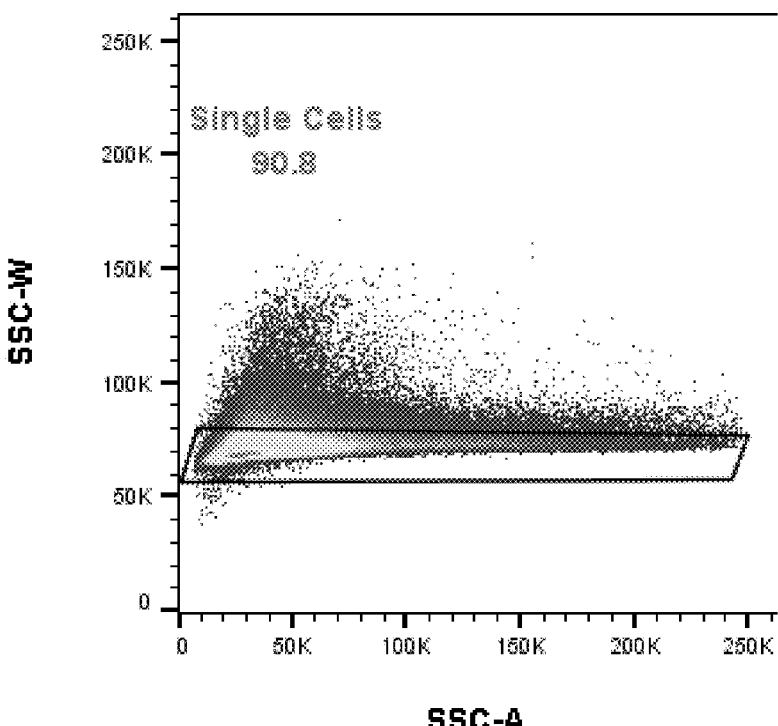
Figure 3D:
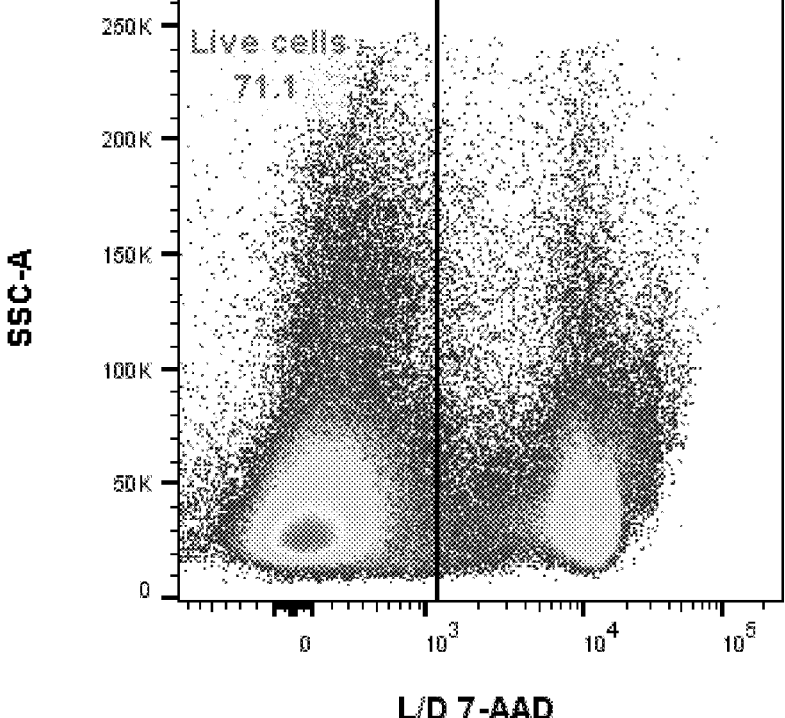
Figure 3E:
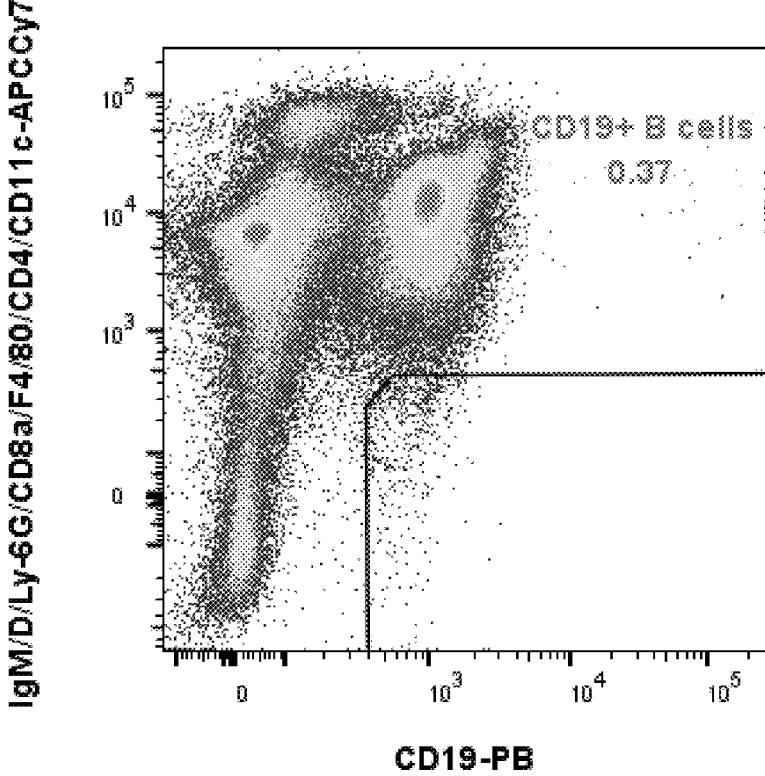
Figure 3F:
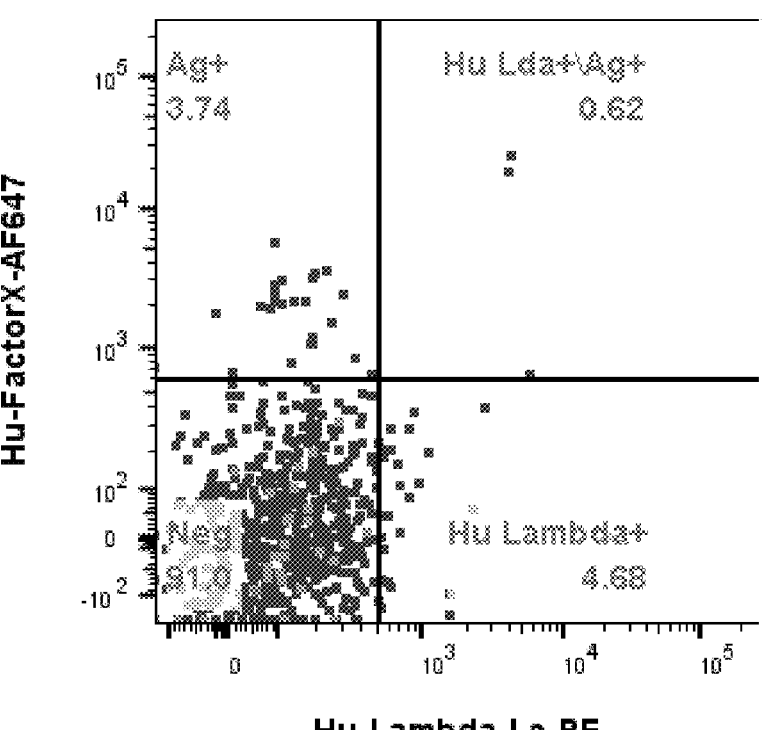

After immunization, sorting was performed on spleen B cells using a monoclonal antibody against human $\lambda$ light chain labelled with PE and human Target X labelled with AF647 (FIGS. 2 & 3). B cells that were positive for both PE and AF647 were sorted as single cell into individual wells on a 96-well plate. Single cell NGS libraries were constructed using standard protocol and subjected to NGS sequencing.

Figure 4:
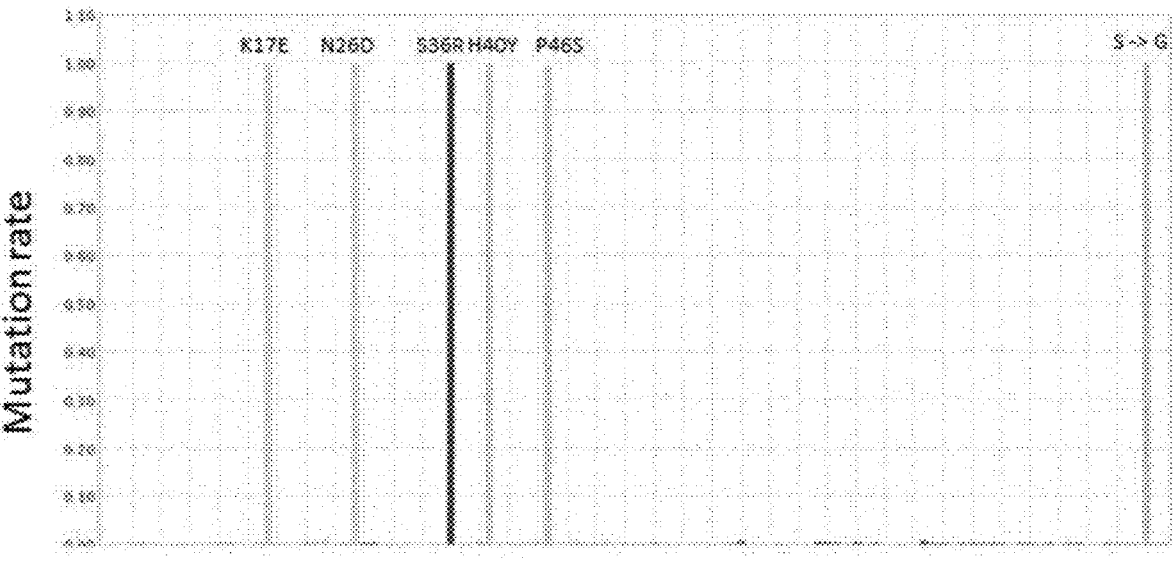
FIG. 4 VL regions of the light chains recovered by NGS essentially all carry the same 6 non-germline mutations as the knock-in common light chain allele.
Figure 5:
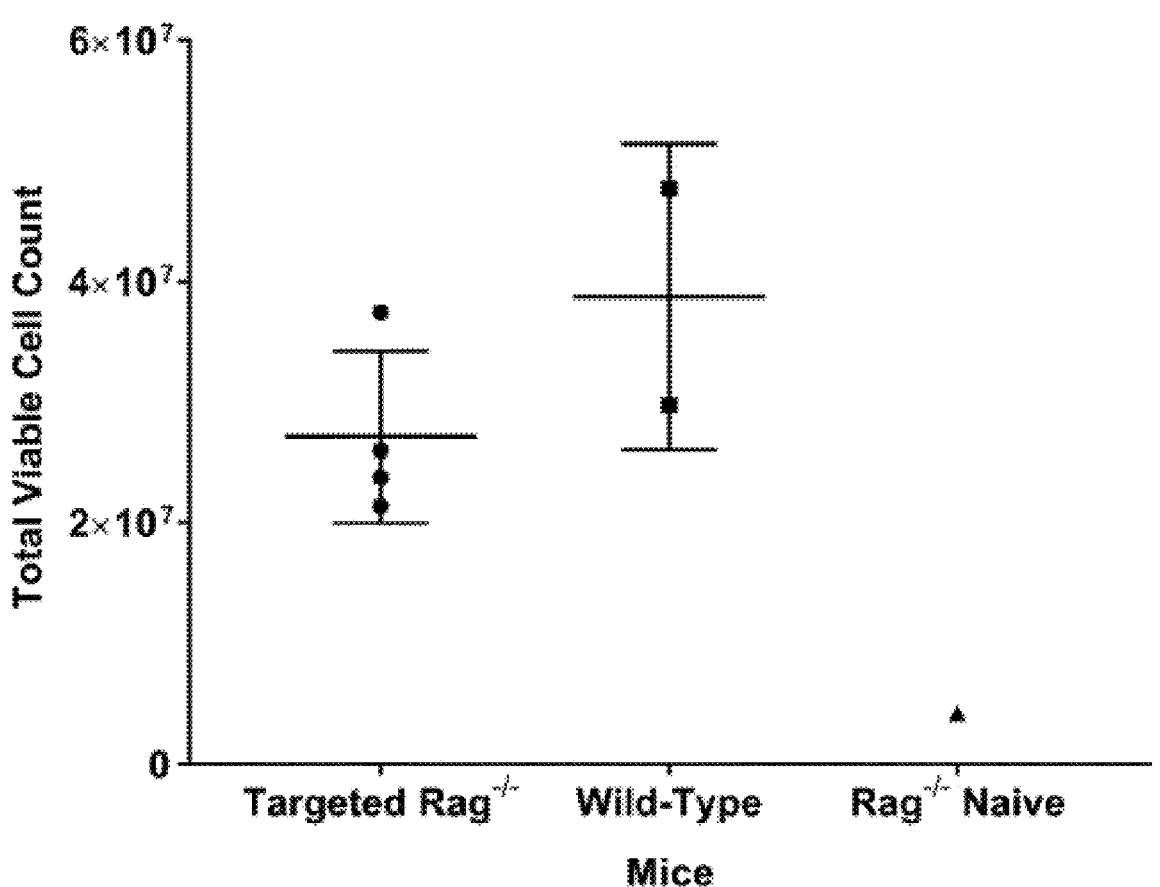
FIG. 5 Chimera mice generated from Rag$^{7-}$ blastocysts micro-injected with targeted ES cells (targeted Rag$^7$) had similar total viable spleen cell number compared to wild-type mice (Wild-Type).
Figure 6:
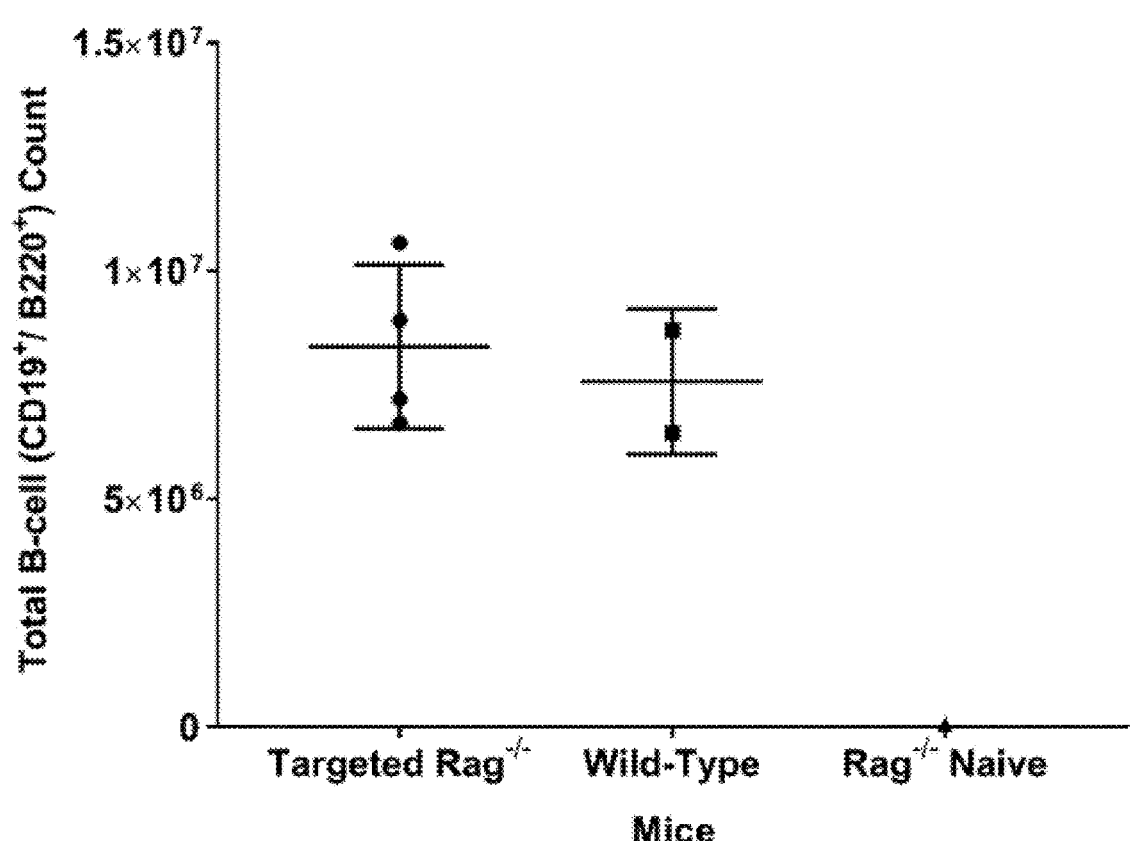
FIG. 6 Chimera mice generated from Rag$^{7'''}$ blastocysts micro-injected with targeted ES cells (targeted Rag$^{7'''}$) had similar CD19-positive, B220-positive B-cell number compared to wild-type mice (Wild-Type).
Figure 7:
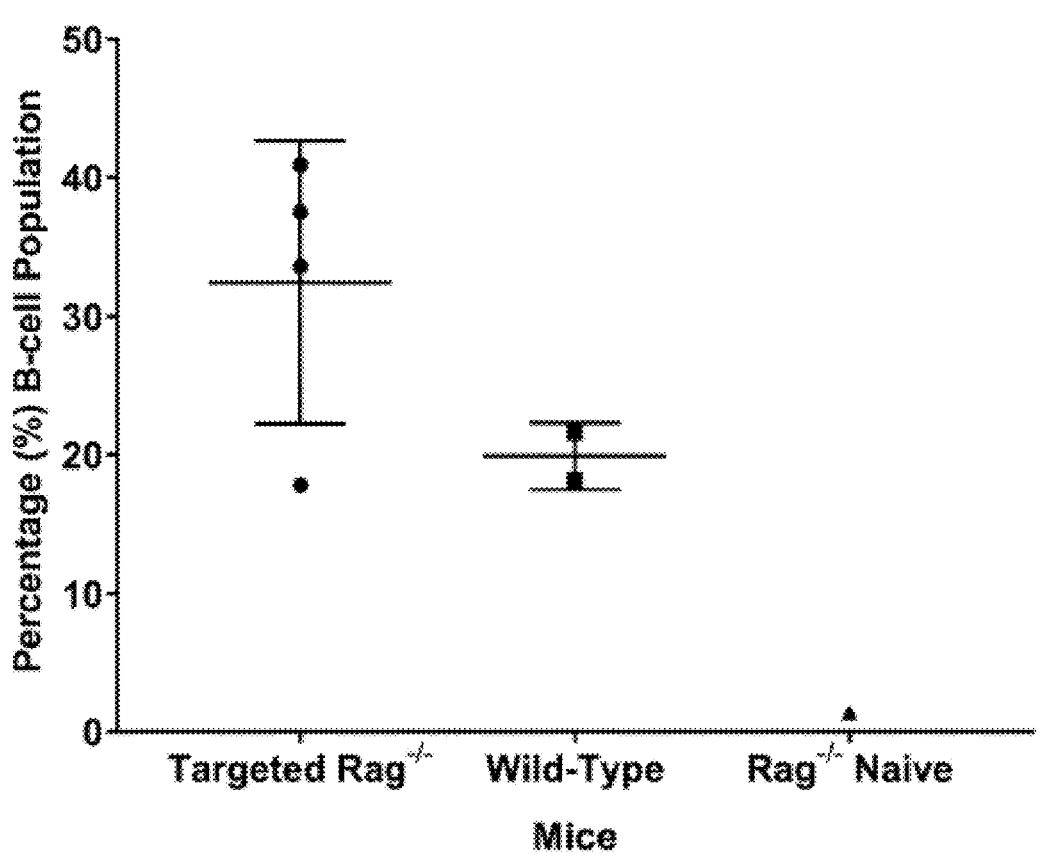
FIG. 7 Percentage CD19-positive, B220-positive splenic B-cell population in chimera mice generated from Rag$^{7'''}$ blastocysts micro-injected with targeted ES cells (targeted Rag$^{7'''}$) was similar to wild-type mice (Wild-Type).
Figure 8:
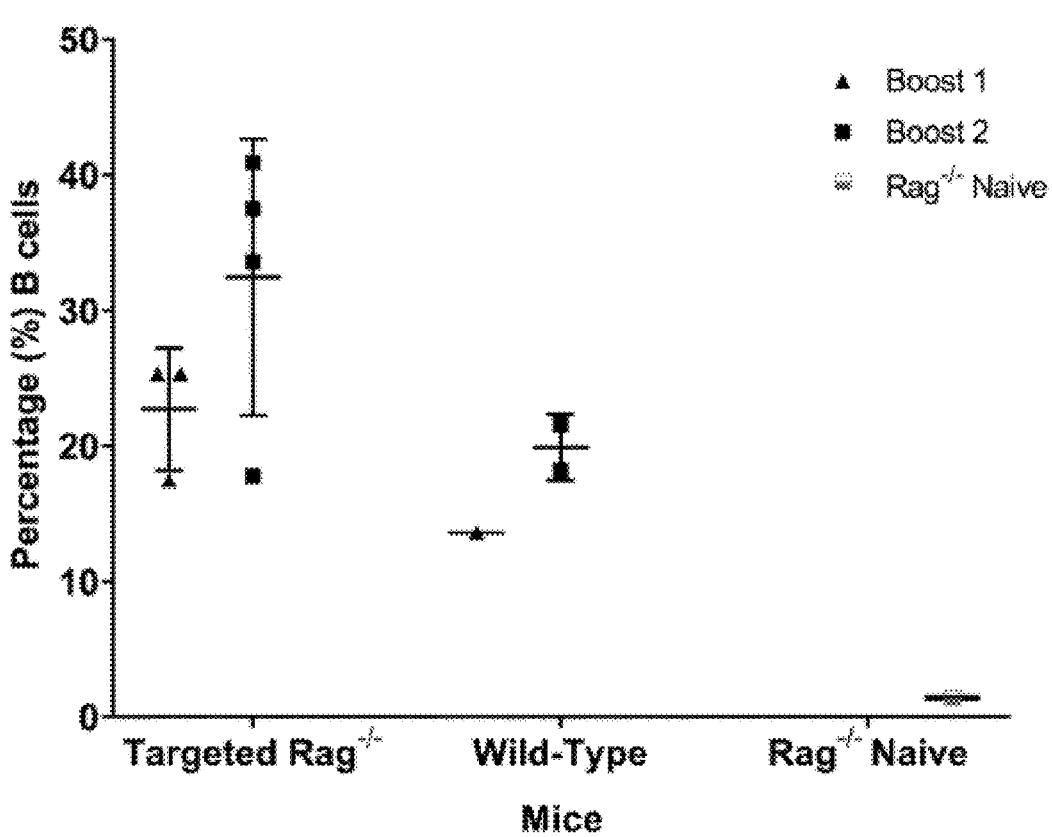
FIG. 8 Percentage CD19-positive, B220-positive splenic B-cell population in chimera mice generated from Rag$^{7'''}$

After subtraction of sequences from a PCR control included in our experiment, we found 346 clones, all of which comprised the expected λ light chain combination derived from IGLV3-21*01 and IGU3*02. Clustering the light chain sequences with that of the knock-in light chain allele demonstrated that 339 out of 346 clones were unmutated, with the other 7 clones having one or more mutations (FIG. 4).

TABLE 1

| Common L Chain Frequencies | |
| --- | --- |
| Number of Clones (out of 346 total) | Percent identity to predetermined human λ light chain rearranged from human IGLV3-21*01 and IGU3*02 |
| 339 | 100.00% |
| 1 | 97.23% |
| 1 | 98.15% |
| 1 | 99.08% |
| 4 | 99.69% |

Compared to sequences that are a perfect (ie, 100%) match for the inserted light chain sequence, ones that do not completely match have lower confidence scores (81.6% confidence score (for the average of the sequences assigned a 100% match) versus 31.7% confidence score (for the average of the 7 other sequences), 100% represents the highest confidence, 0% represents the lowest confidence). Thus, we found that of all the VLs that were based on the human IGLV3-21*01 and IGU3*02 combination, 98% comprised the identical input common light chain V sequence.

After bioinformatics analysis, desirably the human heavy chain V domain sequence repertoire of the clones was found to be diverse. There were no dominant human $V_H$, $D_H$ or $J_H$ usage identified by the bioinformatics analysis. This matches the bulk NGS analysis of variable regions of heavy chains in spleen B cells from naive chimera mice (data not shown).

Human VH gene segment usage comprised the following: IGHV1-3*01, IGHV1-8*01, IGHV1-18*01, IGHV1-46*03, IGHV3-7*01, IGHV3-9*01, IGHV3-11*01, IGHV3-15*01, IGHV3-20*d01, IGHV3-21*03, IGHV3-23*04, IGHV3-30*18, IGHV3-33*01, IGHV3-48*02, IGHV3-53*01, IGHV4-4*02, IGHV4-31*03, IGHV4-34*01, IGHV4-39*01, IGHV4-59*01, IGHV4-61*01, IGHV5-51*01, IGHV6-1*01 and IGHV7-4-1*01.

Example 4: Construction of Common Light Chain Targeting Vector for Mouse ES Cell Targeting Further common light chain mice were made as follows.
Generation of Common Light Chain Targeting Vector A DNA fragment containing wild-type human VA promoter (pVx) and signal peptide (SP), mouse intronic κ enhancer (miE$_K$), and nucleotide sequence encoding a human light chain variable region and constant region was synthesized. The light chain variable domain has specificity for a target (Target Z) other than Target Y used below. A 1 kb fragment between $V_K$ and $J_K$ (1-5), and a 1 kb fragment between mouse κ constant region ($C_K$) and mouse 3' κ enhancer (m3'E$_K$) were used as homology arms for targeting the common light chain knock-in cassette. After successful targeting, the human J$_K$ (1-5) and mouse C$_K$ will be replaced by common light chain knock-in cassette on one or both alleles.

Generation of Common Light Chain Targeted Mouse ES Cells

Cells from two independent mouse embryonic stem cell (ES) lines were expanded on STO feeder plates for electroporation. ES cells were fed with fresh M15 media until they reached 80% to 85% confluence under microscope.

Two hours before electroporation, ES cells were fed with fresh M15 media. Before electroporation, ES cells were washed twice with PBS, and dissociated from plates by adding trypsin. After incubation at 37° C. for 20 minutes, the trypsin was inactivated by adding same volume of M15 media. ES cells were dissociated to a single cell suspension by repeat pipetting. ES cells were pelleted by centrifuging at 1,100 rpm for 4 minutes, and re-suspended in electroporation buffer (Lonza) by the method described in the attached instruction manual.

Electroporation were performed using Lonza Amaxa™ machine using preset mouse ES cell protocol. After electroporation, ES cells from each electroporation were re-suspended in fresh M15 media, and plated onto one 10 cm feeder plate.

ES cells were fed with M15 media for 3 days after electroporation. ES cells from each electroporation were passaged 1:3 to three 10 cm feeder plates. Two days after passage, ES cells were cultured in M15 media supplemented with Puromycin (1 μg/mL). Seven days after electroporation, Puromycin resistant colonies were big enough for picking.

Puromycin resistant colonies on 10 cm STO feeder plates were fed with fresh M15 media 2 hours before picking. 50 μl of trypsin was added to each well of a 96-well round bottom plate. Colonies on 10 cm STO feeder plates twice with PBS buffer. 10 ml of PBS buffer was added to each 10 cm plate.

Single colonies were picked from the feeder plates using a Gilson pipette, and transferred into the well with trypsin of 96-well plate (1 colony/well). After completing a plate (96 colonies picked), the trypsin plate was incubated at 37° C. for 30 minutes. After that, 150 μl of fresh M15 media was added to each well. Colonies were dissociated by repeat pipetting. Single cell suspension was transferred to a 96-well feeder plate and cultured in a TC incubator at 37° C. ES cells were fed with fresh M15 media until they reached 80% to 85% confluence under microscope.

Passaging Common Light Chain Mouse ES Cells

Two hours before passaging, ES cells were fed with fresh M15 media. Before passaging, ES cells were washed twice with PBS buffer, and dissociated from plates by adding trypsin. After incubation at 37° C. for 20 minutes, the trypsin was inactivated by adding same volume of M15 media. ES cells were dissociated to a single cell suspension by repeat pipetting.

Single ES cell suspension were split 1:4 to four 96 well STO feeder plates. ES cells were fed with fresh M15 media until they reached 80% to 85% confluence under microscope.

Freezing ES Cells on 96 Well Plate

Two hours before freezing, ES cells were fed with fresh M15 media. Before freezing, ES cells were washed twice with PBS buffer, and dissociated from plates by adding trypsin. After incubation at 37° C. for 20 minutes, the trypsin was inactivated by adding same volume of 2× freezing media (60% DMEM, 20% FBS, 20% DMSO, freshly prepared). ES cells were dissociated to a single cell suspension by repeat pipetting. 96 well plates were sealed and placed in a polystyrene box inside a −80° C. freezer to facilitate a very slow freezing process.

Genomic DNA Extraction

ES cells were washed twice with PBS buffer, and 50 μι of ES cell Lysis Buffer (10 mM Tris-HCI, pH 7.5, 10 mM EDTA, 0.5% SDS, 10 mM NaCI) with Proteinase K (1 mg/mL) was added to each well of the 96 well plates. The plates were sealed, wrapped with wet tissues, and placed into a lunch box. The lunch box was incubated at 55° C. overnight.

The second day, 100 μι ice-cold Ethanol/NaCI mix (1.5 mL 5M NaCI added to 98.5 mL 100% ethanol) was added to each well of the 96 well plates. The plates were at room temperature for about 30 minutes. After incubation, the plates were centrifuged at 3,000 rpm for 20 minutes. The plates were inverted to decant liquid, and dried on paper towels to remove access liquid. The plates were washed twice by adding 150 μι cold 70% ethanol, and dried completely on paper towels. After the DNA pellets were dried, 30 μι of TE (pH 8.0) buffer was added and DNA was resuspended by incubation at 55° C. for 30 minutes.

Thawing and Expansion of Common Light Chain Mouse ES Cell Clones

Frozen 96 well plates were taken out of the −80° C. freezer, and thawed in a 37° C. incubator until every well of the plates became transparent. 2 mL fresh M15 media was added to each well of 24 well STO feeder plates. All the contents from the desired wells of the 96 well plates were transferred to a well of the 24 well plates. After all the targeted clones were transferred to a 24 well plate, the plate was cultured in a TC incubator at 37° C. ES cells were fed with fresh M15 media until they reached 80% to 85% confluence under microscope. Once they became confluent, they were 1:1 passaged to 6-well STO feeder plates and frozen down for microinjection.

Microinjection of Common Light Chain Mouse ES Cell Clones

Mouse ES cells were thawed and expanded before injection. Two hours before injection, ES cells were fed with fresh M15 media. Before injection, ES cells were washed twice with PBS buffer, and dissociated from plates by adding trypsin. After incubation at 37° C. for 20 minutes, the trypsin was inactivated by adding same volume of fresh M15 media. ES cells were dissociated to a single cell suspension by repeat pipetting, and put on ice for injection.

Targeted ES cells were injected to E3.5 Rag$^{7-}$ blastocysts. After injection, blastocysts were transferred to the uterus of CBA; C57BL6/J F1 hybrid females mated with vasectomised males 3 days before injection. The chimeric embryos were allowed to develop to term in the pseudo-pregnant recipients. The resulting mice comprised cells derived from the engineered ES cells, where the cell genomes comprised the human lambda light chain knock-in at one mouse kappa locus (the other kappa locus was inactivated by deletion in the J region) and an unrearranged human heavy chain variable region comprised by a homozygous IgH locus.

Example 5: Production of Antibody to Target Y

Immunization

Common light chain chimera mice were immunized with Target Y as described below. As the first immunization, 40 μg/head of Target Y, emulsified by CpG (Sigma) and Alum (1:1 antigen), was subcutaneously administered. Four weeks later, 5 μg/head of Target Y, emulsified by CpG (Sigma) and Alum (1:1 antigen) was administered by intraperitoneal injection (first boost). One week later, four mice were sacrificed and the spleens were extracted. Four weeks after the first boost, 2 μg/head of Target Y, emulsified by CpG (Sigma) and Alum (1:1 antigen) was administered by intraperitoneal injection (second boost) to the another four mice One week later these mice were sacrificed, and the spleens were extracted.

Antigen Specific B Cell Sorting

Harvested and processed spleen tissues were resuspended in 20 mL 3% FBS/PBS. Cells were pelleted at 300 g for 10 seconds at 40° C., and resuspended in 300 μl 3% FBS/PBS buffer.

20 ul of Fe blocker was added for 10 seconds and stored at 4° C. before use.

Alexa-647 labelled human Target Y stock solution (0.8 mg/mL) was diluted to 20 μg/mL and used at 1:40 dilution (final concentration 0.5 μg/mL) for staining.

A 100 μl staining cocktail containing CD19-PB, lgM-APC-Cy7, lgD-APC-Cy7, CD38-FITC, CD95-PE, Hu-Target Y-Alexa 647, was mixed and added to 300 μl spleen cell suspension. After incubation at 4° C. for 20 minutes, 5 ml of 3% FBS/PBS buffer was added to the samples. Cells were pelleted at 300 g for 10 minutes, and resuspended in 400 μl of 3% FBS/PBS buffer and filter through 30 μm cell strainer. Five minutes before sorting, 8 μl of 7AAD (1:100 dilution) was added. The gating strategy for sorting is shown below.

B-Cell Screening (BCT) and Recovery of Coupled Antibody Heavy and Light Chains for Expression BCT technology is generally described in WO2015/040401, which is incorporated herein by reference.

For RT, a mixture of 0.1 μι of a IgG constant region specific primer (10 μM), 0.1 μι of a IgK constant region specific primer (10 μM), 0.05 μι a IgL constant region specific primer (10 μM), 1 μι dNTP mix (10 mM), 2 μι of 5× First-Strand Buffer, 1 μι, of 0.1 M DTT, 0.4 μι of RNase-OUT™ RNase Inhibitor (Invitrogen), 0.25 μι, of Superscript™ III RT (200 units/μI, Invitrogen), and 1.1 μι of RNase-free water were added to each well to make a final volume of 10 μι. RT reactions were performed to generate 1$^{st}$ strand cDNA.

For 1$^{st}$ round PCR, a mixture of 12.5 gμι, of 2× Q5 master mix, 0.15 μι of a mixture of VH specific primers (10 μM), 0.1 μM of a mixture of VL specific primers (10 μM), 0.15 μι of a mixture of VK specific primers (10 μM), 0.1 μι of a IgG constant region specific primer (10 μM), 0.1 μι of a IgK constant region specific primer (10 μiti), 0.1 μι of a IgL constant region specific primer (IO μiti), and 1.8 μι of RNase-free water was mixed with 10 μι of RT product in each well to make a final volume of 25 μι. PCR reactions were performed to amplify heavy chain and light chain variable regions.

For 2$^{nd}$ round PCR, a mixture of 12.5 μι of 2× Q5 master mix, 0.2 μι of a VH nested PCR primer (10 μM), 0.2 μι of a VK nested PCR primer (10 μM), 0.2 μι of a VL nested PCR primer (10 μM), 0.2 μι of a IgG constant region nested PCR primer (10 μM), 0.2 μι of a IgK constant region nested PCR primer (10 μM), 0.2 μι of a IgL constant region nested PCR primer (10 μM), and 10.3 μι of RNase-free water was mixed with 1 μι of 1$^{st}$ round PCR product in each well to make a final volume of 25 μι. PCR reactions were performed to amplify heavy chain and light chain variable regions.

For bridge PCR, a mixture of 15 μι of 2× Q5 master mix, 0.1 μι of Heavy Vector (100 ng/μI), 0.05 μι of Kappa vector (100 ng/μI), and 1 μι of HLP479/480 mix (10 μM each), and 12.85 μι of RNase-free water was mixed with 1 μι of 2$^{nd}$ round PCR product in each well to make a final volume of 25 Up. PCR reactions were performed to amplify heavy chain and light chain variable regions.

Expi293F Cell Transfection

See Examples 6 and 7 for more details of antibody expression and purification.

One day before transfection, cultured Expi293F cells (Invitrogen) were counted for cell seeding calculation. Expi293F cells were pelleted at 300 rpm for 10 minutes. Cells were resuspended in pre-warmed fresh Expi293 expression media to give a final dilution of $2.5 \times 10^5$ cells/ml. 200 ml of cell suspension was incubated in a Kuhner Shaking Incubator (37° C., 140 rpm, 8% CO2) until next morning.

On the day of transfection, cultured Expi293F cells were counted and diluted to $4 \times 10^6$ cells/ml using fresh Expi293 expression media. 500 μl of cell suspension was aliquoted into each well of 96-well deep well plates using Multidrop Combi. After dispensing, the plates were covered with Duetz sandwich cover, and incubated in a Kuhner Shaking Incubator (37° C., 300 rpm, 50 mm orbital throw, humidity 80%) for 2-2.5 hours.

For each transfection, two mixtures were prepared.

Mix 1: 25 μl B cell bridge product+55 μl SM+100 ng PBase per well

Mix 2: IμI ExpiFectamine™ 293 (Invitrogen)+79 μl RSM

Mix 2 was added to Mix 1 and incubated at room temperature for 15 minutes. The incubated mixture was then added to the 500 μl of cell culture solution and incubated in a Kuhner Shaking Incubator (37° C., 300 rpm, 50 mm orbital throw) for a week.

Example 6: Expression of Antibodies

Mammalian transient expression systems enable flexible and rapid production of proteins. They are ideal for expression of human or other mammalian proteins because these systems generate recombinant proteins with more native folding and post-translational modifications.

1. The day before transfection, Expi293 cells were counted by an automated cell counter (Eve cell counter) seeded in pre-warmed expression media at the density of $\sim 1.7 \times 10^6$ cells/ml and incubated overnight in an orbital shaker incubator (37° C., 8% CO2, 140 rpm)

2. On the day of transfection, cells were counted and adjusted the cell number to $2.5 \times 10^6$ cells/ml. 2000 μl of cell suspension were dispensed into 24 Deep Well Plates and placed into Kuhner shaking incubator (37° C., 8% CO2, 225 rpm)

Preparation of DNA Solutions

Mixed solutions containing plasmid DNA were prepared for transfection of Expi293 cells. For 2 mL of cell culture, 1 μg each of the heavy chain expression plasmid and the light chain expression plasmid were used. 2 μg of DNA plasmid mixture diluted in ultrapure water was used for each transfection. Transfection Two mixtures were prepared:

Mix 1: 2 μg of plasmid DNA diluted in 40 μl of Opti-MEM® I medium.

Mix 2: 80 μl of ExpiFectamine™ 293 transfection reagent+40 μl of OptiMEM I medium. Mix 2 was combined with Mix 1 and incubated for 20-30 minutes at room temperature. After the incubation was complete 165 μl of DNA-ExpiFectamine™ 293 Reagent complex was dispensed to each well of the 24 deep well plate. Cells were incubated in the Kuhner shaking incubator (37° C., 8% C02, 225 rpm) for 6 days. Cell culture supernatants were harvested 6 days after transfection.

Example 7: Purification of Antibodies from Common Light Chain Mouse

A 96-well plate purification was employed to purify antibodies from Expi293F cell culture supernatants. This method allows rapid small-scale affinity antibody purification of multiple samples in antibody screening experiments. To achieve high % of recovery MabSelect Sure LX™ was used which is a protein A affinity with very dynamic binding activity (60 mg human IgG/ml medium), an extended residence time, alkali tolerant and low ligand leakage.

Procedure

1. MabSelect Sure LX resin (GE Healthcare) was equilibrated in IX PBS (Gibco) to remove the storage buffer, to a final concentration of 10% slurry.

2. 600 μl of 10% slurry is added to each well of the 96 well plate AcroPrep™ Advance (Pall)

3. The resin was centrifuged 70×rcf for 1 min at 4 C.

4. The resin was washed with 300 μl IX PBS, spin 70×rcf for 1 rain. This step was repeated twice.

5. 2 ml of cell culture supernatants (pH 7-8) were loaded onto the MabSelect Sure LX resin into the 96 well purification plate and centrifuged at 70-100×rcf for 1 minute.

6. Plate was washed using 600 μl of 1×PBS and centrifuged at 70-100×rcf for 1 minute. This step is performed four times in total.

7. 70 μl of elution buffer (IgG Elute Pierce) was added to each well and incubated for 1 min.

8. The plate was centrifuged at 70-100×rcf for 1 minute to collect the eluate. This step is performed two times in total.

Example 8: SPR Analysis of Antibody for Antigen Y

AIM of Experiment

A SPR analysis was performed to determine the binding affinity and the kinetics of interaction of the Hit 1 (ie, a lambda-type antibody from our common light chain mouse) to Target Y. The affinity and the kinetics of the purified antibody was compared to the benchmark and an isotype control (ISTC).

Methods

Surface plasmon resonance (SP) was used to determine the binding affinity ($K_D$) to the antigen Y, the kinetic constants on-rate ($k_{on}$) and off-rate ($k_{off}$). The analysis was performed using a Biacore 8K (GE Healthcare) system.

An anti-human IgG Fe antibody was immobilised on CM4 chip (GE Healthcare catalogue number BR100534) according to manufacturer's instructions. Amine coupling kit (BioRad) was used to activate the surface of the chip. The surface was subsequently blocked with 1M ethanolamine. The immobilisation run was performed at 25° C. using HBS-EP as immobilisation running buffer.

The purified monospecific antibodies (referred as ligand) from Example 7 were captured onto the anti-human IgG Fc CM4 surface at approximately 2 ug/ml. The ligands were injected for 60 seconds at 10 ul/min in all the active channels of all 8 flow channels. The run was performed at 25° C. using neutral pH HBS-P IX+CaCl2 2.5 mM as running buffer.

Human antigen Y was reconstituted at 1 mg/ml in the running buffer and used as analyte. The antigen Y was injected in multiple cycle kinetics (MCK) mode at 3 concentrations (1.5 uM, 500 nM and 166.7 nM) with 120 seconds association phase and 200 seconds dissociation phase, at flow rate 30 ul/sec in both active and reference channels. Three injections of 10 mM Glycine pH 1.5 for 60 sec. at 10 µl/min were used for the regeneration phase.

An isotype control antibody hIgG4PE KYAB2229 (ISTC; this does not specifically bind antigen Y) was captured at 1 ug/ml for 60 sec at 10 µl/min in the reference channel. An isotype control antibody hIgG4PE was also captured in the active channel as a negative control. Two antibodies against antigen Y, were used as benchmarks (Benchmark 1 and Benchmark 2). The data were reference and buffer subtracted and fitted into Langmuir 1:1 model. The first 30 seconds of dissociation were evaluated in the model.

Table 2. Binding affinity and kinetic constants on-rate ($k_{on}$) and off-rate ($k_{off}$) of anti-antigen Y antibodies Captured Antibody kon (1/Ms) koff (1/s) M)
Benchmark 1 $2.94 \times 10^4$ $4.27 \times 10^2$ $1.45 \times 10^6$
Benchmark 2 $4.13 \times 10^4$ $2.72 \times 10^2$ $6.60 \times 10^7$
Antibody Hit 1 $1.19 \times 10^5$ $1.25 \times 10^1$ $1.05 \times 10^6$
hIgG4PE ISTC NB The association and dissociation data of the interaction were fitted using biomolecular reaction model (1:1 Langmuir model). The values for association rate constant ($k_{on}$), dissociation rate constant ($k_{off}$) and dissociation constant ($K_D$> were calculated from the binding data by BIAevaluation software.

Benchmark 1: antibody anti-antigen Y
Benchmark 2: antibody anti-antigen Y
N B: no binding observed
hIgG4PE ISTC: human isotype control IgG4
Hit 1 antibody was in IgG4PE format.

Conclusion

Hit 1 showed binding to antigen Y in the affinity range provided in Table 2 and fast association ($k_{on}$) and dissociation ($k_{off}$) rates for antigen Y. No binding to antigen Y was observed with ISTC.

Hit 1 antibody shows similar kinetic rates and binding affinity to antigen Y compared to the benchmark antibodies. This shows that our common light chain mice can generate antibodies with human variable domains that specifically bind to target antigen with desirable binding kinetics.

Example 9: Analysis of B-Cell Populations from Common Light Chain Mice

We analysed the B-cell compartments of mice of the invention. The results are shown in FIGS. 5 to 9 as follows. "Targeted Rag$^{7'}$" mice were mice produced as described in Example 4, derived from engineered ES cells. Thus, the genomes of the mice comprised the rearranged human lambda light chain knock-in and an unrearranged human heavy chain variable region comprised by a IgH locus.

FIG. 5

Chimera mice generated from Rag$^{7'}$ blastocysts micro-injected with targeted ES cells (targeted Rag$^{7'}$) had similar total viable spleen cell number compared to wild-type mice (Wild-Type). Total viable spleen cell number following immunisation (antigen prime followed by two antigen boosts) with undisclosed antigen (Target Y). As a control, un-immunised Rag$^{7'}$ deficient mice displayed low total viable spleen cell number. Targeted Rag$^{7'}$, chimera mouse derived from targeted ES-cells and Rag$^{7'''}$ deficient blastocysts; Wild-Type, wild-type mouse; Rag$^{7'''}$ Naive, un-immunised Rag$^{7'}$ deficient mice.

FIG. 6

Chimera mice generated from Rag$^{7''}$ blastocysts micro-injected with targeted ES cells (targeted Rag$^{7''}$) had similar CD19-positive, B220-positive B-cell number compared to wild-type mice (Wild-Type). Total splenic B-cell number following immunisation (antigen prime followed by two antigen boosts) with undisclosed antigen (Target Y). As a control, un-immunised Rag$^{7''}$ deficient mice (Rag$^{7-}$ Naive) displayed minimal total B-cell (CD19/B220) number. Targeted Rag$^{7''}$, chimera mouse derived from targeted ES-cells and Rag$^{7''}$ deficient blastocysts; Wild-Type, wild-type mouse; Rag$^{7''}$ Naive, un-immunised Rag$^{7''}$ deficient mice.

FIG. 7

Percentage CD19-positive, B220-positive splenic B-cell population in chimera mice generated from Rag$^{7''}$ blastocysts micro-injected with targeted ES cells (targeted Rag$^7$) was similar to wild-type mice (Wild-Type). Percentage CD19-positive, B1220-positive splenic B-cell population following immunization (antigen prime followed by two antigen boosts) with undisclosed antigen (Target Y). As a control, un-immunised Rag$^{7''}$ deficient mice (Rag$^{7''}$ Naive) displayed minimal percentage CD19-positive, B220-positive splenic B-cell population. Targeted Rag$^{7''}$, chimera mouse derived from targeted ES-cells and Rag$^{7''}$ deficient blastocysts; Wild-Type, wild-type mouse; Rag$^{7''}$ Naive, un-immunised Rag$^{7'}$ deficient mice.

FIG. 8

Percentage CD19-positive, B220-positive splenic B-cell population in chimera mice generated from Rag$^{7'}$ blastocysts micro-injected with targeted ES cells (targeted Rag$^7$) was similar to wild-type mice (Wild-Type). Percentage CD19-positive, B220-positive splenic B-cell population following immunisation (antigen prime followed by either one or two antigen boosts) with undisclosed antigen (Target Y). As a control, un-immunised Rag$^{7''}$ deficient mice (Rag$^{7''}$ Naive) displayed minimal percentage CD19-positive, B220-positive splenic B-cell population. Targeted Rag$^{7''}$, chimera mouse derived from targeted engineered ES-cells and Rag$^{7''}$ deficient blastocysts; Wild-Type, wild-type mouse; Rag$^{7'}$ Naive, un-immunised Rag$^{7'}$ deficient mice.

FIG. 9

Percentage antigen positive IgG B-cell population in chimera mice generated from Rag$^{7''}$ blastocysts micro-injected with targeted ES cells (targeted Rag$^7$) was similar to wild-type mice (Wild-Type). Percentage antigen positive, CD19-positive or B220-positive, IgM-negative and IgD-negative splenic B-cell population following immunisation (antigen prime followed by either one or two antigen boosts) with undisclosed antigen (Target Y). Targeted Rag$^{7''}$, chimera mouse derived from targeted engineered ES-cells and Rag$^{7''}$ deficient mice; Wild-Type, wild-type mouse.

Conclusion

"Targeted Rag$^{7''}$" chimera mice derived from engineered ES cells micro-injected into Rag$^{7''}$ deficient blastocysts produced IgM-negative, IgD-negative, antigen-positive splenic B-cells following an antigen prime and either one or two antigen boosts in a manner similar to wild-type mice. In comparison, non-chimeric Rag$^{7''}$ deficient mice did not produce splenic B-cells. These observations support our observation that mice generated from engineered ES cells micro-injected into Rag$^7$ blastocysts have a functional immune response which generated antigen positive IgG B-cells in response to an immunisation regime.

Usefully, a respective copy of the common light chain can be paired with a copy of a heavy chain from an antibody (isolated from an immunised common light chain mouse of the invention) that binds to Target Y and a copy of a heavy chain from an antibody that binds Target Z to produce a bispecific 4-chain antibody that specifically binds Y and Z. This can be expressed from a cell (eg, a eukaryotic, mammalian, human, CHO, Cos or HEK293 cell) that comprises (i) an expressible nucleotide sequence encoding the light chain; (ii) an expressible nucleotide sequence encoding a heavy chain that specifically binds Target Y; and (iii) an expressible nucleotide sequence encoding a heavy chain that specifically binds Target Z. Alternatively, the cell comprises (i) and (ii) and a second cell comprises (iii), wherein the heavy and light chain expression products of the cells can be mixed to produce the bispecific antibody. Alternatively, the cell comprises (i) and (iii) and a second cell comprises (ii), wherein the heavy and light chain expression products of the cells can be mixed to produce the bispecific antibody. Alternatively, the cell comprises (ii) and (iii) and a second cell comprises (i), wherein the heavy and light chain expression products of the cells can be mixed to produce the bispecific antibody. Alternatively, (i), (ii) and (iii) are comprised by separate, respective cells and the antibody chain expression products of the cells are mixed to produce a bispecific antibody. In an example, the heavy chain constant regions comprise motifs or mutations (eg, charge pairs or knobs-in-holes motifs, see references above) that promote pairing of the anti-Target Y heavy chain with the anti-Target Z heavy chain.

Methodology

Introduction:

Following immunisation with antigen Y, splenic B-cells expressing class switched antibodies specific for said antigen were processed and single cell sorted. Targeted Rag$^{7-}$ chimera mice were analysed for evidence of a functional immune system and were compared to wild-type control mice. An additional comparison was also made to non-chimeric Rag$^{7-}$ mice, which demonstrate a minimal baseline immune response.

Materials:

TABLE 3

Table of reagents:

| Reagent | Supplier | Cat # | Lot # |
|---|---|---|---|
| RPMI | Gibco | 11835-063 | 1881906 |
| Heat-inactivated Foetal Bovine Serum | Gibco | 10270-106 | 08G2073K |
| RNA Lysis buffer | Epicentre | QER090150 | 20151690 |
| TruStain fcX/Fc blocker | Biolegend | 101320 | 8221805 |
| 7-AAD | eBioscience | 00-6993-50 | 4298663 |
| CD19-BUV395 | BD Horizon | 563557 | 7125716 |
| CD45R/B220-BUV395 | BD Horizon | 563793 | 7177756 |
| IgM-BV786 | BD Horizon | 564028 | 7048650 |

TABLE 3-continued

Table of reagents:

| Reagent | Supplier | Cat # | Lot # |
|---|---|---|---|
| IgD-BV605 | BD Horizon | 563003 | 7226860 |
| Ly-GG-APCCy7 | BD Pharmingen | 557661 | 7040615 |
| CD8a-APC-H7 | BD Pharmingen | 560182 | 7110593 |
| F4/80-APCCy7 | Biolegend | 123118 | B217243 |
| CD4-APC-H7 | BD Pharmingen | 560181 | 7012678 |
| CD11c-APC-Cy7 | BD Pharmingen | 561241 | 7096608 |
| ACK Lysis Buffer | Life Technologies | A10492-01 | N/A |
| Undisclosed antigen Y-647 (1 μg/ml) | in-house | | |

Method

Processing of Samples:

Spleens from immunized mice were removed and homogenised using 40 μιτι cell strainers using aseptic procedures. Cells were pelleted by centrifugation (350 rcf for 10 minutes at 4° C.) and the supernatant was carefully aspirated. Red blood cells were removed by lysis using 1 ml of ACK lysis buffer and incubated for 2 minutes at room-temperature. The lysis reaction was terminated by adding an excess of 3% FBS/RPMI buffer. Cells were subsequently filtered using 40 μιτι cell strainers, pelleted as before and resuspended in 340 μl buffer. Any Fe receptors expressed on processed cells were blocked, removing non-specific staining of B-cells whilst maintaining antibody-mediated specific staining, using Fe blocker. At this stage a total cell count was taken.

Staining:

Single-cell suspensions prepared from spleens were stained in the following manner. Mature, class-switched B-cell spleen populations were defined using BUV395-conjugated anti-CD45R (selecting), BUV395-conjugated anti-CD19 (selecting), BV786-conjugated anti-lgM (depleting) and BV605-conjugated anti-lgD (depleting). Cells other than B-cell such as neutrophils and monocytes, CD8-postive T-cells, macrophages, CD4 positive T-cells and dendritic cells were excluded using APCCy7-conjugated anti-Ly-6G/C, APC-H7-conjugated anti-CD8a, APCCy7-conjugated anti-F4/80, APC-H7-conjugated anti-CD4 and APC-Cy7-conjugated anti-CD11c, respectively. Antigen positive populations were identified using the same antigen used for immunisation labelled with Alexa-647. Non-viable cells were excluded using 7-AAD. An antigen-unlabelled control pool of cells was created to allow a FMO (Fluorescence Minus One) to be derived. Additional positive staining controls and 7AAD (live/dead) controls were also taken. All staining reactions were incubated at 4° C. for 20 min using $1 \times 10^5$ cells in 100 μl of PBS with 3% FBS. Samples were washed twice in 400 μl PBS with 3% FBS and analyzed on BD FACSAria Fusion flow cytometer (BD Biosciences). All acquired data were analyzed using Flow-Jo™ software. Cells of interest were single cell sorted directly into 96 well plates containing RNA lysis buffer. Samples were then processed using B-Cell Technology (BCT).

We claim:

1. An isolated cell comprising a first antibody kappa light chain locus comprising in 5' to 3' direction:
    (a) a light chain Eiκ intronic enhancer;
    (b) a rearranged antibody variable region encoding a first rearranged antibody Vκ domain; and
    (c) an antibody light chain constant region encoding a kappa light chain C domain;
    wherein said kappa light chain locus is operable to express an antibody chain comprising in N- to C-terminal direction said rearranged antibody Vκ domain and said kappa light chain C domain, and wherein the isolated cell is not a human embryonic stem cell or a cell of a human embryo.

2. The isolated cell of claim 1, wherein said cell further comprises comprising an antibody heavy chain locus comprising in 5' to 3' direction
    (a) a heavy chain intronic enhancer (Eμ);
    (b) a rearranged antibody variable region encoding a rearranged antibody V domain;
    (c) an optional switch sequence; and
    (d) an antibody heavy chain constant region encoding a heavy chain CH1 domain;
    wherein the first antibody heavy chain locus is operable to express an antibody chain comprising in N- to C-terminal direction said rearranged antibody V domain and said heavy chain CH1 domain, and wherein the isolated cell is not a human embryonic stem cell or human embryo.

3. The isolated cell of claim 1, wherein said first antibody kappa light chain locus comprises in 5' to 3' direction:
    (a) a promoter operable for promoting transcription of said rearranged antibody variable region;
    (b) a nucleotide sequence encoding a variable domain signal peptide;
    (c) said intronic enhancer;
    (d) said rearranged antibody variable region; and
    (e) said antibody light chain constant region,
    wherein the first antibody kappa light chain locus is operable to express RNA transcripts encoding in N- to C-terminal direction said variable domain signal peptide sequence fused to the amino acid sequence of said rearranged antibody variable domain.

4. The cell of claim 1, wherein the cell is an ES, iPS, hybridoma or B-cell.

5. The cell of claim 1, wherein the rearranged antibody variable region encodes a rearranged antibody Vκ domain that has a binding specificity for a first predetermined antigen or a first epitope when paired with another rearranged Vκ domain, wherein said first antibody kappa light chain locus is operable to express an antibody chain that comprises a rearranged antibody Vκ domain that retains said binding specificity for said first predetermined antigen or said first epitope when paired with said another rearranged V domain.

6. The cell of claim 1, wherein the cell comprises a second antibody locus that is operable to express a second antibody chain, wherein the second chain comprises a second rearranged antibody V domain that forms a binding site with said first rearranged antibody Vκ domain, wherein the binding site is capable of specifically binding to a predetermined antigen or epitope.

7. The cell of claim 5, wherein the cell comprises a second antibody locus that is operable to express a second antibody chain, wherein the second chain comprises a second rearranged antibody V domain that forms a binding site with the first rearranged antibody V domain, wherein the binding site is capable of specifically binding to a predetermined antigen or epitope, wherein the predetermined antigens are different and said other and second rearranged antibody V domains are different; or wherein the epitopes are different and said other and second rearranged antibody V domains are different.

8. The cell of claim 7, wherein said second rearranged antibody V domain is a VH domain.

9. The cell of claim 1, wherein the variable region is within 0.5 kb 3' of the enhancer.

10. The cell of claim 1, wherein the locus comprises a second enhancer that is 3' of the constant region.

11. The cell of claim 1, wherein the cell is a non-human mammal, mouse, rat or rodent cell.

12. The cell of claim 1, wherein said constant region is at an endogenous antibody locus of the cell.

13. The cell of claim 12 wherein said endogenous locus is an endogenous kappa chain locus.

14. The cell of claim 1, wherein the cell is homozygous for said locus.

15. The cell of claim 1, wherein the cell genome comprises a second antibody locus, wherein the second locus is an unrearranged antibody heavy chain locus comprising in 5' to 3' direction:

(a) one or more VH gene segments;

(b) one or more DH gene segments;

(c) one or more JH gene segments; and (d) a heavy chain constant region encoding one or more CH domains;

wherein the heavy chain locus is operable to express a plurality of heavy chains, optionally comprising a plurality of antigen specificities or affinities, each said heavy chain being capable of pairing with an antibody chain encoded by the first locus to produce paired chains that comprise an antigen binding site.

16. The cell of claim 1, wherein (a) the cell is a mouse cell, said variable region is a human kappa variable region, the intronic enhancer is a mouse intronic enhancer at an endogenous kappa antibody locus of the cell and said constant region is a mouse, rat or human constant region; or (b) the cell is a rat cell, said variable region is a human kappa variable region, the intronic enhancer is a rat intronic enhancer at an endogenous kappa antibody locus of the cell and said constant region is a mouse, rat or human constant region.

17. The cell of claim 1, wherein the rearranged variable region comprises:

(a) human IGκ1-39 and IGκJ1 or IGκ5 and optionally operably connected to human germline IGKV1-39 promoter and/or signal peptide-encoding nucleotide sequence; or (b) human IGK3-20 and IGKJ1 or IGKJ5 and optionally operably connected to human germline IGKV3-20 promoter and/or signal peptide-encoding nucleotide sequence.

18. An isolated population of nonhuman mammalian cells comprising a plurality of spleen cells, bone marrow cells, B-cells or blood cells, wherein each cell in said population of cells comprises a first antibody kappa light chain locus, wherein the locus comprises in 5' to 3' direction:

(a) a light chain Eiκ intronic enhancer;

(b) a rearranged antibody variable region encoding a first rearranged antibody Vκ domain; and (c) an antibody light chain constant region encoding a kappa light chain C domain; wherein said kappa light chain locus is operable to express an antibody chain comprising in N- to C-terminal direction said rearranged antibody Vκ domain and said kappa light chain C domain.

19. An isolated population of hybridoma cells, CHO cells, HEK cells, MEF cells, COS cells, or HeLa cells, wherein each cell in said population of cells comprises a first antibody kappa light chain locus, wherein the locus comprises in 5' to 3' direction:

(a) a light chain Eiκ intronic enhancer;

(b) a rearranged antibody variable region encoding a first rearranged antibody Vκ domain; and (c) an antibody light chain constant region encoding a kappa light chain C domain; wherein said kappa light chain locus is operable to express an antibody chain comprising in N- to C-terminal direction said rearranged antibody Vκ domain and said kappa light chain C domain, wherein the population of cells expresses at least 10 different antibody species, wherein (i) at least 95% of the antibodies share the same kappa light chain VL domain and the population comprises at least 10 different VH domain species; or (ii) the antibodies comprise kappa light chain VL domains derived from the recombination of a first Vκ gene segment and a first Jκ gene segment, wherein at least 95% of all said kappa light chain VL domains derived from said recombination comprise the same VL amino acid sequence and the population comprises at least 10 different VH domain species.

* * * * *